(12) United States Patent
Zhou et al.

(10) Patent No.: US 11,000,403 B2
(45) Date of Patent: May 11, 2021

(54) IMPLANTED TONGUE PULLING DEVICE, PULL PLATE, PULL LINE, RETRACTOR AND METHOD

(71) Applicant: Guangzhou T.K Medical Instrument Co., Ltd., Guangzhou (CN)

(72) Inventors: Xing Zhou, Guangzhou (CN); Xiangmin Zhang, Guangzhou (CN)

(73) Assignee: GUANGZHOU T.K MEDICAL INSTRUMENT CO., LTD., Guandong (CN)

( * ) Notice: Subject to any disclaimer, the term of this patent is extended or adjusted under 35 U.S.C. 154(b) by 870 days.

(21) Appl. No.: 15/642,067

(22) Filed: Jul. 5, 2017

(65) Prior Publication Data

US 2017/0296376 A1 Oct. 19, 2017

Related U.S. Application Data

(60) Continuation of application No. 14/839,207, filed on Aug. 28, 2015, now Pat. No. 9,724,229, which is a
(Continued)

(30) Foreign Application Priority Data

Sep. 29, 2010 (CN) .......................... 201010299195.6

(51) Int. Cl.
*A61F 5/56* (2006.01)
*A61F 2/00* (2006.01)
(Continued)

(52) U.S. Cl.
CPC ................. *A61F 5/566* (2013.01); *A61F 2/00* (2013.01); *A61B 2017/0404* (2013.01);
(Continued)

(58) Field of Classification Search
CPC ...... A61F 5/566; A61F 5/56; A61F 2005/563; A61F 2/20; A61F 2/00; A61F 5/08;
(Continued)

(56) References Cited

U.S. PATENT DOCUMENTS

| 7,210,317 B2 | 5/2007 | Beane et al. |
| 2004/0139975 A1* | 7/2004 | Nelson ....................... A61F 2/20 |
| | | 128/848 |

(Continued)

FOREIGN PATENT DOCUMENTS

| CN | 201320227 Y | 10/2008 |
| CN | 101389288 A1 | 3/2009 |

(Continued)

OTHER PUBLICATIONS

Zhou, Examiner's Report, CA3002395, dated Feb. 5, 2019, 3 pgs.
(Continued)

*Primary Examiner* — Ophelia A Hawthorne
(74) *Attorney, Agent, or Firm* — Morgan, Lewis & Bockius LLP

(57) ABSTRACT

An implanted tongue pulling device including a pull plate, a pull line, a retractor and a method thereof are provided. The tongue pulling device is implanted in the mandible and tongue of a human body, respectively, for tightening the tongue dorsum and/or the tongue base for treating obstructive sleep apnea/hypopnea syndrome (OSAHS). At least three pull lines are used for positioning the pull plate, which is a flat object implanted beneath the tongue dorsum and/or the mucous membrane of the tongue base and includes through holes for the growth of tissues and pull line fixing mechanisms. The pull line includes a draw line and a sleeve. The retractor includes a casing, a control switch and a pull line fixing device mounted on the casing. A patient after surgery can adjust the tightening extent of the implanted
(Continued)

tongue pulling device by pressing the skin outside the control switch, thereby preventing OSAHS.

6 Claims, 54 Drawing Sheets

Related U.S. Application Data division of application No. 13/824,287, filed as application No. PCT/CN2011/080177 on Sep. 26, 2011, now abandoned.

(51) Int. Cl.
*A61B 17/04* (2006.01)
*A61B 17/24* (2006.01)

(52) U.S. Cl.
CPC . *A61B 2017/0496* (2013.01); *A61B 2017/248* (2013.01); *A61F 5/56* (2013.01); *A61F 2250/0004* (2013.01)

(58) Field of Classification Search
CPC .......... A61F 5/58; A61F 5/14; A61B 17/0401; A61M 5/00; A61M 2005/14252; A61C 8/0093; A61C 5/90
See application file for complete search history.

(56) References Cited

U.S. PATENT DOCUMENTS

| | | |
|---|---|---|
| 2005/0092332 A1 | 5/2005 | Conrad et al. |
| 2005/0115572 A1* | 6/2005 | Brooks ................ A61N 2/004 128/863 |
| 2006/0201519 A1 | 9/2006 | Frazier et al. |
| 2006/0235264 A1* | 10/2006 | Vassallo ................ A61B 17/68 600/37 |
| 2006/0235380 A1 | 10/2006 | Vassallo |
| 2007/0233276 A1 | 10/2007 | Conrad |
| 2008/0027560 A1 | 1/2008 | Jackson et al. |
| 2008/0058584 A1 | 3/2008 | Hirotsuka et al. |
| 2009/0084388 A1 | 4/2009 | Bagley et al. |
| 2010/0137905 A1* | 6/2010 | Weadock ................ A61F 2/00 606/228 |

FOREIGN PATENT DOCUMENTS

| | | |
|---|---|---|
| CN | 101732108 A1 | 6/2010 |
| JP | 2006507038 A | 3/2006 |
| JP | 2006508708 A | 3/2006 |
| JP | 2008529608 A | 8/2008 |
| WO | WO2010/051195 | 5/2010 |

OTHER PUBLICATIONS

Zhou, Patent Certificate, EP11828101.3, dated Feb. 27, 2019, 2pgs.
Zhou, Decision to Grant, EP11828101.3, Jan. 31, 2019, 3 pgs.
Zhou, Notice of Grant, PI 2013001119, dated Feb. 28, 2018, 5 pgs.
Zhou, Notice to File a Response, KR2013-7010790, dated Mar. 21, 2018, 8 pgs.
Zhou, Notice of Allowance, KR2013-7010790, dated Aug 31, 2018, 3pgs.
Zhou, Certificate of Patent, KR2013-7010790, dated Nov. 20, 2018, 4 pgs.
Zhou, International Search Report and Written Opinion, PCT/CN2011/080177, dated Dec. 15, 2011, 15 pgs.
Zhou, International Preliminary Report non Patentability, PCT/CN2011/080177, dated Apr. 2, 2013, 7 pgs.
Zhou, Notice of Reasons for Rejection, JP2013-530548, dated May 18, 2015, 8 pgs.
Zhou, Decision to Grant, JP2013-530548, Jul. 7, 2016, 4 pgs.
Zhou, Certificate of Patent, JP2013-530548, Sep. 9, 2016, 4pgs.
Zhou, Notice of Reasons for Rejection, JP2016172418, dated Jun. 28, 2017, 5 pgs.
Zhou, Notice of Reasons for Rejection, JP2016172418, dated Oct. 24, 2017, 7 pgs.
Zhou, Decision to Grant, JP2016-172418, Feb. 2, 2018, 3 pgs.
Zhou, Certificate of Patent, JP2016-172418, dated Mar. 9, 2018, 2 pgs.
Guangzhou T.K Medical Instrument Co., Ltd., Certificate of Grant No. 1, AU 2011307718, Sep. 10, 2015, 1 pg.
Zhou, Extended European Search Report, EP11828101.3, dated Jul. 8, 2017, 8 pgs.
Zhou, Communication Pursuant Rules 70(2) and 70a(2), EP11828101.3, Aug. 24, 2017, 1 pg.
Zhou, Notice of Allowance, 2,812,914, dated Nov. 2, 2017, 1 pg.
Zhou, Notice of Allowance, PI 2013001119, dated Nov. 15, 2017, 3 pgs.

* cited by examiner

Partial enlarged view of part A

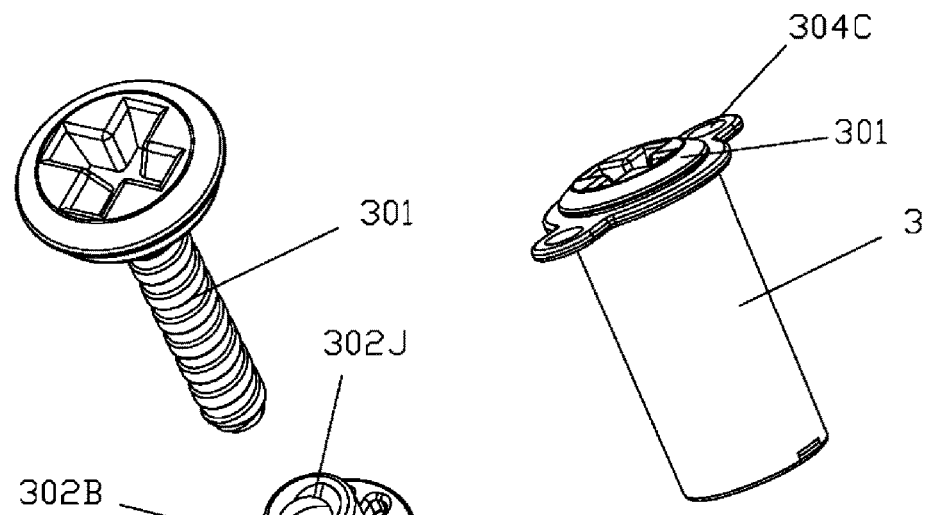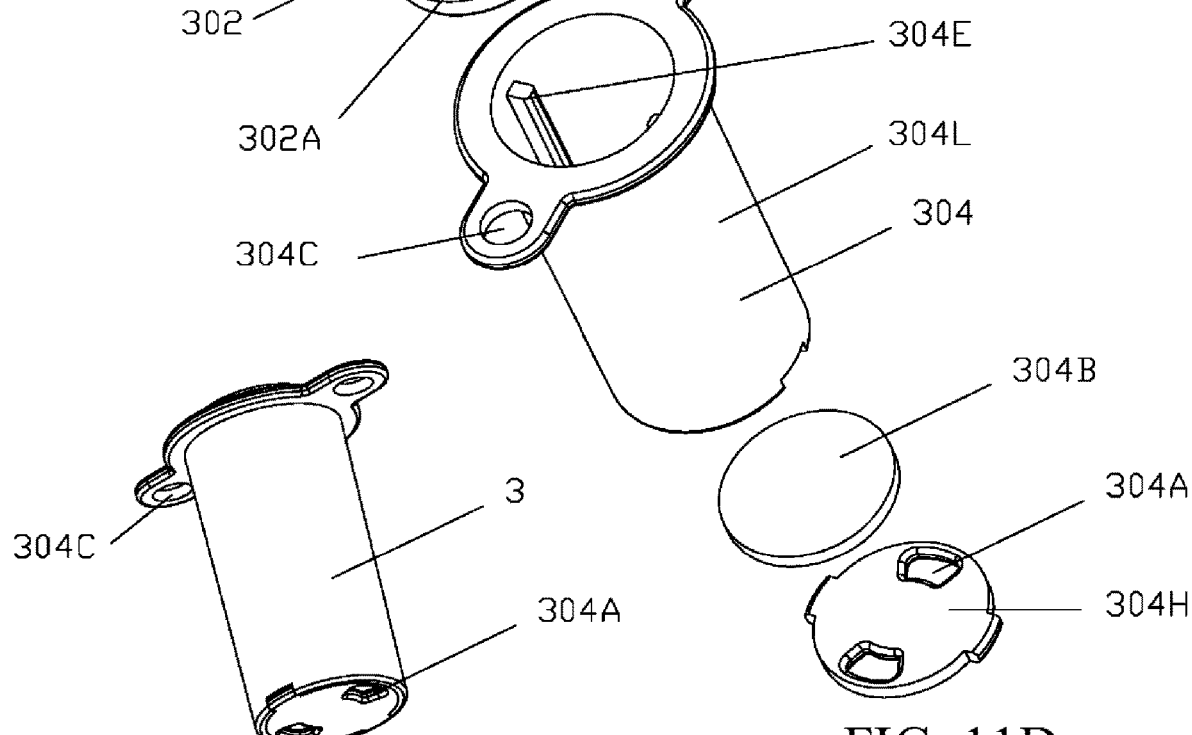

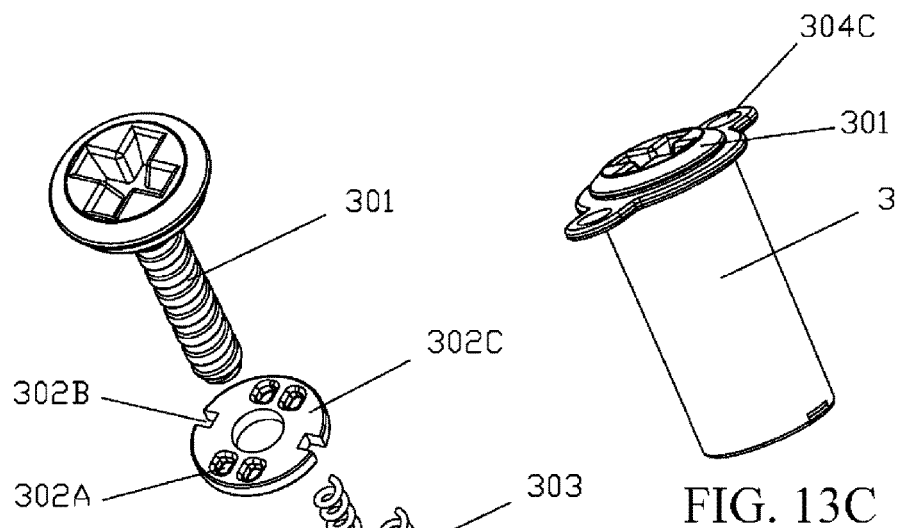
FIG. 13C
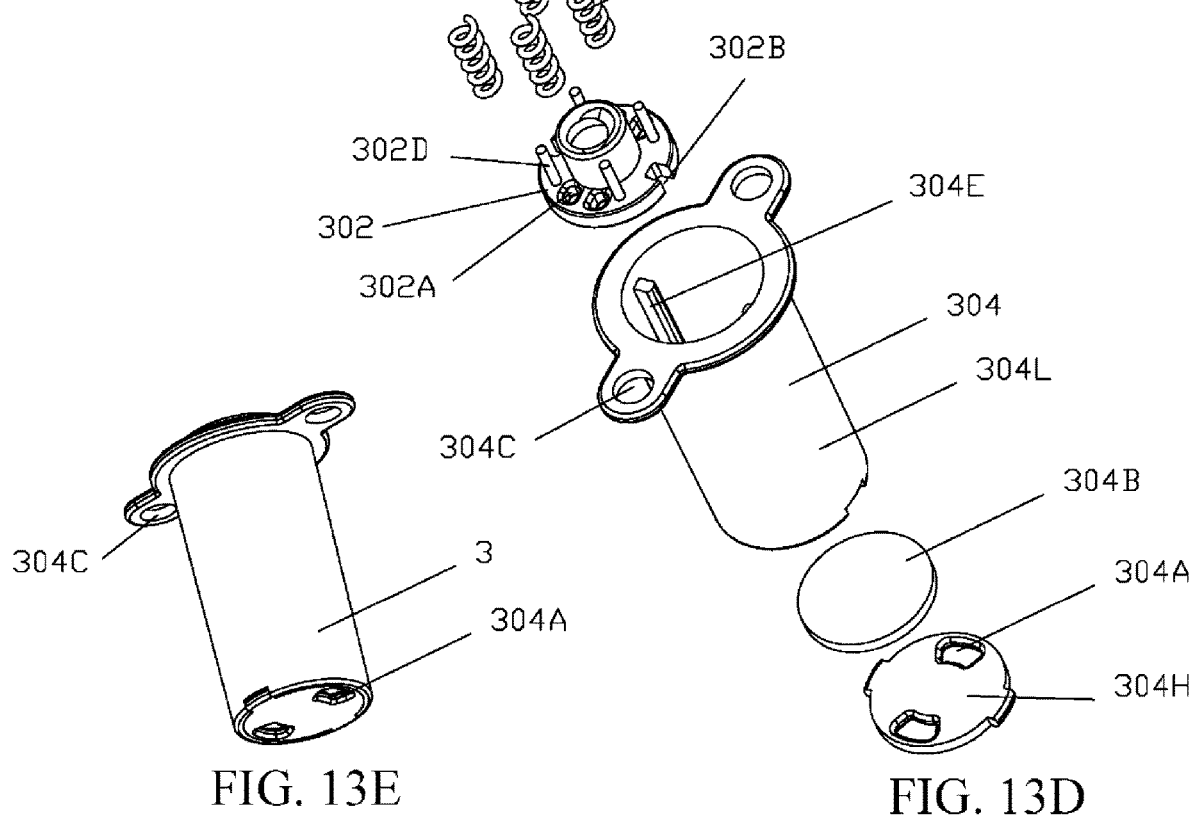
FIG. 13E
FIG. 13D

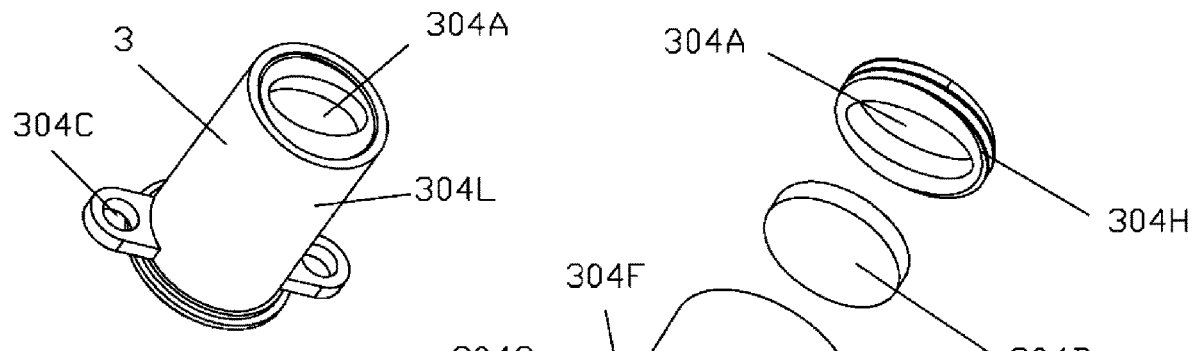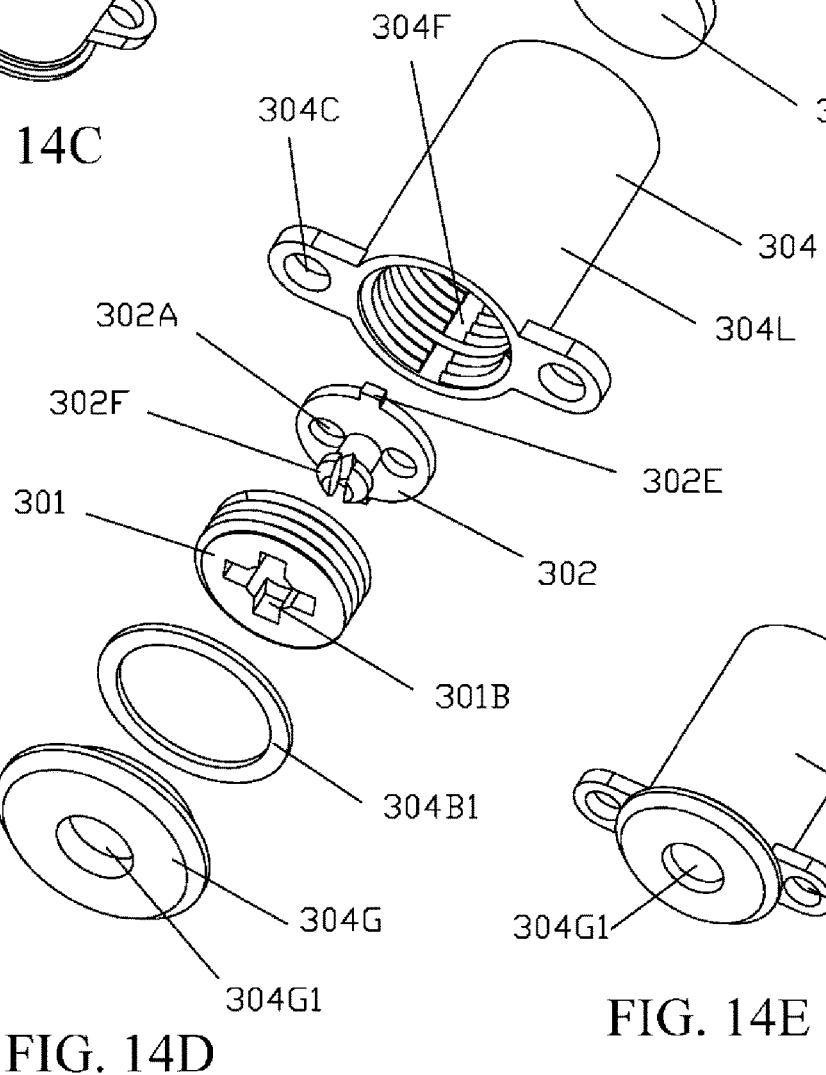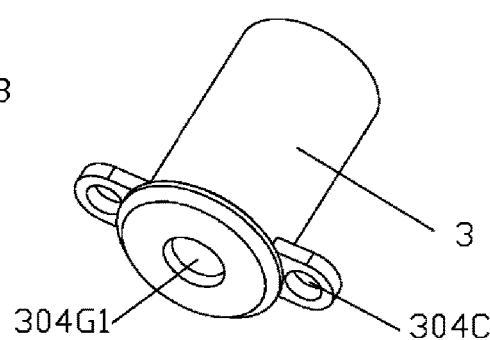
FIG. 14C
FIG. 14D
FIG. 14E

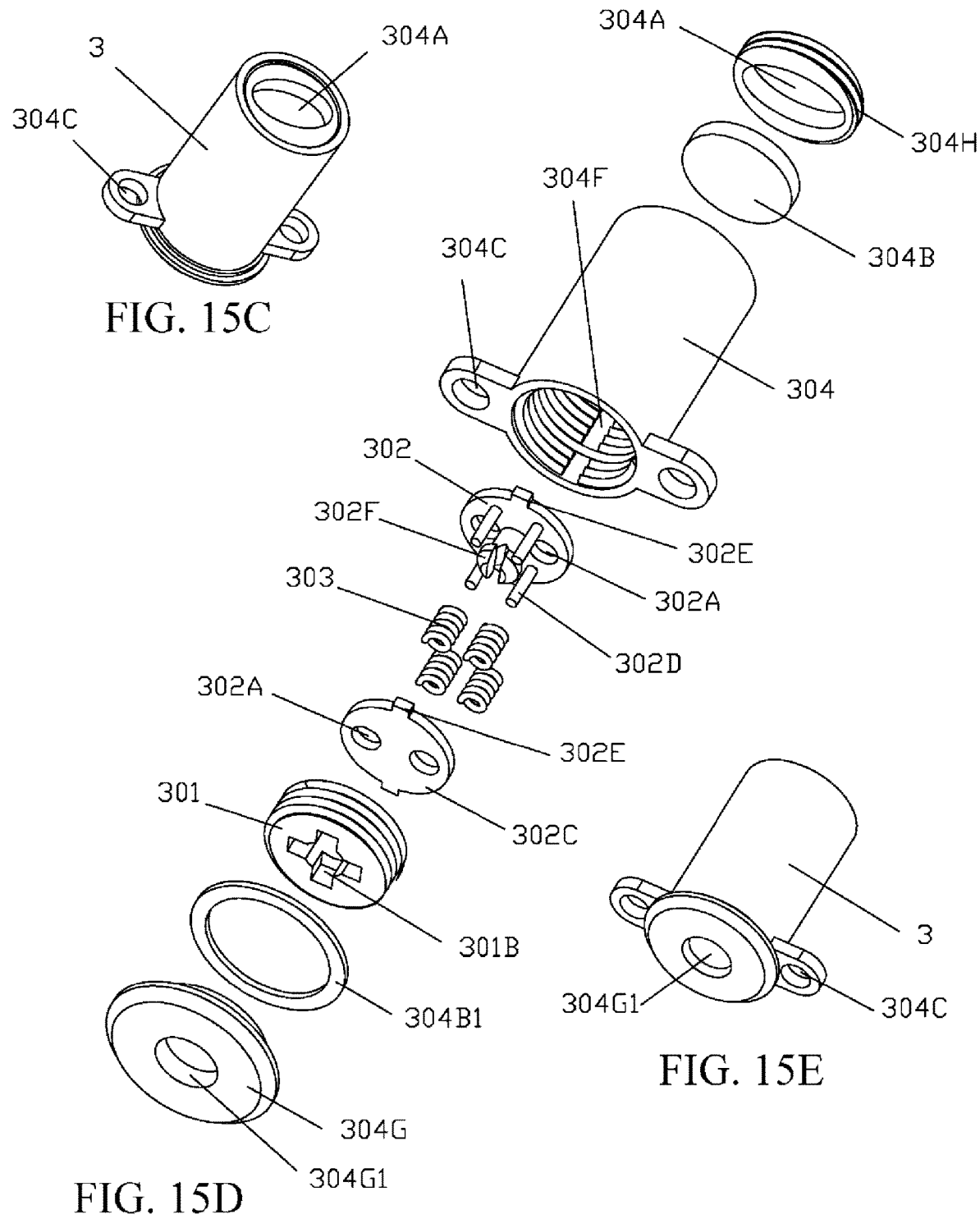

Partial enlarged view of part B

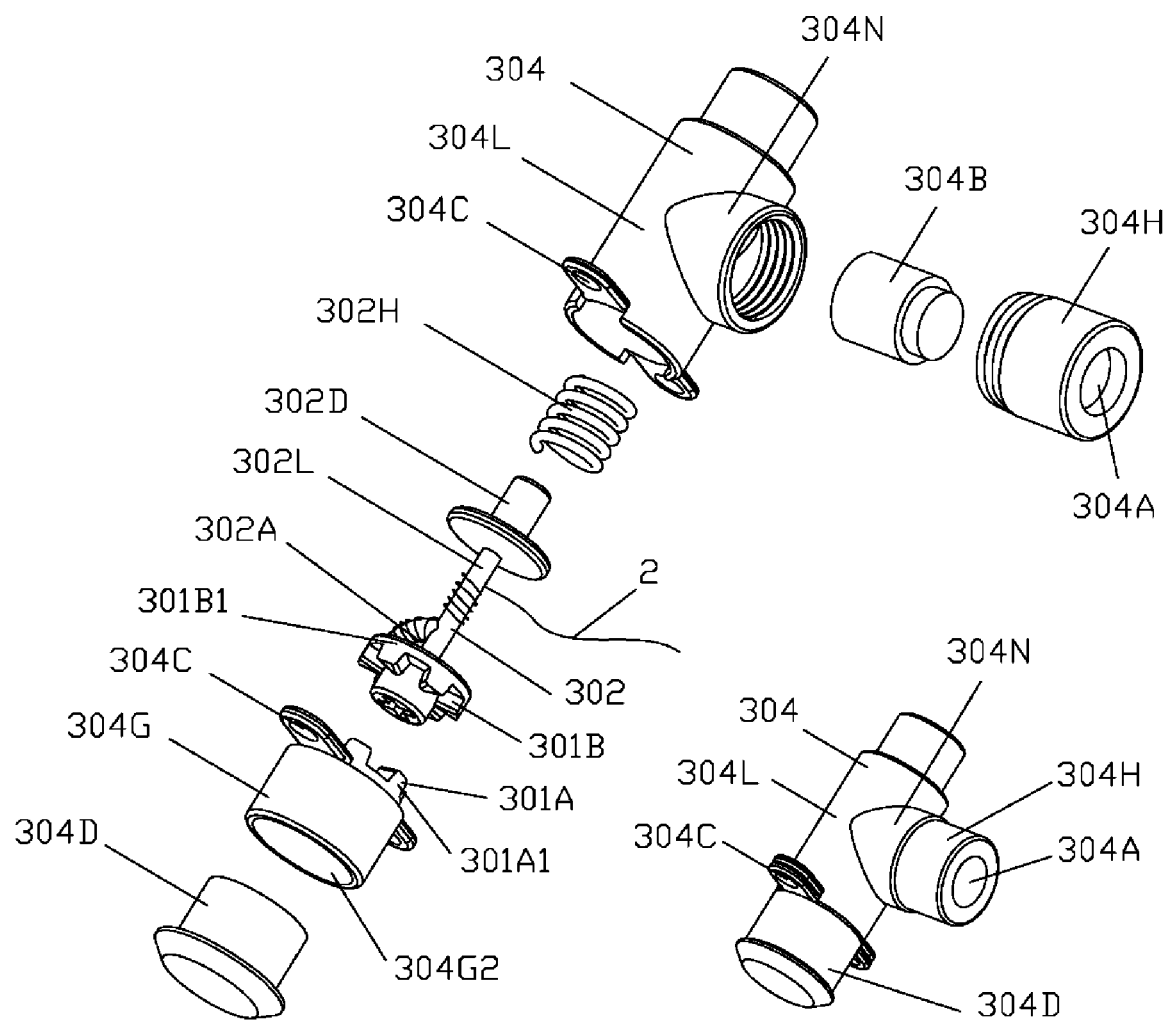

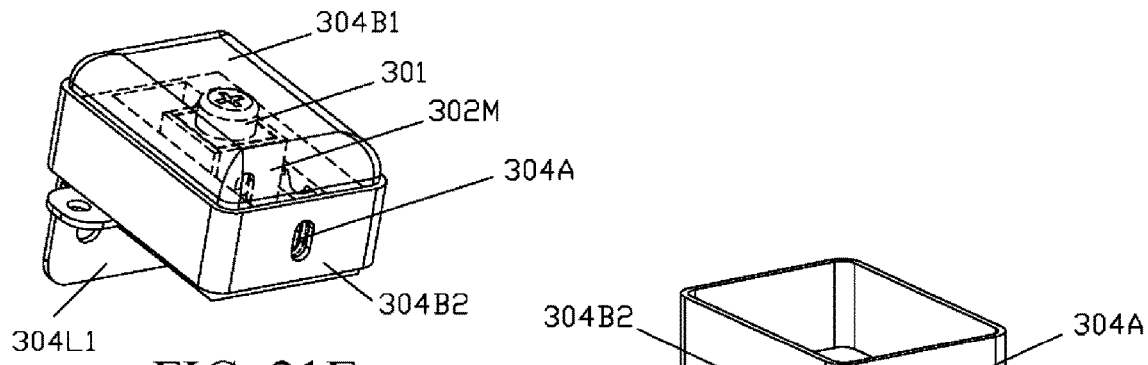
FIG. 21E
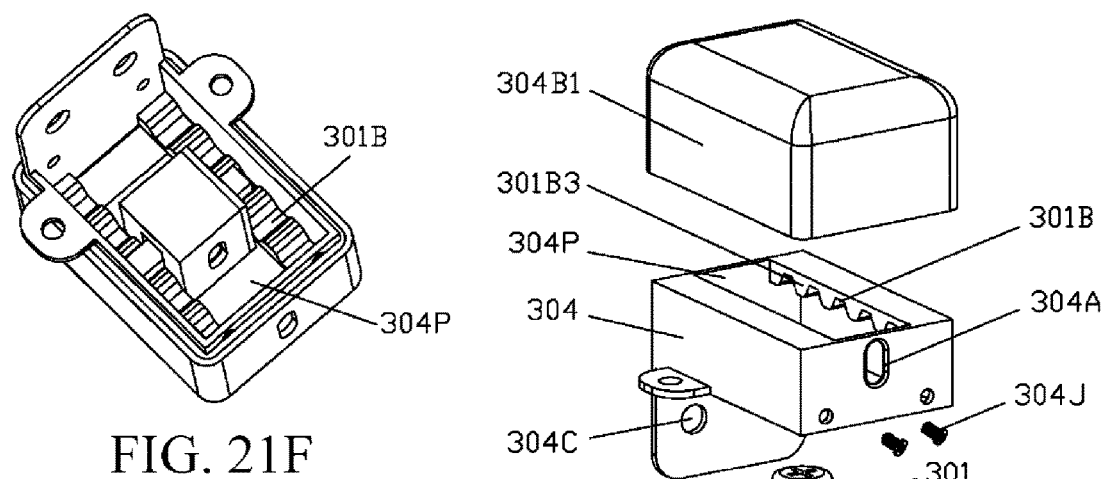
FIG. 21F
FIG. 21G
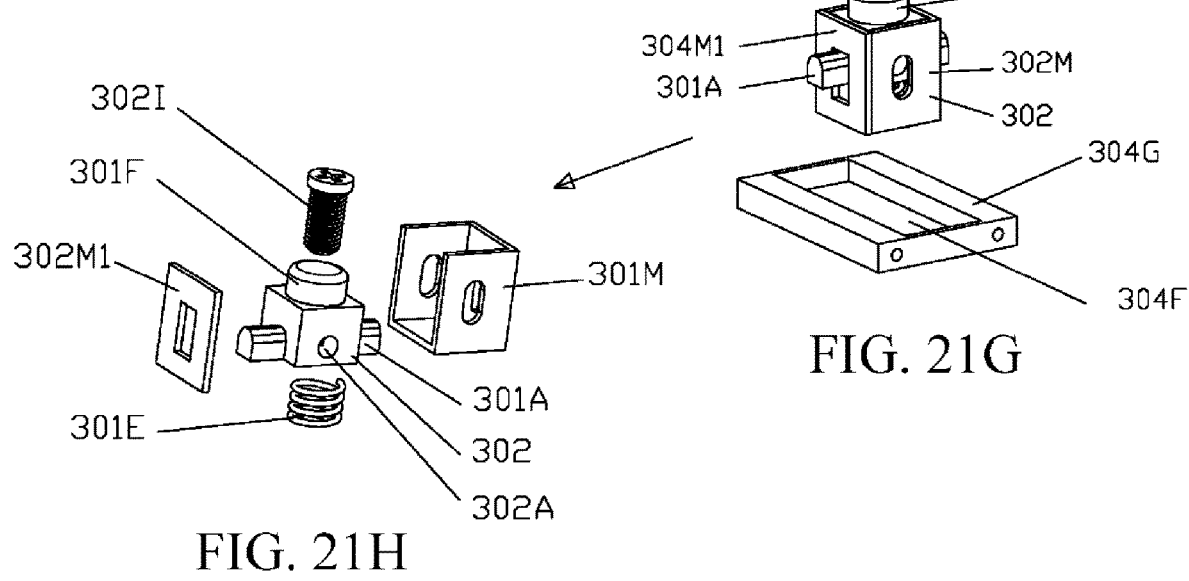
FIG. 21H

Partial enlarged view of part C

IMPLANTED TONGUE PULLING DEVICE, PULL PLATE, PULL LINE, RETRACTOR AND METHOD

CROSS-REFERENCE TO RELATED APPLICATIONS

This application is a continuation application of U.S. patent application Ser. No. 14/839,207, filed Aug. 28, 2015, which is a divisional application of U.S. patent application Ser. No. 13/824,287, filed Mar. 15, 2013, which is a U.S. National Stage application filed under 35 U.S.C. 371 of PCT Patent Application Serial No. PCT/CN11/80177, filed Sep. 26, 2011, which claims benefit to Chinese Patent Application No. 201010299195.6, filed Sep. 29, 2010, all of which are hereby incorporated by reference in their entirety.

BACKGROUND OF THE INVENTION

Field of the Invention

The present invention relates to a tongue pulling device including a pull plate, a pull line, and a retractor, which are implanted into the mandible and the tongue body of a human body, and more particularly to a tongue pulling device including a pull plate, a pull line, and a retractor implanted in the tongue base and/or the tongue dorsum for treating adult obstructive sleep apnea/hypopnea syndrome (OSAHS) and an implantation method.

Related Art

Adult OSAHS is a sleep breathing disorder with clinical features of snoring and apnea caused by upper airway collapse and obstruction during sleep. The major hazard of OSAHS is that frequent sleep apnea and hypopnea result in lowered oxygen saturation levels during sleep for a long term, causing a series of pathologic changes in the human body, thus becoming the cause of various systemic diseases (such as diabetes, hypertension, coronary heart disease, and cerebrovascular accident). According to statistics, currently the morbidity of OSAHS is up to 6%-7% among people, and is extremely high among the middle-aged, which seriously affects the health and quality of life. Therefore, it has been listed by the World Health Organization as one of the major diseases that affect the health and quality of life of people.

As for the pathogenesis of OSAHS, it is generally considered that the main cause is that, pharyngeal muscles for maintaining the upper airway open relax during sleep, resulting in soft tissue collapse and obstruction, and the plane of obstruction is usually located in the palatopharyngeal and glossopharyngeal portions. Many methods for treating OSAHS exist, which include two types, that is, non-surgical treatment and surgical treatment.

Methods of Non-Surgical Treatment Mainly Include:

1. Continuous Positive Airway Pressure (CPAP), in which a breathing machine capable of continuously generating a positive pressure is closely connected with the nose and face of a patient via a nasal mask, so as to prevent collapse and obstruction of the soft tissues of the airway during sleep. The method is currently preferred for treating OSAHS. Though the method has a good effect, it is difficult for approximately 50% of the patients to adapt to the machine, and they cannot endure the machine due to poor compliance, and cannot sleep when wearing the machine.

2. Oral appliance. A device is placed in an oral cavity to move forward the mandible or pull forward the tongue, so as to enlarge the pharyngeal cavity and release the airway obstruction during sleep. The method has many types and produces a certain effect, but most patients cannot adapt to it. The oral appliance leads to irritation and foreign body sensation, causing that the user cannot fall asleep, and may have temporo-mandibular joint injury with long term use.

3. Tongue pulling device. International Application PCT/US2005/00139, Jan. 3, 2005 has disclosed a method and a device for relieving upper airway obstructions. The device includes a mouthpiece that is adapted to form a sealed cavity within a patient' mouth. The patient bites the device during sleep, and extends the tongue into the device, so as to form the sealed cavity. A negative pressure generator is connected with the device, which pulls the patient's tongue and/or soft tissues of the upper airway up and away from the posterior pharyngeal wall to open the airway, so as to prevent the occurrence of OSAHS.

Many patents similar to the tongue pulling device exist. All the patents use the teeth as a supporting point in the oral cavity, and various appliances are designed to change the tension state or position of the tongue or the soft palate during sleep, so as to achieve the objective of treating OSAHS and snoring. These appliances are placed in the oral cavity and are bitten and fixed before sleep, but since persons continuously change the posture and mouth shape during sleep, the appliances often cannot function effectively. In addition, it is uncomfortable and inconvenient for the patients to use the appliances.

Methods of Surgical Treatment Mainly Include:

1. Radiofrequency ablation, which is also referred to as low-temperature plasma radiofrequency ablation, and is a minimally invasive surgical method. An electrode is penetrated into the soft tissues which cause airway obstruction, such as the soft palate, tonsil, and tongue base, and is electrified to induce tissue coagulation, necrosis, fibrosis, and contraction by heating. The method has a certain therapeutic effect, is effective for a slight case, has a poor long-term efficacy, and is ineffective for serious patients. Since the method causes severe post-surgical responses such as tissue edema and pain and requires multiple surgical operations, it is not easily acceptable to the patients.

2. Palatopharyngoplasty. Since Fujita improved the Palatopharyngoplasty of Ikematus, a Japanese scholar, into uvulopalatopharyngoplasty (UPPP) and introduced it to the US in 1981, various improved surgical procedures based on UPPP, including Simmons method, Fairbanks method, Dickson method, Woodson method, Z-palatoplasty (ZPP), uvulopalatal flap (UPF) and H-uvulopalatopharyngoplasty (H-UPPP) have been successively reported in literatures, which made a great contribution to symptom alleviation and recovery of OSAHS patients. Countless patients benefit from the surgical treatment solution. However, in terms of long-term effect, since the mucous membrane and soft palate tissue structure are excessively removed, functional muscles are injured, resulting in complications of nasal regurgitation during swallowing, rhinolalia aperta, and nasopharyngeal stenosis and atresia. It is the leading edge and focus for the research and development of OSAHS treatment technologies nowadays to develop a method and corresponding surgical instruments which create a smaller wound or perform surgical treatment in a minimally invasive manner.

3. Soft palate implantation. International Application PCT/US2002/007966, Mar. 14, 2002, has disclosed a braided palatal implant for snoring treatment. In the invention, the braid is implanted into the soft palate to alter the center of gravity of the soft palate when swinging with the air flow and alter the aerodynamic characteristics of the soft palate, so as to increase the critical air flow speed at the soft palate and the pharynx, thereby preventing snoring from occurring. However, the method fails to prevent OSAHS from occurring, for OSAHS occurs when the soft palate collapses and obstructs the upper airway, so that the method and the adopted implanted instrument cannot be used to treat OSAHS. For serious snoring patients, the risk of OSAHS is increased because the weight at the swinging portion of the soft palate is increased.

4. Tongue reduction surgery. An electrosurgical knife or a laser is applied to remove tissues of the tongue body or tongue base portion, so as to achieve a volume reduction effect. However, the method creates a large wound, and easily hurt important nerves and blood vessels of the tongue, impairing the normal function of the tongue.

5. Tongue advancement surgery, including various surgical procedures such as advancement genioplasty and mandibular sagittal split osteotomy. However, the former has a poor long-term efficacy, and the latter creates a large wound.

6. Surgery using electrical stimulation of the tongue muscles. U.S. Pat. Nos. 7,660,632B2, 6,587,725B1 and 6,251,126B1 introduce a method that uses electrical stimulation of the hypoglossal nerve and the tongue muscles to cause contraction of the tongue muscles when a patient is asleep lying on his/her back, so as to keep the airway behind the tongue. The effectiveness and tolerance of the method needs to be clinically evaluated.

7. Tongue base pulling surgery. In June 1997, Ze'ev Sohn disclosed a method for treating OSAHS by using a surgical suture to pull the tongue dorsum portion and/or the tongue base portion in U.S. Pat. No. 5,988,171, which is characterized in that one end of the surgical suture is fixed using a bone screw, and then the surgical suture is passed across the tongue base portion, drawn, tied at the bone screw, and fixed, so as to pull the tongue base portion to enlarge the airway at the glossopharyngeal portion, thereby treating OSAHS.

The existing technical solution of tongue base pulling has the following three problems:

Firstly, the muscular layer of the tongue base portion belongs to soft tissues, the tongue muscles needs to move during speaking and swallowing every day, and different movements of the tongue muscles produce different forces. Since the surgical suture and the anchor are linear objects, they have a small contact area, and impose a cutting effect on the muscular layer of the tongue base portion under long-term alternate tensions, so that the fixing portion displaces, the tension is loosened, and finally the effect of tightening the tongue base portion is lost, failing to enlarge the airway at the glossopharyngeal portion.

Secondly, since the movement of the tongue is rather complex, the single-wire or double-wire tightening mode easily causes movement from the original implantation site. As a result, a wrong portion is tightened, and the tension is loosened, failing to enlarge the airway at the glossopharyngeal portion.

Thirdly, the tongue base pulling technology in the prior art does not allow adjustment after surgery, and the forward pulling distance of the tongue base portion and the tension can only be determined during surgical implantation. Since the contraction of scar tissues resulting from surgery varies greatly with different subjects, the forward pulling distance determined during surgery may not be that after recovery. However, if it is required to adjust the forward pulling distance of the tongue base portion, another surgery is needed, creating a new wound, and incurring additional medical expenses.

Based on the above, though generating a certain effect, the tongue base pulling method in the prior art for treating OSAHS and snoring still have many defects, and especially it is difficult to control the pulling tension. If the tension is too high, the patient will feel discomfort, and the swallowing and speech functions are affected. If the tension is too low, an effective pulling effect cannot be achieved, resulting in poor efficacy. Therefore, it is necessary to provide a novel technical solution for treating OSAHS, in which the new method should create a wound as small as possible, and the new instrument should be safe, effective, simple, and reliable.

SUMMARY OF THE INVENTION

According to results of clinical and experimental research, it is considered that for OSAHS, airway collapse and obstruction mostly occur at the oropharynx, that is, the posterior part of the palate and the posterior part of the tongue. Various localization diagnosis methods may be applied to localize the plane of obstruction, and a corresponding surgical method is selected so as to improve the efficacy of surgery. Moderate and serious OSAHS cases are often accompanied by multiple plane obstruction, and it is difficult to achieve the desired efficacy by simply adopting a UPPP surgery or other surgical methods aimed at the palatopharyngeal plane. For OSAHS cases accompanied by airway collapse and obstruction at the posterior part of the tongue, a surgical method capable of effectively releasing airway collapse, stenosis, and obstruction at the posterior part of the tongue should also be used. Airway collapse, stenosis, and obstruction are usually caused by factors such as tongue hypertrophy, degraded functions of related nerves and muscles of the tongue, and relaxation and collapse of the tongue muscles, and often occur in obese patients, patients with short mandible and middle-aged and elderly patients.

In the technical background section, various implanted-type tongue base pulling surgeries have been introduced. In order to test the tolerance of the soft tissues of the tongue base portion to the pulling force, swine is used as the experimental subject during animal experiments, and non-absorbable surgical sutures having different diameters are used to pull the tongue base portion of swine. Meanwhile, titanium alloy plates of different sizes and provided with small through holes having a diameter of 2 mm are used as control groups, and experiments are conducted under same conditions, with the experimental result as shown in Table 1 below.

TABLE 1

Evaluation of the resistance of the soft tissues of the tongue base portion of swine to cutting

| Item | Dimensions of stressed surface (mm) | Stressed area (cm$^2$) | Tension (g) | | Pressure (g/cm$^2$) | Cutting effect |
|---|---|---|---|---|---|---|
| 0# surgical suture | Diameter: 0.37; length: 22 | 0.081 | Tension | 200 | 2,457 | Δ |
| | | 0.081 | sion | 500 | 6,143 | Δ |
| | | 0.081 | | 1000 | 12,285 | x |
| | | 0.081 | | 2000 | 24,570 | x |
| | | 0.081 | | 3000 | 36,855 | x |
| 2# surgical suture | Diameter: 0.55; length: 22 | 0.121 | | 200 | 1,653 | Δ |
| | | 0.121 | | 500 | 4,132 | Δ |
| | | 0.121 | | 1000 | 8,264 | x |
| | | 0.121 | | 2000 | 16,529 | x |
| | | 0.121 | | 3000 | 24,793 | x |
| 8# surgical suture | Diameter: 1.05; length: 22 | 0.231 | | 200 | 866 | ○ |
| | | 0.231 | | 500 | 2,165 | Δ |

TABLE 1-continued

Evaluation of the resistance of the soft tissues of the tongue base portion of swine to cutting

| Item | Dimensions of stressed surface (mm) | Stressed area (cm²) | Tension (g) | Pressure (g/cm²) | Cutting effect |
|---|---|---|---|---|---|
| | | 0.231 | 1000 | 4,329 | Δ |
| | | 0.231 | 2000 | 8,658 | x |
| | | 0.231 | 3000 | 12,987 | x |
| 10# surgical suture | Diameter: 1.25; length: 22 | 0.275 | 200 | 727 | ○ |
| | | 0.275 | 500 | 1,818 | Δ |
| | | 0.275 | 1000 | 3,636 | Δ |
| | | 0.275 | 2000 | 7,273 | x |
| | | 0.275 | 3000 | 10,909 | x |
| Plate with two rows of holes | 8 × 22, 10 holes, hole diameter: 2 | 1.446 | 200 | 138 | ○ |
| | | 1.446 | 500 | 346 | ○ |
| | | 1.446 | 1000 | 692 | ○ |
| | | 1.446 | 2000 | 1,383 | Δ |
| | | 1.446 | 3000 | 2,075 | Δ |
| Plate with four rows of holes | 16 × 22, 20 holes hole diameter: 2' | 2.892 | 200 | 69 | ○ |
| | | 2.892 | 500 | 173 | ○ |
| | | 2.892 | 1000 | 346 | ○ |
| | | 2.892 | 2000 | 692 | ○ |
| | | 2.892 | 3000 | 1,037 | ○ |
| Plate with six rows of holes | 24 × 22, 30 holes, hole diameter: 2 | 4.338 | 200 | 46 | ○ |
| | | 4.338 | 500 | 115 | ○ |
| | | 4.338 | 1000 | 231 | ○ |
| | | 4.338 | 2000 | 461 | ○ |
| | | 4.338 | 3000 | 692 | ○ |
| U-shaped plate | 22 × 22, 24 holes, hole diameter: 2 | 3.339 | 200 | 60 | ○ |
| | | 3.339 | 500 | 150 | ○ |
| | | 3.339 | 1000 | 299 | ○ |
| | | 3.339 | 2000 | 599 | ○ |
| | | 3.339 | 3000 | 898 | ○ |

Description 1. Tighten and loosen the suture; tighten and loosen the suture again, where such alternate tensions are applied 100 times. Finally, completely loosen the suture, and observe the cutting trace on the soft tissues of the tongue base portion of swine. If the depth of the cutting trace is greater than 1 mm, it is considered that a significant cutting effect exists.
2. Tighten and loosen the suture; tighten and loosen the suture again, where such alternate tensions are applied 100 times. Finally, completely loosen the suture, and observe the cutting trace on the soft tissues of the tongue base portion of swine. If the soft tissues cannot completely bounce back, with a trace left, but the depth of the trace is smaller than 1 mm, it is considered as slight cutting.
3. The symbol x represents a significant cutting effect. The symbol Δ represents a slight cutting effect. The symbol ○ represents an insignificant cutting effect.

In table 1, alternate tensions are applied, that is, the suture is tightened and loosened, and tightened and loosened again, which is alternately carried out 100 times. Finally, the suture is completely loosened, the implant is taken out, and the cutting trace on the soft tissues of the tongue base portion of swine is observed. If the depth of the cutting trace is greater than 1 mm, it is considered that a significant cutting effect exists, which is represented by the symbol x. If the soft tissues cannot completely bounce back, with a trace left, but the depth of the trace is smaller than 1 mm, it is considered as slight cutting, which is represented by the symbol Δ. If the soft tissues completely bounce back without leaving any significant traces, it is considered that the cutting effect is insignificant, which is represented by the symbol ○.

Experimental data in Table 1 shows that, when the pressure generated by the tension to the soft tissues of the tongue base portion of swine is greater than 7273 g/cm², a significant cutting effect is produced on the soft tissues of the tongue base portion. The larger the pressure generated by the tension is, the more significant the cutting effect will be. On the contrary, the smaller the pressure generated by the tension is, the less likely the cutting effect will be produced. When the pressure generated by the tension is 1037 g/cm², it is determined as an insignificant cutting effect according to the pulling trace left, and when the pressure generated by the tension is greater than 1383 g/cm², it is determined as slight cutting according to the pulling trace left. Therefore, no significant cutting effect is produced when the pressure generated by the tension is 1000 g/cm². Accordingly, in order to prevent cutting, the pressure generated by the implant when applying a tension of 3000 g to retract the soft tissues of the tongue base portion needs to be smaller than 1000 g/cm².

The movement of the tongue is rather complex, and during speech, swallowing and other activities, the force generated during movement of the tongue may reach 2000 g to 3000 g. If the implant that is implanted into the soft tissues of the tongue base portion to produce a pulling effect is a linear object that does not have a large enough stressed area, it easily cuts the soft tissues of the tongue base portion. Firstly, such a cutting effect causes unnecessary injuries. Secondly, after the soft tissues of the tongue base portion are cut, the implant may displace, so that the tension is loosened, and finally the effect of retracting the tongue dorsum portion and/or the tongue base portion is lost, failing to treat OSAHS.

The present invention provides a novel technical solution, which achieves the objective of retracting the tongue base portion, avoids the cutting effect on the soft tissues of the tongue base portion that is caused by retracting the tongue dorsum portion and/or the tongue base portion, and allows adjustment of the pulling force after surgery. The specific solution is as follows:

An implanted tongue pulling device, implanted into the mandible (5) and the tongue body (4) of a human body to tighten the tongue dorsum (42) and/or the tongue base (41), suitable for treating obstructive sleep apnea/hypopnea syndrome (OSAHS), and including:

a pull plate (1), being a flat implant capable of being implanted under the mucous membrane layer of the tongue body, and including through holes (101) facilitating growth of fibrous tissues and pull line fixing mechanisms (102);

a pull line (2), being a thread made of a material capable of being implanted into the human body for a long term; and a retractor (3), including a control switch (301) capable of adjusting a tension of the pull line (2), a pull line fixing device (302) capable of fixing the pull line, and a casing (304), the control switch (301) and the pull line fixing device (302) being mounted in the casing (304), where the pull line (2) has one end connected to the pull plate (1) and the other end connected to the retractor (3).

Further, a distance between the pull plate (1) and the retractor (3) is reduced by 5 mm to 20 mm due to pulling of the pull line (2); and a pressure generated by a force of the tongue muscles on the pull plate (1) due to the reduction in the distance between the pull plate (1) and the retractor (3) is lower than 7000 g/cm², and is preferably 50 g/cm² to 1000 g/cm².

The number of the pull line (2) is at least three, and each of the pull lines (2) has one end connected to the retractor (3) and the other end connected to a corresponding one of at least three pull line fixing mechanisms (102) of the pull plate (1) that are at different spatial positions, so as to spatially position the pull plate (1).

The number of the pull line (2) is at least four, and each of the four pull line (2) has one end connected to the retractor (3) and the other end connected to a corresponding one of the pull line fixing mechanisms (102) that are adjacent to four corners of the pull plate (1), so as to spatially position the pull plate (1).

Spatial positioning of the pull plate (1) by using three pull lines (2) is briefly referred to as a three-line spatial positioning method, spatial positioning of the pull plate (1) by using four pull lines (2) is briefly referred to as a four-line spatial positioning method, and so on.

A pull plate, implanted into the tongue body (4) of a human body to tighten the tongue dorsum (42) and/or the tongue base (41), and suitable for treating obstructive sleep apnea/hypopnea syndrome (OSAHS), where the pull plate (1) is a flat implant capable of being implanted under the mucous membrane layer of the tongue body, and includes through holes (101) facilitating growth of fibrous tissues and pull line fixing mechanisms (102).

Further, the pull line fixing mechanisms (102) are through holes for winding, binding or fixing pull lines; catch-slot or concave-convex engagement mechanisms for fixing pull lines; or rivet fastening mechanisms or thread fastening mechanisms capable of fixing pull lines.

The area of the pull plate (1) is larger than 1.0 cm$^2$, and is preferably 2.5 cm$^2$ to 16 cm$^2$.

The pull plate (1) includes a frame (103) and medical films (104), and the medical films (104) are wrapped on the frame (103).

The frame (103) of the pull plate is a mesh formed by braided elastic wires, and the elastic wires (103C) are capable of moving in a gap (105) between the medical films (104).

When the composite structure having the medical films (104) wrapped on the frame (103) is adopted, a mesh formed by braided elastic wires, for example, a braided mesh of elastic metal wires such as shape memory alloy wires, may be adopted. The elastic wires are capable of moving in the gap formed between the two layers of medical film (104), thereby maintaining good degrees of freedom. The medical films (104) wrapped on the wire mesh effectively increase the stressed area, thereby avoiding cutting the soft tissues of the tongue base. In this way, it is a desirable structure that not only adapts to the requirements of movement of various muscle groups during the movement of the tongue, but also effectively increases the stressed area to avoid cutting the soft tissues of the tongue base.

The pull plate (1) has a curved surface matching with the shape of the tongue dorsum portion and/or the tongue base portion of the human body, and typical geometrical shapes include a rectangle, a square, a trapezoid, a circle, an ellipse, a V-shape, a U-shape and an H-shape.

Main geometric dimensions of the rectangular pull plate (1) include:

a radian R of the curved surface being 10 mm to 120 mm, and preferably 20 mm to 50 mm;

a width W of the curved surface being 10 mm to 50 mm, and preferably 15 mm to 30 mm;

a height H of the curved surface being 10 mm to 50 mm, and preferably 20 mm to 35 mm;

a thickness T of the plate being 0.1 mm to 1 mm, and preferably 0.4 mm to 0.8 mm; and a diameter φ of the through hole (101) being 0.1 mm to 4 mm, and preferably 0.5 mm to 2 mm.

Main dimensions of the U-shaped pull plate (1) include:

a radian R of the curved surface being 10 mm to 120 mm, and preferably 20 mm to 50 mm;

a width W of the curved surface being 10 mm to 50 mm, and preferably 15 mm to 30 mm;

a height H of the curved surface being 10 mm to 50 mm, and preferably 20 mm to 35 mm;

a height H1 being 5 mm to 20 mm, and preferably 5 mm to 15 mm;

a clearance C of the curved surface being 6 mm to 15 mm, and preferably 5 mm to 10 mm;

a thickness T of the plate being 0.1 mm to 1 mm, and preferably 0.4 mm to 0.8 mm; and a diameter φ of the through hole (101) being 0.1 mm to 4 mm, and preferably 0.5 mm to 3 mm.

The pull plate (1) is made of a material selected from a group consisting of, but not limited to: medical metal materials, including medical grade titanium and titanium alloy, medical grade stainless steel, medical grade titanium-nickel shape memory alloy (Nitinol alloy), Ti—Zr—Ta alloy, and amorphous metal materials; and medical polymer materials, including polyamide (PA), polycarbonate (PC), polyurethane (PU), polyethylene/polythene (PE), polypropylene (PP), medical grade polytetrafluoroethylene, fiber reinforced composite materials and the like.

Further, the pull plate (1) includes a left-side pull plate (109A) and a right-side pull plate (109B); the left-side pull plate (109A) and the right-side pull plate (109B) are assembled together through a mechanical connection mechanism (109E); and a gap (109C) and junctions (109D) are formed between the left-side pull plate (109A) and the right-side pull plate (109B).

The gap (109C) has a maximum width (H109) of 1 mm to 10 mm, and preferably 2 mm to 5 mm; and the gap (109C) has a length (L109) of 5 mm to 20 mm, and preferably 5 mm to 15 mm.

The mechanical connection mechanism (109E) is a mechanical fixing mechanism capable of fixing two metal plates, and is selected from a group consisting of a rivet structure, a concave-convex engagement structure, a thread fixing structure and other mechanical fixing mechanisms.

A pull line, implanted into the tongue body (4) of a human body to tighten a pull plate (1), so as to reduce a distance from the tongue dorsum portion (42) and/or the tongue base portion (41) to the mandible (5), where the pull line (2) is a thread made of a material capable of being implanted into the human body for a long term.

Further, the pull line (2) includes a draw line (201) and a sleeve (202); the draw line (201) is a flexible line made of a high-strength medical material; the sleeve (202) is a hollow hose made of a flexible medical material; and the sleeve (202) is mounted over the draw line (201), and the draw line (201) is capable of moving axially in the sleeve (202).

The draw line (201) is a non-absorbable surgical suture.

The sleeve (202) is a multi-layer hollow hose, having an inner layer made of an ultra-smooth material, and an outer layer made of a highly biocompatible material facilitating growth, penetration and bonding of fibrous tissues.

Each draw line (201) of the pull line has a tensile strength of greater than 2000 g, and has a diameter of 0.3 mm to 1.3 mm, and preferably 0.35 mm to 0.6 mm; and the sleeve (202) has an inner diameter of 0.4 mm to 1.5 mm, and preferably 0.4 mm to 1.0 mm.

The material of the pull line (2) is selected from a group consisting of, but not limited to: metal lines; natural fiber lines; and synthetic fiber lines, including polyester lines, polyamide lines, polypropylene lines and the like.

Further, the pull line (2) is formed by spirally braiding a plurality of wires having a diameter of 0.1 mm to 0.5 mm, the material of which is selected from a group consisting of, but not limited to: titanium and titanium alloy wires, Nitinol titanium wires, synthetic fiber wires and other medical material filaments.

The sleeve (202) of the pull line (2) is a corrugated tube. The sleeve (202) of the pull line (2) is a coil spring tube.

The pull line (2) is a necklace structure formed by the draw line (201) and the sleeve (202) constituted by a string of beads (203). The beads (203) may be riveted and fixed to the draw line (201), or may be slidably strung on the draw line (201).

A retractor, implanted on the mandible (5) of a human body to fix a pull line (2), where the retractor (3) includes a control switch (301) capable of adjusting a tension of the pull line (2), a pull line fixing device (302) capable of fixing the pull line, and a casing (304), the control switch (301) and the pull line fixing device (302) being mounted in the casing (304).

Further, the control switch (301) of the retractor (3) is a thread structure or concave-convex engagement structure, and the tension of the pull line (2) is increased or reduced by adjusting the control switch (301).

The control switch (301) includes a tightening switch (301C) capable of increasing the tension of the pull line (2) and a loosening switch (301D) capable of reducing the tension of the pull line (2).

The control switch (301) includes a ratchet (301B2), the ratchet (301B2) is driven to rotate when the tightening switch (301C) is pressed, and the ratchet (301B2) is released when the loosening switch (301D) is pressed.

The control switch (301) includes a positioning convex step (301A) and a positioning concave groove (301B) engaged with each other, and the positioning convex step (301A) and the positioning concave groove (301B) form a concave-convex engagement structure for positioning.

The control switch (301) includes tooth racks (301B3), when the control switch (301) is pressed, the positioning convex step (301A) of the control switch is capable of moving longitudinally along the tooth racks (301B3); and when the control switch (301) released, the positioning convex step (301A) of the control switch is automatically engaged into the positioning concave groove (301B) for the tooth racks (301B3), and the positioning convex step (301A) of the control switch does not move longitudinally along the tooth racks (301B3).

The retractor (3) has a winding-type structure or displacement-type structure for adjusting the tension of the pull line (2); movement of the pull line (2) of the winding-type structure is achieved by winding the pull line (2) onto the bobbin (302L) through rotation of the bobbin (302L); and the displacement-type structure is achieved by rotary movement of a thread structure or reciprocating movement of a concave-convex engagement structure.

The retractor (3) includes an anti-cutting buffer device (303), the anti-cutting buffer device (303) is a spring structure, and the anti-cutting buffer device (303) is disposed inside the casing (304) and connected to the pull line fixing device (302); and when the tension of the pull line (2) is greater than a preset operational driving force of the spring structure or a pressure on the pull plate (1) is greater than a set value, the spring structure of the anti-cutting buffer device (303) deforms to automatically buffer the tension of the pull line (2), so as to prevent the pull plate (1) from cutting the tongue muscles.

Further, the operational driving force of the spring structure of the anti-cutting buffer device (303) is smaller than 1000 g, or the preset value of the pressure on the pull plate (1) is smaller than 7000 g/cm$^2$, and is preferably 500 g/cm$^2$ to 1500 g/cm$^2$.

The retractor (3) includes a restoring spring (305), the restoring spring (305) is a coil spring; and the restoring spring (305) stores elastic deformation energy when compressed, and releases the stored elastic deformation energy when released.

The retractor (3) includes a protective sheath (306), the protective sheath (306) is a hollow hose made of a flexible medical material, and the protective sheath (306) is mounted in the casing (304).

The protective sheath (306) is a multi-layer hollow hose, having an inner layer made of an ultra-smooth material, and an outer layer made of a highly biocompatible material facilitating growth of fibrous tissues.

A silica gel plug (304D) in a color similar to the skin color of the human body is disposed on the casing (304), the silica gel plug (304D) is connected to the casing (304), and after the silica gel plug (304D) is removed, the tension of the pull line (2) is adjusted by adjusting the control switch (301); during sleep, the pull line (2) is tightened to apply a tension to the pull plate (1), so as to tighten the tongue dorsum portion and/or the tongue base portion toward the mandible, thereby maintaining the airway at the palatopharyngeal portion open; and in a non-sleep state, the pull line (2) is loosened to release the pull plate (1) from the pull line (2), so as to allow the tongue to move freely, thereby maintaining normal swallowing and speech functions.

The retractor (3) is made of a material selected from a group consisting of, but not limited to: medical metal materials, including medical grade titanium and titanium alloy, medical grade stainless steel, medical grade titanium-nickel shape memory alloy (Nitinol alloy), Ti—Zr—Ta alloy, and amorphous metal materials; and medical polymer materials, including polyamide (PA), polycarbonate (PC), polyurethane (PU), polythylene/polythene (PE), polypropylene (PP), medical grade polytetrafluoroethylene, fiber reinforced composite materials and the like.

A method for treating obstructive sleep apnea/hypopnea syndrome (OSAHS), including:

providing an implanted tongue pulling device, where the tongue pulling device is implanted into the mandible (5) and the tongue body (4) of a human body to tighten the tongue dorsum (42) and/or the tongue base (41), is suitable for treating OSAHS, and includes:

a pull plate (1), being a flat implant capable of being implanted under the mucous membrane layer of the tongue body, and including through holes (101) allowing growth and penetration of fibrous tissues and pull line fixing mechanisms (102);

a pull line (2), being a thread made of a material capable of being implanted into the human body for a long term; and a retractor (3), including a control switch (301) capable of adjusting a tension of the pull line (2), a pull line fixing device (302) capable of fixing the pull line, and a casing (304), the control switch (301) and the pull line fixing device (302) being mounted in the casing (304), where the pull line (2) has one end connected to the pull plate (1) and the other end connected to the retractor (3);

performing a surgery under anesthesia: incising tissues at a front portion of the mandible or a bottom portion of the mandible, and fixing the retractor (3) to the mandible by using a screw (10); then, using an electrosurgical needle knife to incise the mucous membrane in front of circumvallate papillae of the tongue dorsum, separating the mucous membrane till the tongue base, and implanting the pull plate (1) into the muscular layer under the mucous membrane layer of the tongue dorsum portion (42) and/or the tongue base portion (41) of the human body; fixing one end of each of four pull lines (2) to a corresponding one of four corners of the pull plate (1), and passing the other end of each of the four pull lines (2) through the tongue body (4) under the guide of a latch needle, drawing the other end to the vicinity of the mandible (5), and connecting the other end to the retractor (3); adjusting the control switch (301) to tighten the pull line (2), so as to reduce the distance between the pull plate (1) and the retractor (3), where a pressure generated by a force of the tongue muscles on the pull plate (1) due to the reduction in the distance between the pull plate (1) and the retractor (3) is lower than 7000 g/cm$^2$, and is preferably 50 g/cm$^2$ to 1000 g/cm$^2$; and finally, suturing the incision;

where, the implanted tongue pulling device pulls the tongue dorsum portion (42) and/or the tongue base portion (41) forward by a distance of 5 mm to 20 mm; and the implanted tongue pulling device is capable of adjusting the forward pulling distance of the tongue dorsum portion (42) and/or the tongue base portion (41) by adjusting the control switch (301) after surgery.

Further, the retractor (3) is fixed to the front portion (51) of the mandible, and the pull lines (2) are passed across the bottom portion (52) of the mandible and connected to the pull plate (1) that is implanted into the muscular layer under the mucous membrane layer of the tongue base portion and/or the tongue dorsum portion.

The retractor (3) is fixed to the bottom portion (52) of the mandible, and each of the pull lines (2) has one end connected to the retractor (3), and the other end connected to the pull plate (1) that is implanted into the muscular layer under the mucous membrane layer of the tongue base portion and/or the tongue dorsum portion.

Method 1 for Adjusting the Forward Pulling Distance of the Tongue Dorsum Portion (42) and/or the Tongue Base Portion (41) after Surgery:

The implanted tongue pulling device is capable of adjusting a pulling degree of the tongue dorsum portion (42) and/or the tongue base portion (41) after surgery, characterized in that:

the retractor (3) of the implanted tongue pulling device is mounted on the front surface of the mandible and close to the bottom portion of the mandible so that the control switch (301) faces upward, and after surgery, the patient pulls apart the lower lip, inserts a screwdriver (9) into a cross slot of the control switch (301), and rotates the control switch (301) to tighten or loosen the pull lines (2), so as to adjust the forward pulling distance of the tongue dorsum portion (42) and/or the tongue base portion (41).

Method 2 for Adjusting the Forward Pulling Distance of the Tongue Dorsum Portion (42) and/or the Tongue Base Portion (41) after Surgery:

The implanted tongue pulling device is capable of adjusting a pulling degree of the tongue dorsum portion (42) and/or the tongue base portion (41) after surgery, characterized in that:

the retractor (3) of the implanted tongue pulling device is mounted on the front surface of the mandible and close to the bottom portion of the mandible so that the control switch (301) faces downward, and the silica gel plug (304D) on the casing is exposed out of the skin at the bottom portion of the mandible; and when adjustment is needed, the silica gel plug (304D) is removed, and the screwdriver (9) is used to rotate the control switch (301) to tighten or loosen the pull lines (2), so as to adjust the forward pulling distance of the tongue dorsum portion (42) and/or the tongue base portion (41).

Method 3 for Adjusting the Forward Pulling Distance of the Tongue Dorsum Portion (42) and/or the Tongue Base Portion (41) after Surgery:

The implanted tongue pulling device is capable of adjusting a pulling degree of the tongue dorsum portion (42) and/or the tongue base portion (41) after surgery, characterized in that:

the retractor (3) of the implanted tongue pulling device is mounted on the front surface of the mandible and close to the bottom portion of the mandible, and the control switch (301) is divided into a tightening switch (301C) and a loosening switch (301D), and adopts a ratchet (301B2) as an adjustment structure;

before sleep, the tightening switch (301C) is pressed from a position outside the skin of the mandible corresponding to the tightening switch (301C); each time when the tightening switch (301C) is pressed, a positioning convex step (301A) on the tightening switch (301C) pushes the ratchet (301B2) to rotate by one step, so as to drive the pull line fixing device (302) to move to tighten the pull lines (2), thereby increasing the forward pulling distance of the tongue dorsum portion (42) and/or the tongue base portion (41), and a positioning convex step (301A) on the loosening switch (301D) stops reverse rotation of the ratchet (301B2), so as to prevent loosening of the tightened pull lines (2); and in a non-sleep state, the loosening switch (301D) is pressed from a position outside the skin of the mandible corresponding to the loosening switch (301D); and when the loosening switch (301D) is pressed, the ratchet (301B2) is released, the ratchet (301B2) is in a free state, the pull lines (2) are in a loosened state, and under the movement of the tongue or the action of a restoring spring (305), the forward pulling distance of the tongue dorsum portion (42) and/or the tongue base portion (41) is reduced.

Method 4 for Adjusting the Forward Pulling Distance of the Tongue Dorsum Portion (42) and/or the Tongue Base Portion (41) after Surgery:

The implanted tongue pulling device is capable of adjusting a pulling degree of the tongue dorsum portion (42) and/or the tongue base portion (41) after surgery, characterized in that:

the retractor (3) of the implanted tongue pulling device is mounted at the bottom portion of the mandible, and after surgery, by pressing the control switch (301) from the skin of the bottom portion of the mandible of the patient and at the same time pushing or pulling the control switch (301), the patient is capable of adjusting the pulling degree of the tongue dorsum portion and/or the tongue base portion being pulled by the pull lines (2):

in a non-sleep state, the control switch (301) is pressed and pushed toward the tongue base portion so that the pull lines (2) apply a small pulling force to the tongue base portion or are completely in a loosened state, and then the control switch (301) is released so that the control switch (301) is automatically positioned and locked, that is, the control switch (301) is adjusted to an "off" state, and at this time, the tongue base portion is almost unconstrained, and the tongue is capable of moving freely during speaking, swallowing and other activities; and before sleep, the control switch (301) is pressed and pulled toward the mandible so that the control switch (301) is adjusted to an "on" state, and at this time, the pull lines (2)

apply a large pulling force to the tongue base portion, so that the tongue base portion is in an effective retracted state, and the tongue base portion is pulled forward, so as to maintain the palatopharyngeal portion open, thereby preventing OSAHS.

Method 5 for Adjusting the Forward Pulling Distance of the Tongue Dorsum Portion (42) and/or the Tongue Base Portion (41) after Surgery:

The implanted tongue pulling device is capable of adjusting a pulling degree of the tongue dorsum portion (42) and/or the tongue base portion (41) after surgery, characterized in that:

the retractor (3) of the implanted tongue pulling device is mounted on the front surface of the mandible and close to the bottom portion of the mandible, and a degree of comfort is set by adjusting the control switch (301); and the control switch (301) is adjusted so that the pull lines (2) maintain a proper tension to maintain the forward pulling distance of the tongue dorsum portion (42) and/or the tongue base portion (41) at a proper distance, so as to move the tongue dorsum portion (42) and/or the tongue base portion (41) forward while ensuring comfort during movement of the tongue, and maintain the palatopharyngeal portion open, thereby preventing OSAHS.

The tongue pulling device and the implantation method provided in the present invention effectively solve the technical problem that the tongue muscles are easily cut during pulling, and the patient can adjust the tongue pulling device of the present invention after surgery to reduce the pulling force in the non-sleep state and ensure effective pulling during sleep, so as to enlarge the airway at the palatopharyngeal portion, thereby preventing OSAHS.

The present invention has the following innovative points:

The structure of the pull plate (1) is used to reduce the pressure generated by the tension, so as to prevent the pull plate (1) from cutting the soft tissues of the tongue base portion. The pull line fixing mechanisms (102) disposed on the pull plate (1) facilitate fixing the pull lines (2) during surgery. The through holes (101) disposed on the pull plate (1) facilitate growth and penetration of human tissues, so as to provide a function of fixing the pull plate (1). In addition, the pull plate (1) has a degree of curvature matching with the soft tissues of the tongue base portion, and is a spatial curved surface, that is, is adapted for growth and penetration of human tissues, and also has a positioning function to prevent sliding and shifting. Since the pull plate (1) has a large enough contact area, the pressure generated by the tension is greatly reduced, and the pressure generated by the tension may be controlled below 1000 g/cm$^2$, so as to avoid cutting the soft tissues of the tongue base portion. Therefore, the pull plate (1) can be implanted for a long term without injuring the soft tissues of the tongue base portion. Particularly, when the pull plate (1) adopts the composite structure having the medical films (104) wrapped on the frame (103), the frame (103) having an elastic mesh structure formed by braided metal wires can move freely in the gap (105) between the medical films (104) wrapped on the frame (103), and human tissues can be attached to and grow on the medical films (104). In this way, the pull plate (1) can desirably adapt to the complex movement of the tongue without affecting the effective pulling to the tongue base portion, and at the same time significantly reduce the pressure during pulling, thereby avoiding cutting the soft tissues of the tongue base portion.

Three or more pull lines (2) are used to fix the pull plate (1), thereby achieving spatial fixing and positioning. The pull plate (1) is a spatial curved plate. Due to the complex movement of the tongue, a single pull line easily causes sliding or shifting, leading to loss of the pulling effect. Effective spatial positioning and pulling can be achieved only by using more than three pull lines (2), so that the pulling effect can be achieved for any movement of the tongue without causing movement of the pull plate (1). In a preferred solution of the present invention, four-line four-corner fixing and pulling is adopted, which effectively achieves spatial positioning.

The use of the retractor (3) not only facilitates adjustment and fixing during surgery, but also facilitates adjusting the tightening degree of the pull line after surgery. The retractor (3) includes the control switch (301) capable of adjusting the tension of the pull line (2) and the pull line fixing device (302) capable of fixing the pull line. By rotating, pushing/pulling, or pressing the control switch (301), the tightening degree of the pull line can be adjusted, so as to control the pulling distance and the pulling force for the tongue base portion and/or the tongue dorsum portion. In the non-sleep state, the control switch (301) is adjusted to the "off" state, and at this time, the tongue base portion receives a small pulling force or is completely in a loosened state, thereby ensuring free movement of the tongue during speaking, swallowing and other activities. Before sleep, the control switch (301) is adjusted to the "on" state, and at this time, the tongue base portion and/or the tongue dorsum portion receives a large pulling force, and is thus in an effective retracted state, so as to maintain the palatopharyngeal portion open, thereby preventing OSAHS.

Surgical Method for Implanting a Tongue Pulling Device with a Combined-Type Pull Plate of the Present Invention:

A surgical method for implanting a tongue pulling device with a combined-type pull plate of the present invention mainly includes the following steps:

Firstly, surgical sites such as the tongue and the oral cavity are disinfected under anesthesia according to general requirements of oral cavity, head and neck surgeries.

Secondly, one end of each of two pull lines is fixed to a left-side pull plate (109A), and one end of each of another two pull lines is fixed to a right-side pull plate (109B); then, a surgical knife is used to make incisions of about 3 mm to 6 mm at a position about 10 mm to 15 mm from circumvallate papillae of the tongue and beside two sides of the midline of the tongue, and of about 8 mm transversely cutting the mucous membrane of the tongue, and a moderately curved hemostatic forceps is used to separate the mucous membrane toward the tongue base, so as to form an about 40 mm deep surgical cavity on left and right sides of the midline of the tongue respectively; a special surgical forceps (13) is used to simultaneously insert the left-side pull plate (109A) and the right-side pull plate (109B) into the surgical cavities below the mucous membrane of the tongue dorsum (42) and/or the tongue base (41) to be retracted, where during insertion, a distance between the left-side pull plate (109A) and the right-side pull plate (109B) is maintained at 1 mm to 10 mm, and at the same time, the left-side pull plate (109A) and the right-side pull plate (109B) are maintained symmetrical; and thirdly, the special surgical forceps (13) is closed, and the left-side pull plate (109A) is assembled and fixed to the right-side pull plate (109B) through a mechanical connection mechanism (109E), where fibrous tissues of the tongue muscles are sandwiched in a gap (109C) between the left-side pull plate (109A) and the right-side pull plate (109B), and through the gap (109C), continuity of musculus genioglossus and other fibrous tissues to the fibrous tissues under the mucous membrane of the tongue dorsum or the tongue base is maintained.

Thirdly, the pull lines (2) are drawn to the vicinity of the mandible (5) by using a guide needle.

Fourthly, an incision is made along the lower lip to expose the mandible (5), the retractor (3) is fixed to the mandible (5), and at the same time, the pulling lengths of the four pull lines (2) are adjusted respectively, and all the four pull lines (2) are fixed to the retractor (3).

Fifthly, the incisions are sutured, thus completing the surgery.

The Tongue Pulling Device with the Combined-Type Pull Plate of the Present Invention has the Following Advantages:

With the use of the flat pull plate (1), the contact area between the pull plate (1) and the retracted portion of the tongue body is increased, so that the pressure generated during pulling is greatly reduced, which not only improves the pulling effect, but also avoids cutting the tongue tissues when the tongue body is retracted, thereby reducing injuries. Particularly, with the use of the combined-type pull plate (1) formed by the left-side pull plate (109A) and the right-side pull plate (109B), continuity of musculus genioglossus and other fibrous tissues to the fibrous tissues under the mucous membrane of the tongue dorsum or the tongue base is maintained to the maximum extent, thereby further enhancing the capability of spatially positioning the pull plate (1) and improving the effect of retracting the tongue dorsum (42) and/or the tongue base (41).

Secondly, with the use of the spatial pulling mode with four pull lines (2), shifting of the pull plate (1) after implantation is effectively prevented. Particularly, after the combined-type pull plate (1) formed by the left-side pull plate (109A) and the right-side pull plate (109B) is used, rivets (109E1) for fixing the left-side pull plate (109A) and the right-side pull plate (109B) are inserted into musculus genioglossus, which further improves the stability of the pull plate (1) so that the pull plate (1) does not easily displace.

Thirdly, the retractor (3) is conveniently fixed to the mandible (5), and the pull lines (2) are fixed to the retractor (3), so that the pulling degree of the pull lines (2) can be conveniently adjusted to accurately control the pulling distance and the pulling force, thereby achieving an optimal therapeutic effect. Particularly, when the double-button type retractor (3) that can be adjusted after surgery is used, not only the doctor can conveniently adjust and fix the pull lines (2) during surgery, but also woundless adjustment can be achieved after surgery.

BRIEF DESCRIPTION OF THE DRAWINGS

FIG. 11C is a three-dimensional view showing the top structure of the retractor of FIG. 11A;

FIG. 11D is an exploded view of the retractor of FIG. 11A;

FIG. 11E is a three-dimensional view showing the bottom structure of the retractor of FIG. 11A;

FIG. 13C is a three-dimensional view showing the top structure of the retractor of FIG. 13A;

FIG. 13D is an exploded view of the thread-type retractor of FIG. 13A.

FIG. 13E is a three-dimensional view showing the bottom structure of the thread-type retractor of FIG. 13A;

FIG. 14C is a three-dimensional view showing the bottom structure of the retractor of FIG. 14A;

FIG. 14D is an exploded view of the retractor of FIG. 14A;

FIG. 14E is a three-dimensional view showing the top structure of the retractor of FIG. 14A;

FIG. 15C is a three-dimensional view showing the bottom structure of the retractor of FIG. 15A;

FIG. 15D is an exploded view of the retractor of FIG. 15A;

FIG. 15E is a three-dimensional view showing the top structure of the retractor of FIG. 15A;

FIG. 18C is an exploded view of the retractor of FIG. 18A;

FIG. 18D is a three-dimensional view showing the side structure of the retractor of FIG. 18A;

FIG. 21E is a three-dimensional view showing the control switch of FIG. 21A;

FIG. 21F is a three-dimensional view showing positioning tooth racks of FIG. 21A;

FIG. 21G is an exploded view of the retractor of FIG. 21A;

FIG. 21H is an exploded view of a positioning slide block;

FIG. 27E1 is an enlarged view of part M of FIG. 27E;

FIG. 27L is a view depicting the working principle of a tongue pulling device using the combined-type pull plate according to the present invention;

FIG. 28A is a schematic structural view of a U-shaped combined-type pull plate according to the present invention;

FIG. 28B is a side view of FIG. 28A;

FIG. 28C is a left view of FIG. 28A;

FIG. 28D is a right view of FIG. 28A;

FIG. 28E is a G-G cross-sectional view of FIG. 28A;

Figure 1:
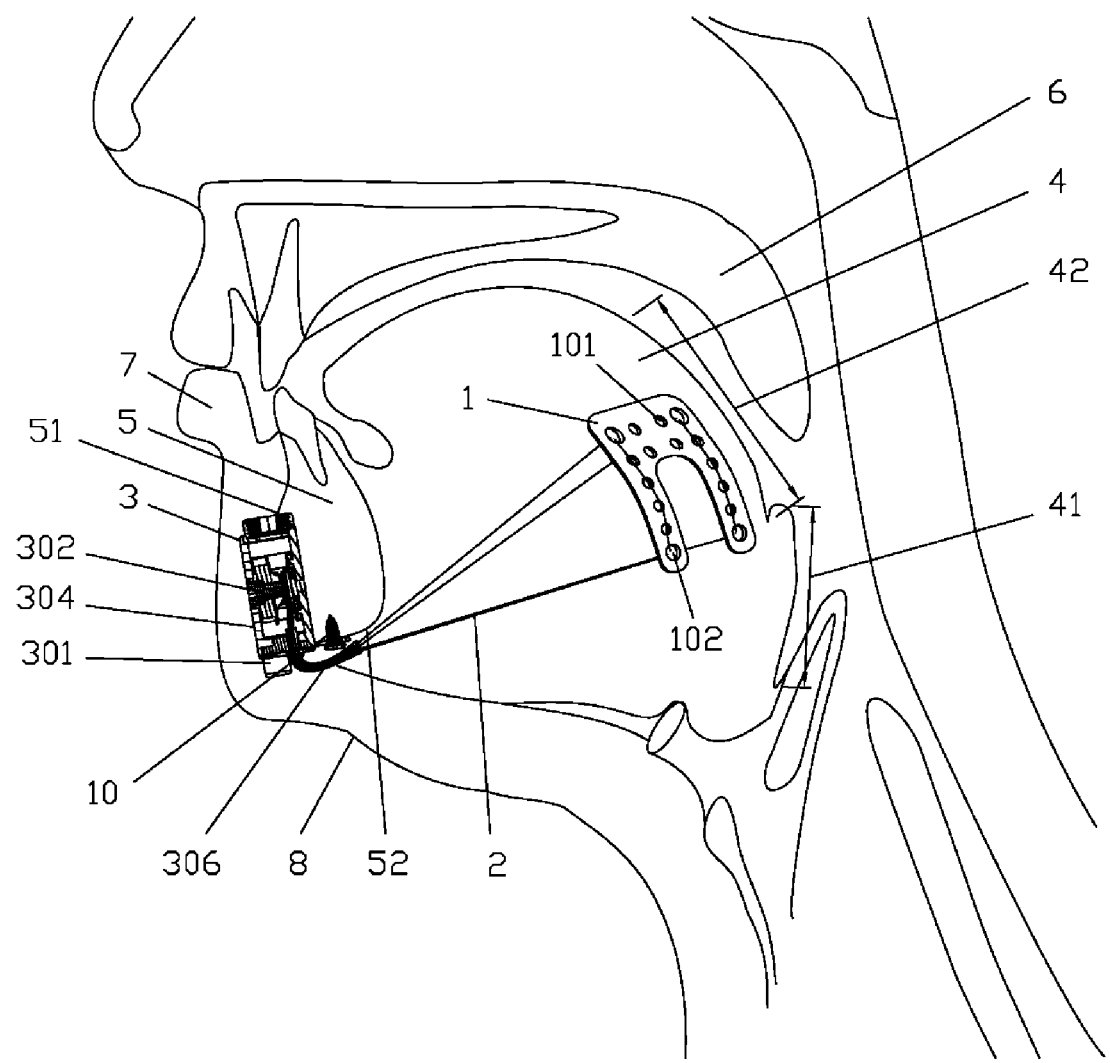
FIG. 1 is a schematic structural view of a tongue pulling device implanted into the mandible and the tongue body according to the present invention.
Figure 28B:
Figure 28C:
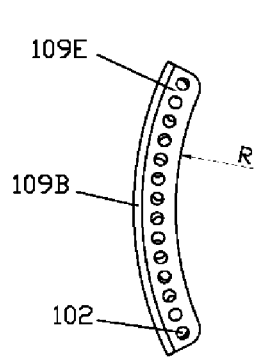
Figure 28A:
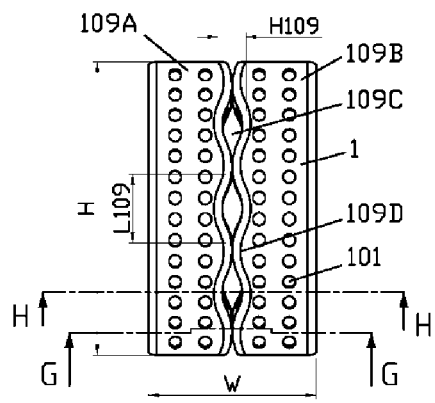
Figure 28D:
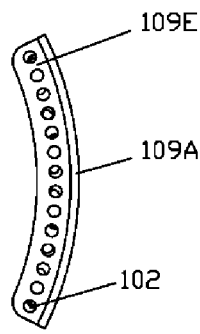
Figure 28E:
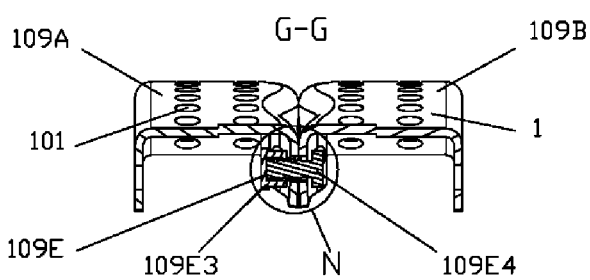
Figure 28F:
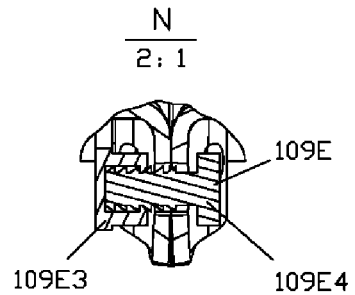
Figure 28F:
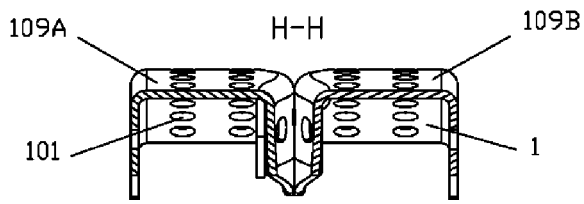
Figure 28G:
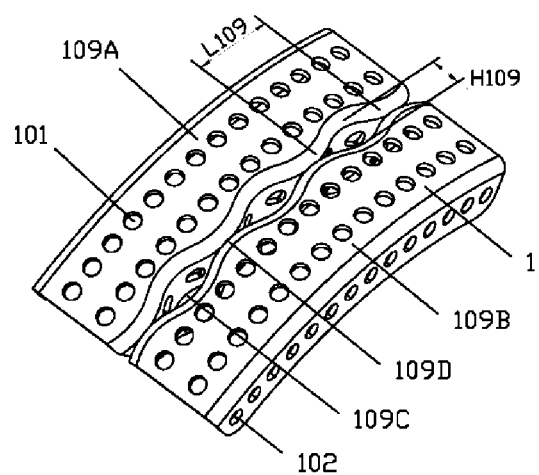
Figure 28H:
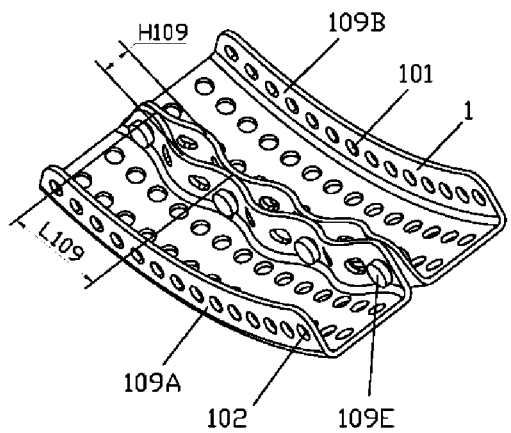
Figure 28I:
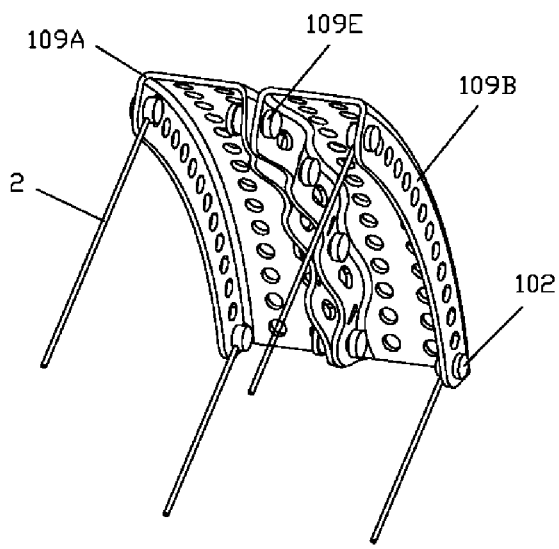
Figure 28J:
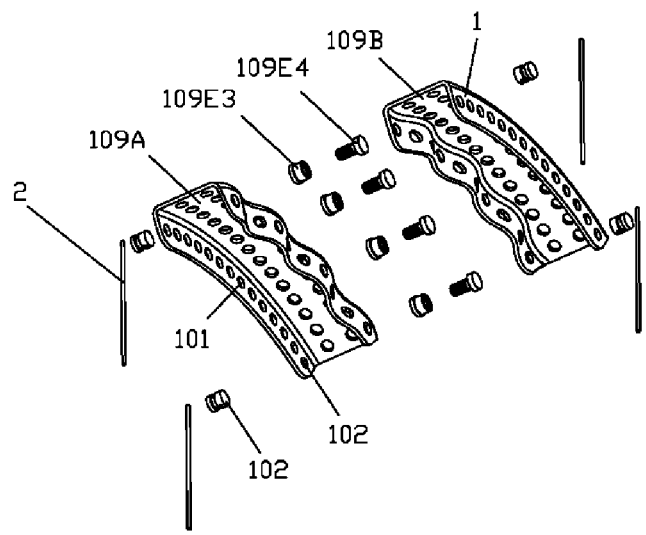
Figure 28K:
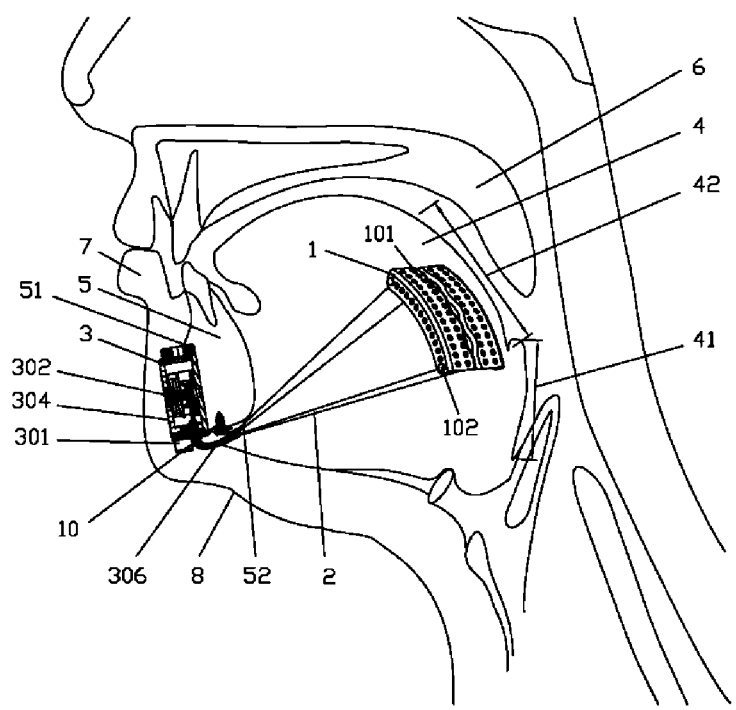
Figure 29:
Figure 30A:
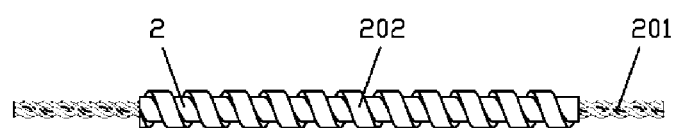
Figure 30B:
Figure 31A:
Figure 31B:
Figure 32:

FIG. 28E1 is an enlarged view of part N of FIG. 28E;

FIG. 28F is an H-H cross-sectional view of FIG. 28A;

FIG. 28G is a three-dimensional schematic structural view of FIG. 28A;

FIG. 28H is a three-dimensional schematic structural view of the back side of FIG. 28G;

FIG. 28I is a schematic structural view of the combined-type pull plate of FIG. 28G mounted with pull lines;

FIG. 28J is an exploded view of FIG. 28I;

FIG. 28K is a view depicting the working principle of a tongue pulling device using the U-shaped combined-type pull plate according to the present invention;

FIG. 29 is a schematic structural view of a pull line formed by braiding multiple metal wires according to the present invention;

FIG. 30A is a schematic structural view of a composite pull line of a continuous corrugated tube type according to the present invention;

FIG. 30B is a schematic structural view of a composite pull line of a discontinuous corrugated tube type according to the present invention;

FIG. 31A is a schematic structural view of a composite pull line of a continuous spiral tube type according to the present invention;

FIG. 31B is a schematic structural view of a composite pull line of a discontinuous spiral tube type according to the present invention;

FIG. 32 is a schematic structural view of a pull line of a titanium metal bead type according to the present invention.

THE MEANINGS OF THE SERIAL NUMBERS IN THE ABOVE DRAWINGS ARE AS FOLLOWS 1. pull plate, 2. pull line, 3. retractor, 4. tongue, 5. mandible, 6. soft palate, 7. lower lip, 8. skin, 9. screwdriver, 10. Screw, 11. human tissues, 12. hyoid hone, 13. special surgical forceps, 41. tongue base, 42. tongue dorsum, 51. front portion of mandible, 52. bottom portion of mandible 101. through hole for facilitating growth of fibrous tissues, 102. pull line fixing mechanism, 103. frame of pull plate, 104. medical film, 105. gap between the films, 106. bonded part or bonded edge, 107. coating for improving biocompatibility, 108. U-shaped node 102A. small bump, 102B. small groove, 102C. rivet fastening mechanism, 102D. thread fastening mechanism 103A. position of frame before movement, 103B. position of frame after movement, 103C. elastic wire 109A. left-side pull plate, 109B. right-side pull plate, 109C. gap between left-side pull plate and the right-side pull plate, 109D. junction between the left-side pull plate and the right-side pull plate, 109E. mechanical connection mechanism, 109E1. rivet, 109E2. rivet base, 109E3. lock nut for concave-convex engagement, 109E4. lock screw for concave-convex engagement H109. maximum width of the gap between left-side pull plate and the right-side pull plate, L109. maximum length of the gap between the left-side pull plate and the right-side pull plate 201. draw line, 202. Sleeve, 202A. inner layer, 202B. outer layer, 203. bead 301. control switch, 302. pull line fixing device, 303. anti-cutting buffer device, 304. retractor casing, 305. restoring spring, 306. protective sheath 301A. positioning convex step of control switch, 301B. positioning concave groove of control switch, 301C. tightening switch, 301D. loosening switch, 301E. spring, 301F. adjustment handle, 301G. spring positioning post, 301A1. convex gear, 301B1. concave gear, wedge-shaped slide block (301A 1) on the tightening switch, spring (301E1) on the tightening switch, wedge-shaped slide block (301A2) on the tightening switch, the spring (301E2) on the tightening switch, 301B2. ratchet, 301B3. tooth rack

302A. thread hole, 302B. positioning slot, 302C. binding plate, 302D. spring positioning post, 302E. positioning convex step, 302F. positioning convex step connected to 301, 302G. positioning convex step connected to 301, 302H. spring, 302I. pull line fixing bolt, 302J. internal thread, 302L. bobbin, 302M. positioning slide block, 302M1. positioning slide-block cover

304A. thread hole, 304B. seal ring, 304C. screw hole, 304D. silica gel plug, 304E. positioning convex step, 304F. positioning concave groove, 304G. top cover, 304H. bottom cover of the casing, 304I. nut, 304J. screw, 304K. silica gel film, 304L. main body, 304M. side surface of the casing, 304N. side hole, 304P. positioning slot opening, 304B1. top cover seal ring, fixing plate (304B2) of the top cover seal ring, 304L1. casing side plate, 304A1. through hole (304A1) on the nut

305A. fixed head of restoring spring, 305B. positioning slot for the fixed head of restoring spring

C. clearance, H. height, H1. height, R. radian, T. thickness, W. width, $\varphi$. diameter of through hole.

DETAILED DESCRIPTION OF THE INVENTION

Embodiment 1: A Tongue Pulling Device of the Present Invention

Referring to FIG. 1, this embodiment shows the basic structure of a tongue pulling device of the present invention.

The tongue pulling device of the present invention includes a pull plate (1), a pull line (2), and a retractor (3). The pull plate (1) is a flat implant capable of being implanted under the mucous membrane layer of the tongue base portion and/or the tongue dorsum portion of a human body, and includes through holes (101) allowing growth and penetration of human tissues and pull line fixing mechanisms (102). The pull line (2) is a thread made of a material capable of being implanted into the human body for a long term. The retractor (3) includes a control switch (301) capable of adjusting a tension of the pull line (2), a pull line fixing mechanism (302), and a casing (304). The pull line (2) has one end connected to the pull plate (1) and the other end connected to the retractor (3).

In this embodiment, the pull plate (1) is implanted into the muscular layer under the mucous membrane layer of the tongue dorsum portion. The retractor (3) is fixed to the mandible (5) by using a screw (10).

In this embodiment, the pull line fixing mechanisms (102) are through holes for winding and fixing the pull line (2).

In this embodiment, the pull plate (1) is retracted by using a four-line four-corner spatial positioning method, that is, by using four pull lines (2), where one end of each of the four pull lines is fixed to a corresponding one of the pull line fixing mechanisms (102) at four corners of the pull plate (1), and the other end of each of the four pull lines is passed through the protective sheath (306) and fixed to the retractor (3), so as to achieve three-dimensional fixing.

Since the pull plate (1) has a spatial curved surface matching with the shape of the tongue base portion and/or the tongue dorsum portion, the tongue body is retracted in a surface contact manner, so that the pressure generated by retracting the tongue base portion and/or the tongue dorsum portion is greatly reduced, thereby preventing the pull plate (1) from cutting the tongue muscles under long-term alternate tensions. The pressure generated by the tension on the pull plate (1) may be smaller than 1000 g/cm$^2$, for example, under a tension of 3000 g, if the pressure generated by the tension on the pull plate (1) needs to be smaller than 500 g/cm$^2$, the area of the pull plate (1) only needs to be larger than 6 cm$^2$, that is, the pull plate (1) only needs to be a 25 mm×25 mm square.

Figure 22A:
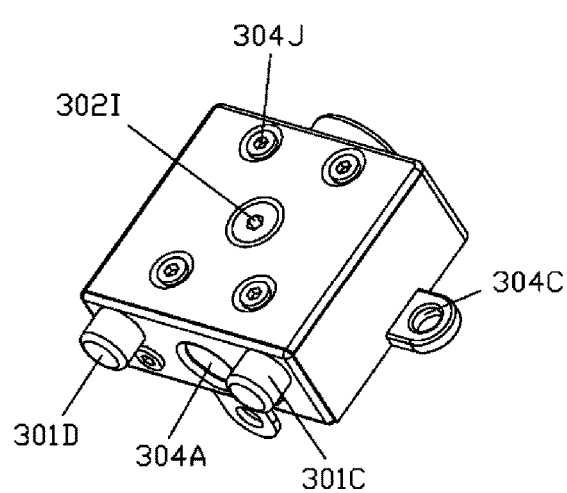
FIG. 22A is a three-dimensional view of a double-button ratchet-type retractor according to the present invention.
Figure 22B:
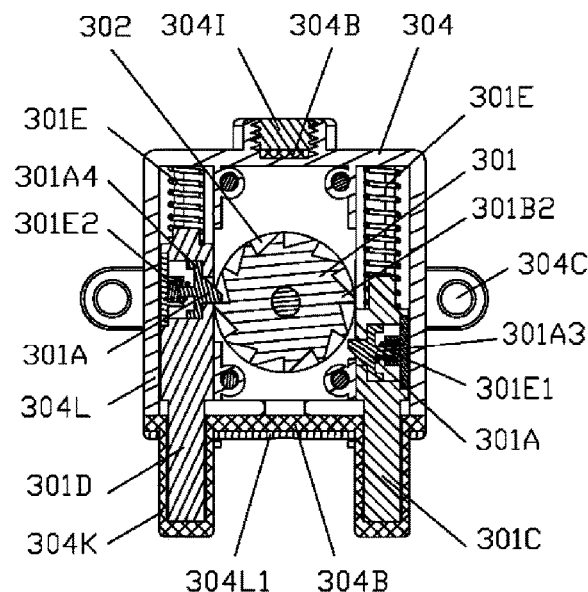
FIG. 22B is a schematic structural view of the retractor of FIG. 22A.
Figure 22C:
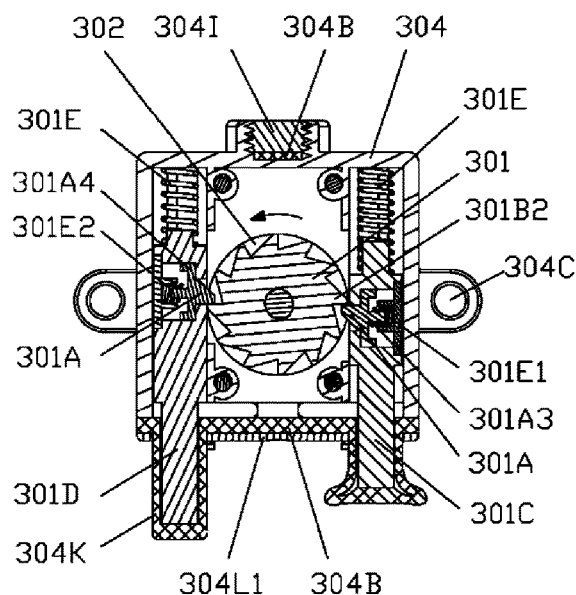
FIG. 22C is a view depicting the working principle of the retractor of FIG. 22A when the tightening switch pressed.
Figure 22D:
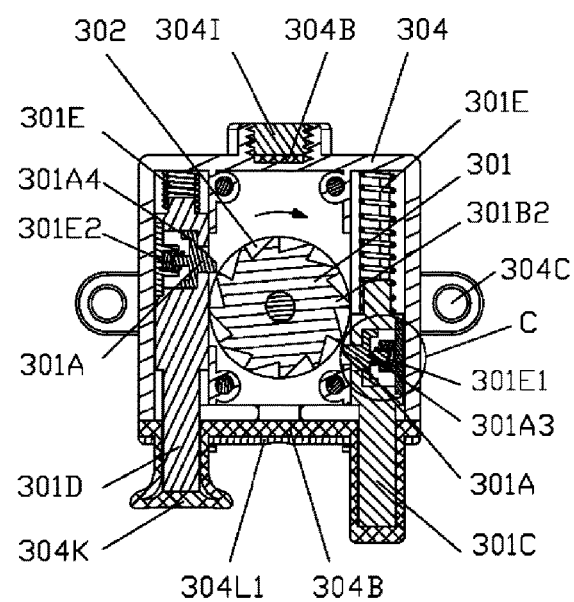
FIG. 22D is a view depicting the working principle of the retractor of FIG. 22A when the loosening switch pressed.
Figure 22E:
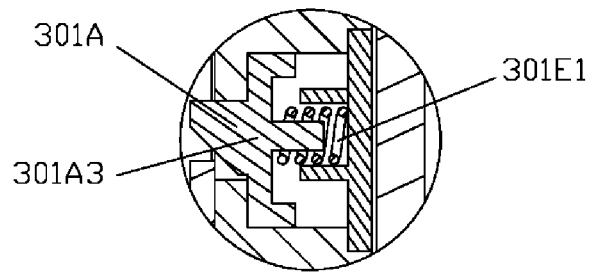
FIG. 22E is a longitudinal cross-sectional view of FIG. 22A.
Figure 22E:
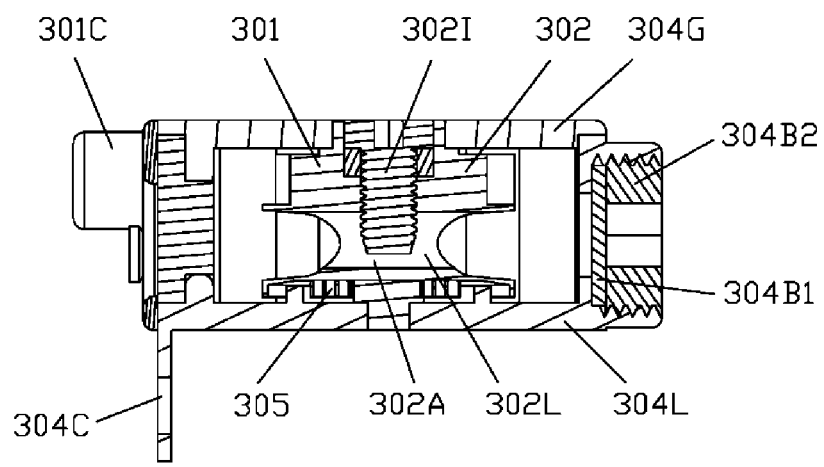
Figure 22F:
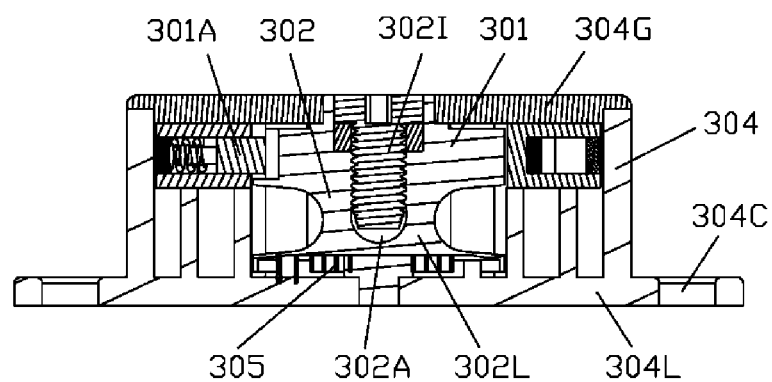
FIG. 22F is a transversal cross-sectional view of FIG. 22A.
Figure 22G:
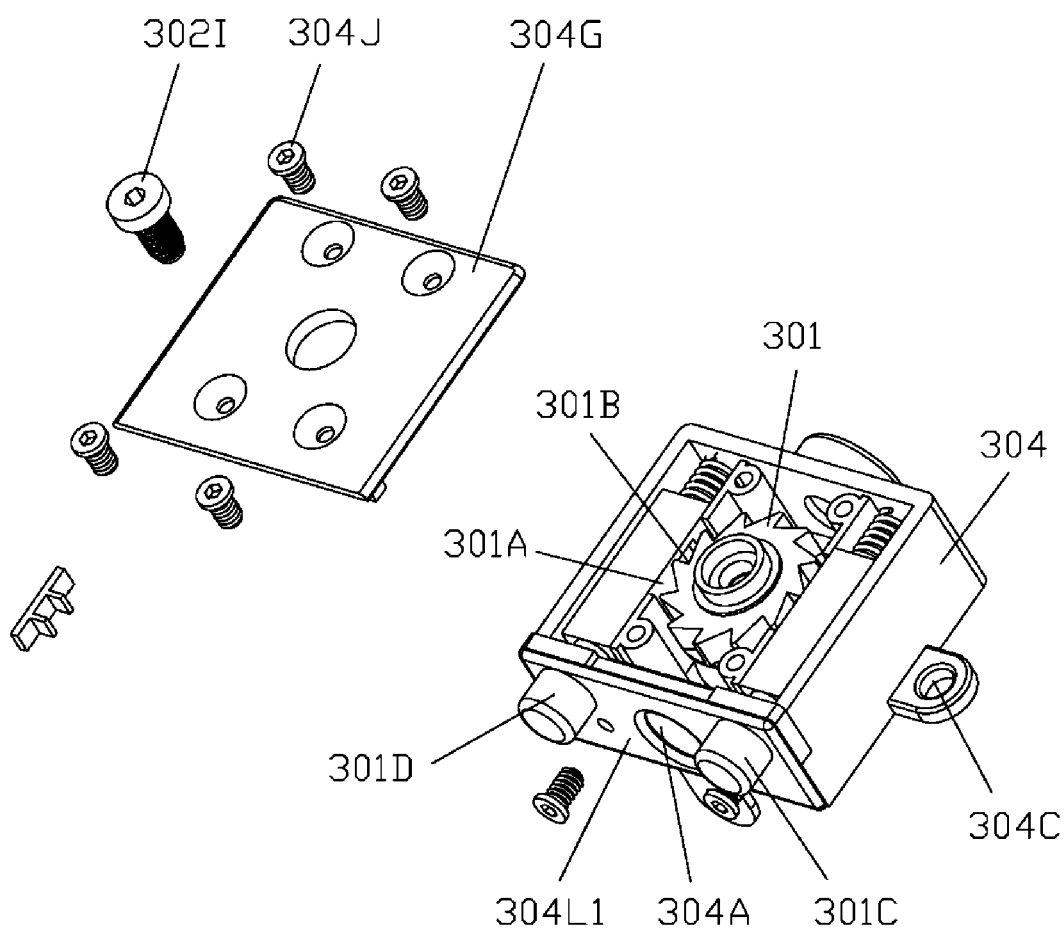
FIG. 22G is an exploded view showing the structure of the ratchet and the control switch.
Figure 22H:
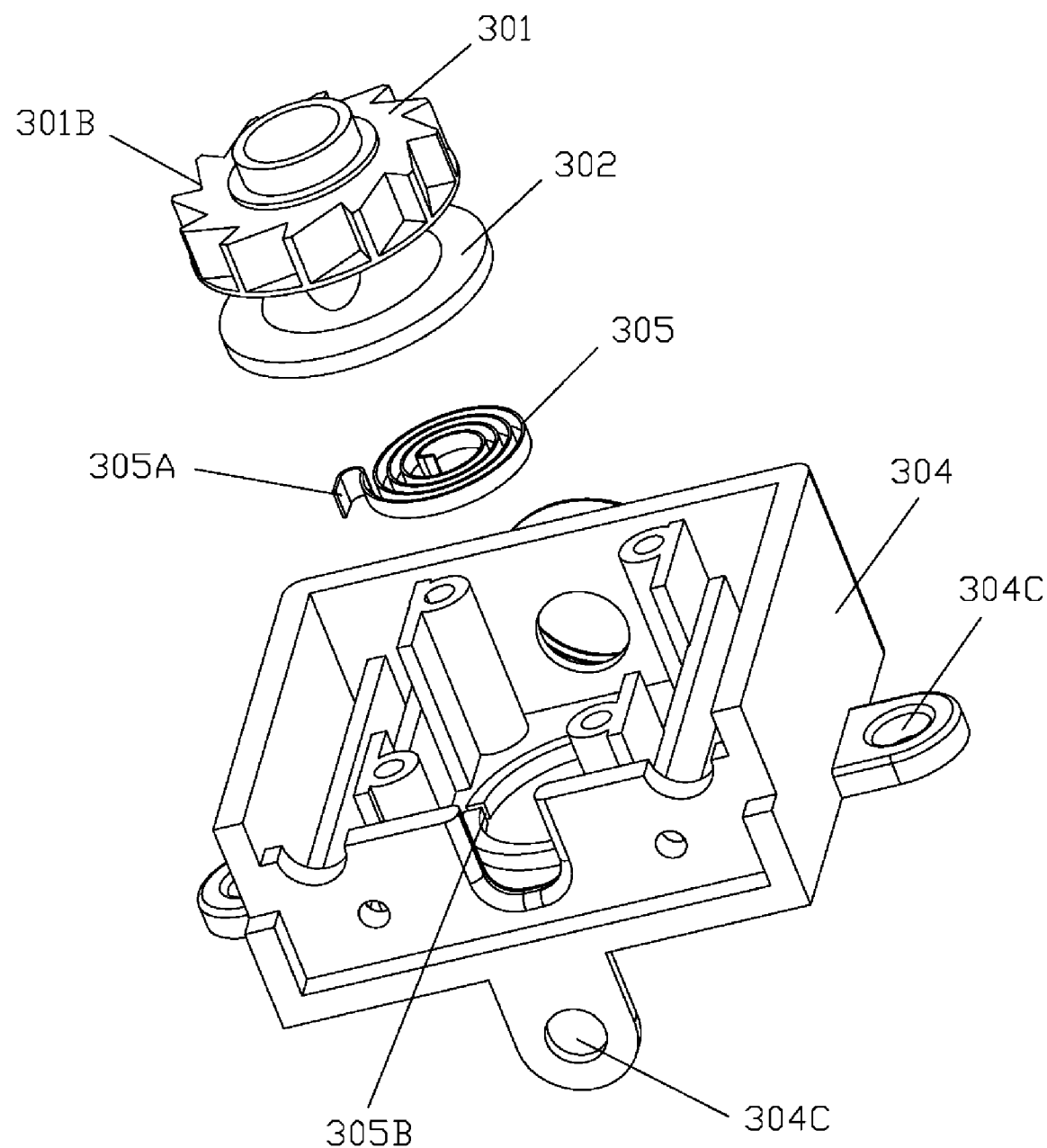
FIG. 22H is an exploded view showing the structure of the ratchet and the restoring spring.
Figure 22I:
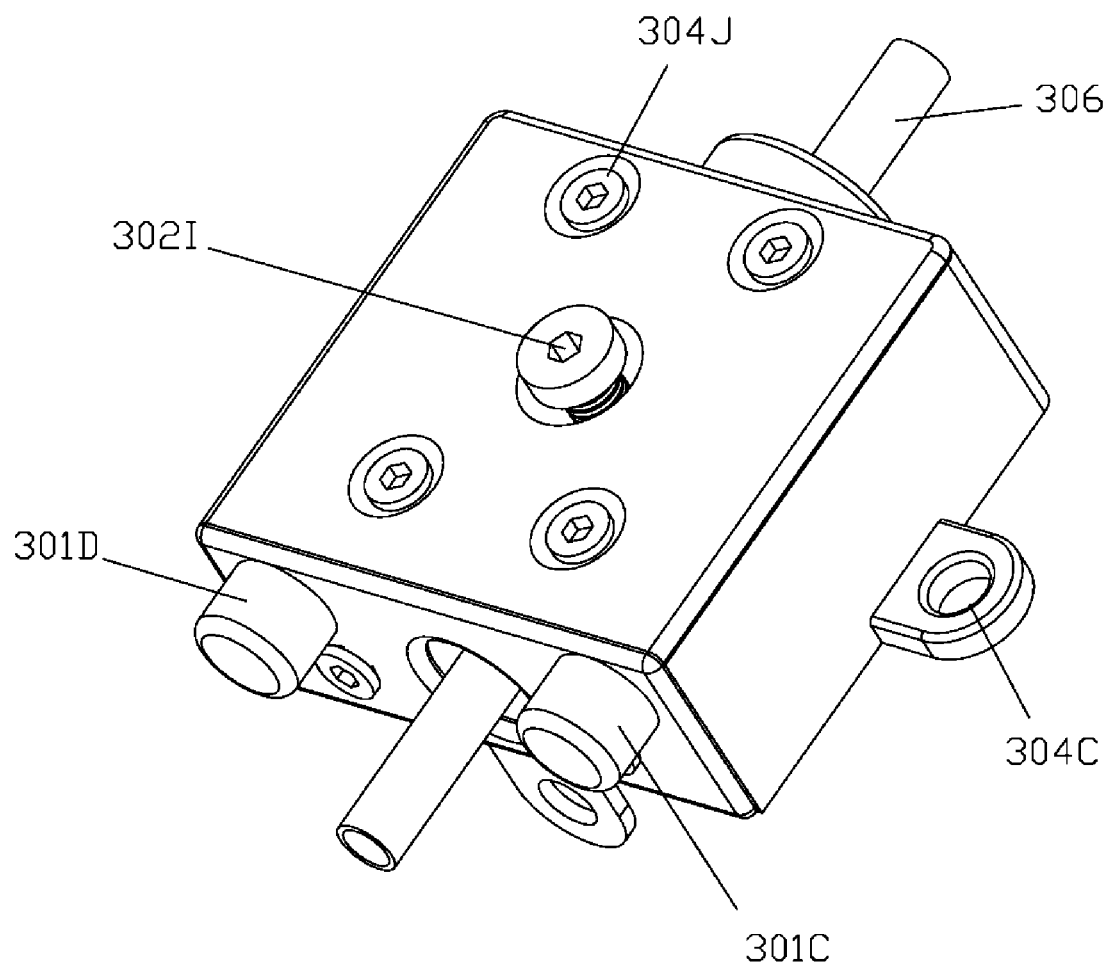
FIG. 22I is a three-dimensional view of a button-type retractor that has a protective sheath and can be adjusted after surgery according to the present invention.
Figure 22J:
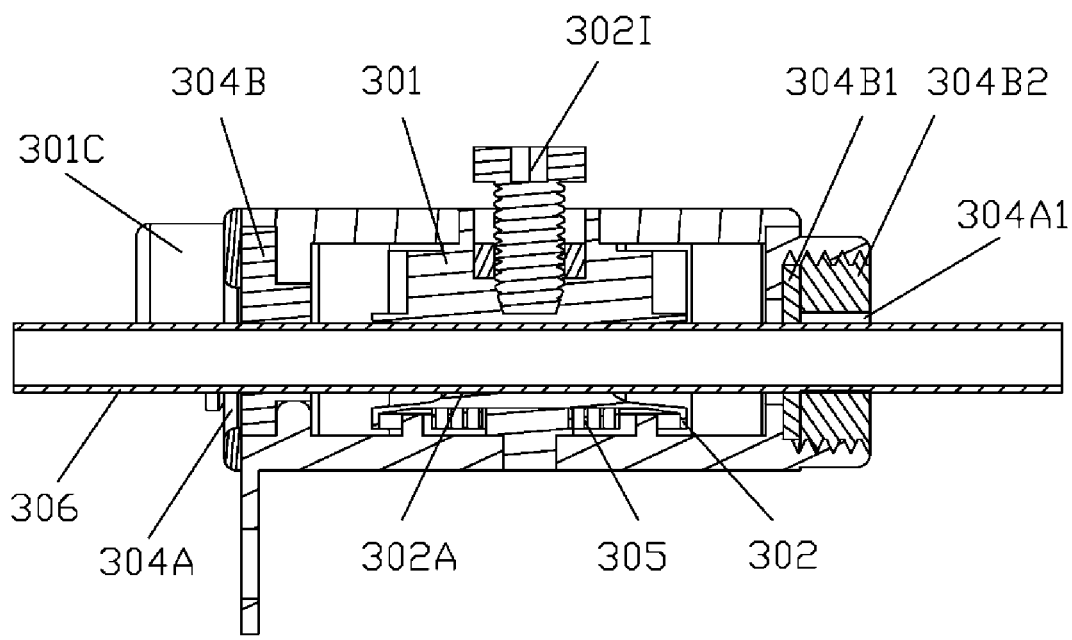
FIG. 22J is a longitudinal cross-sectional view of FIG. 22I.
Figure 22K:
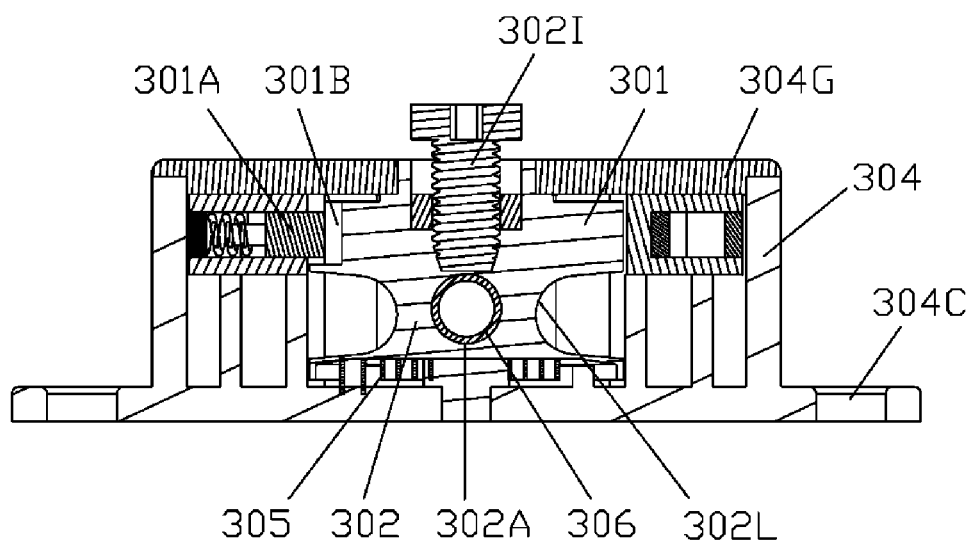
FIG. 22K is a transversal cross-sectional view of FIG. 22A.
Figure 22L:
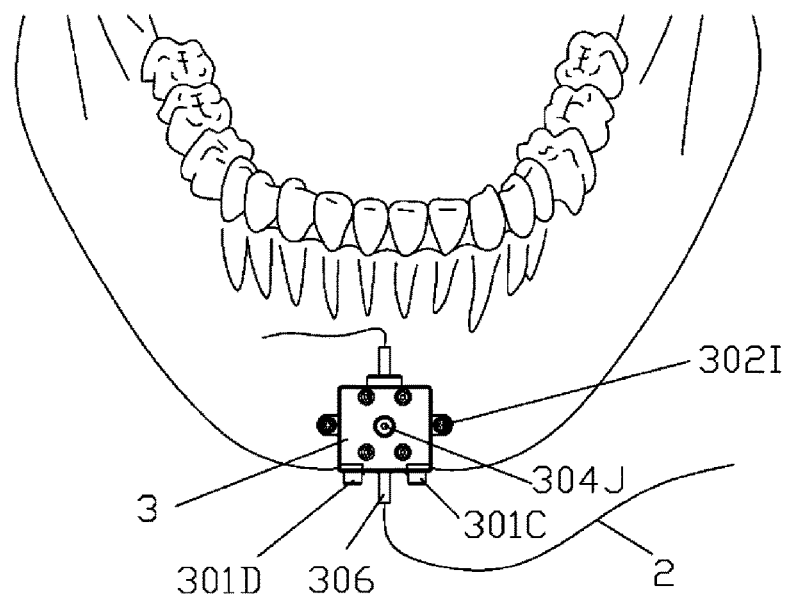
FIG. 22L is a mounting view of a button-type retractor that can be adjusted after surgery in a tongue pulling device according to the present invention.
Figures 22M, 22N:
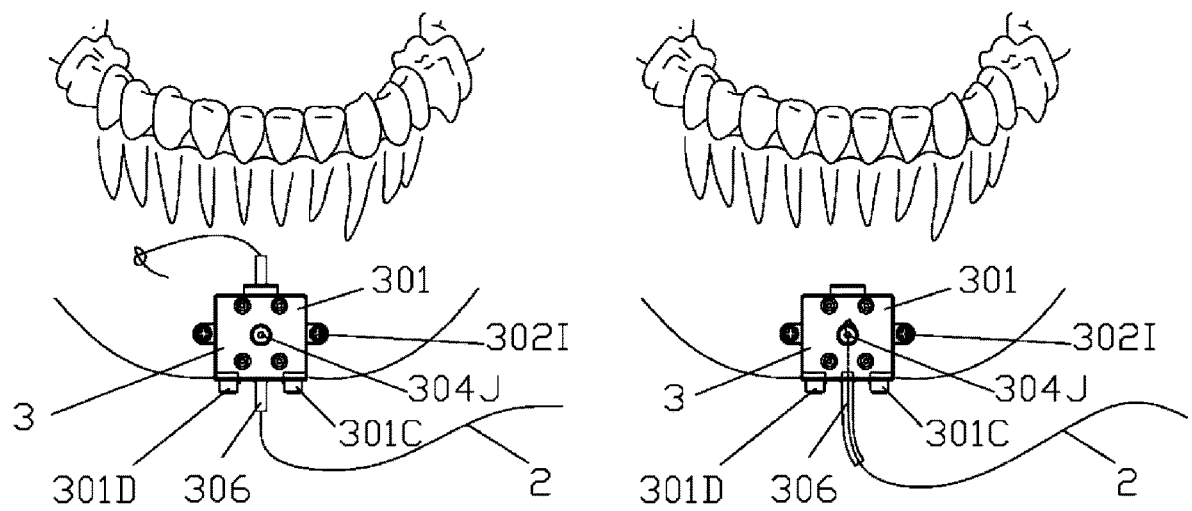
FIG. 22M is a mounting view of a button-type retractor that can be adjusted after surgery in a tongue pulling device according to the present invention.
FIG. 22N is a mounting view of a button-type retractor that can be adjusted after surgery in a tongue pulling device according to the present invention.
Figure 22P:
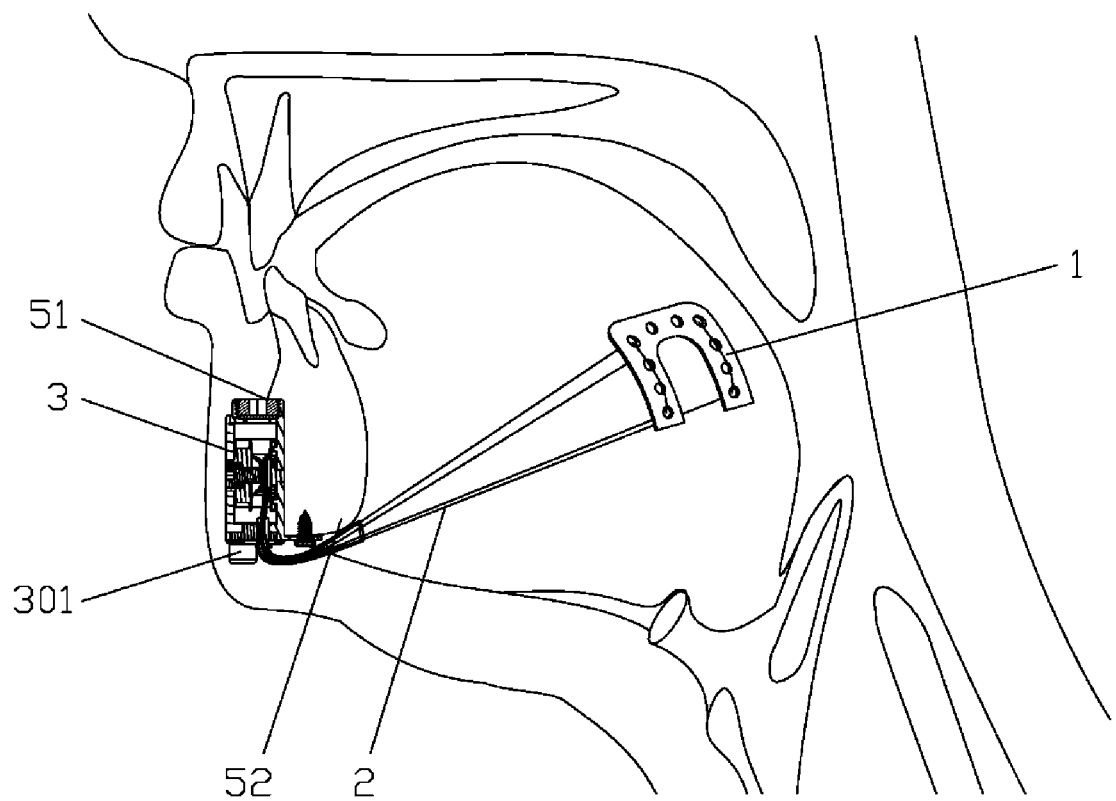
FIG. 22P is a view depicting the working principle.
Figure 22Q:
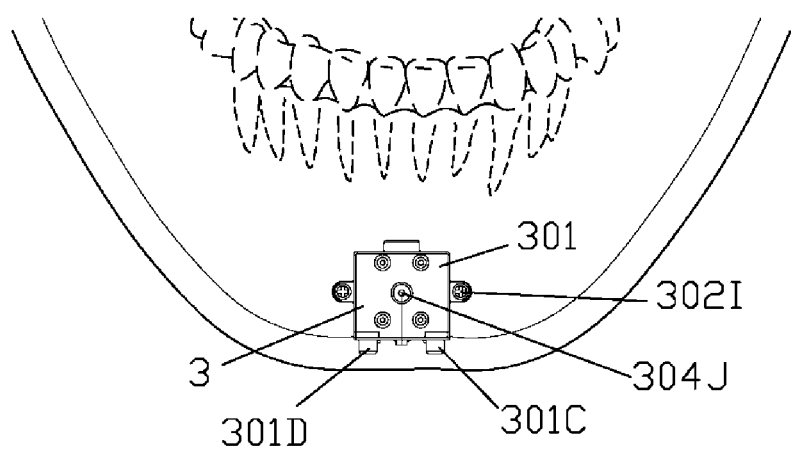
FIG. 22Q is a view depicting the working principle.
Figure 23A:
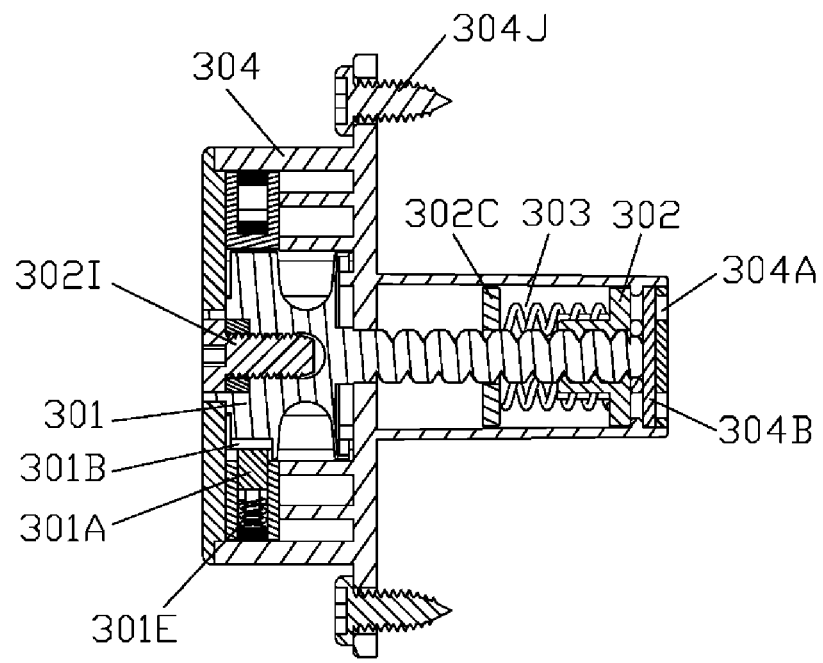
FIG. 23A is a schematic structural view of a double-button ratchet thread-type retractor according to the present invention.
Figure 23B:
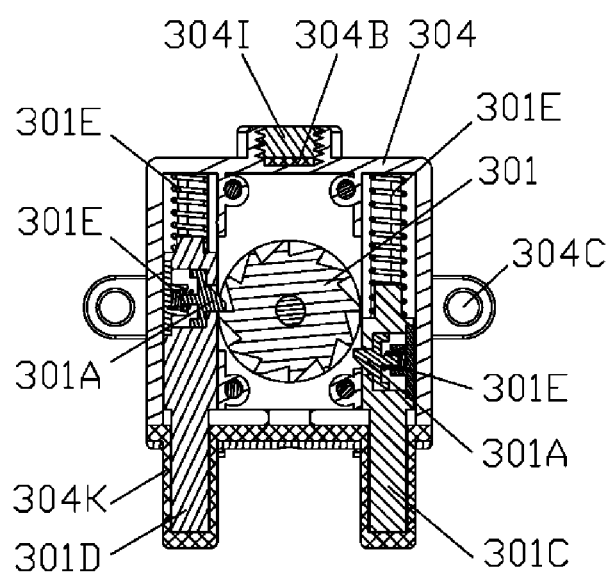
FIG. 23B is a schematic structural view of the retractor of FIG. 23A.
Figure 23C:
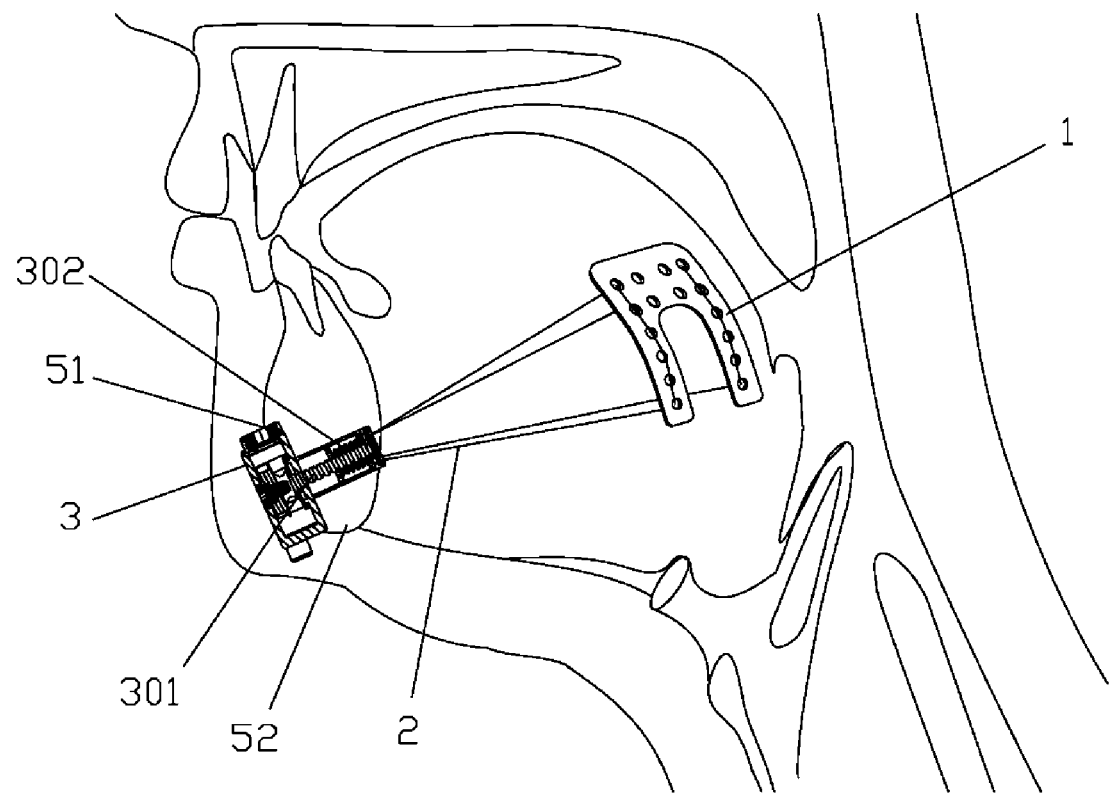
FIG. 23C is a view depicting the working principle of the retractor of FIG. 23A.
Figure 23D:
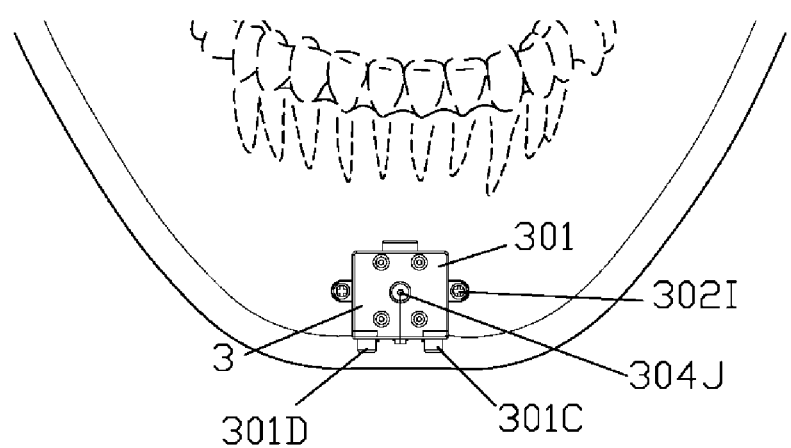
FIG. 23D is a view depicting the working principle of the retractor of FIG. 23A.

After the tongue pulling device of the present invention is implanted through surgery, the patient can adjust the pulling degree of the tongue pulling device of the present invention to the tongue base portion and/or the tongue dorsum portion under the instruction of the doctor, so as to achieve maximum comfort, as shown in FIG. 22A to FIG. 22Q.

Particularly, in a non-sleep state, the control switch (301) is pressed from a position outside the skin (8) of the mandible to loosen the pull lines (2), so as to increase the length of the pull lines (2) between the pull plate (1) and the retractor (3), so that the pull lines (2) apply a small pulling force to the tongue base portion and/or the tongue dorsum portion or are completely in a loosened state, and at this time, the movement of the tongue is almost unconstrained, and the tongue is capable of moving freely during speaking, swallowing and other activities, thereby ensuring free movement of the tongue during speaking, swallowing and other activities.

Before sleep, the control switch (301) is pressed from the position outside the skin (8) of the mandible to tighten the pull lines (2), so as to reduce the length of the pull lines (2) between the pull plate (1) and the retractor (3), and at this time, the pull line (2) applies a large pulling force to the tongue base portion and/or the tongue dorsum portion, the tongue base portion and/or the tongue dorsum portion is in an effective retracted state, and the tongue base portion and/or the tongue dorsum portion is pulled forward, so as to maintain the palatopharyngeal portion open, thereby preventing OSAHS.

A degree of comfort may also be set for the tongue pulling device of the present invention. To avoid daily adjustment, the control switch (301) may be adjusted so that the pull line (2) applies a proper pulling force to the tongue base portion and/or the tongue dorsum portion, so as to move the tongue base portion and/or the tongue dorsum portion forward while ensuring comfort during movement of the tongue, and maintain the palatopharyngeal portion open, thereby preventing OSAHS.

Figure 2:
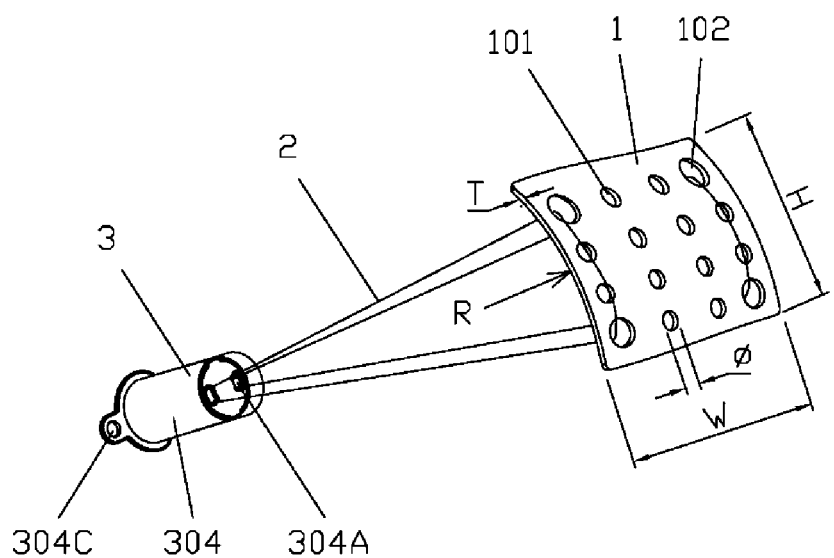
FIG. 2 is a schematic structural view of a tongue pulling device having a rectangular pull plate according to the present invention.

Embodiment 2: A Tongue Pulling Device Having a Rectangular Pull Plate of the Present Invention Referring to FIG. 2, in this embodiment, the pull plate (1) adopts a rectangular spatial curved plate structure.

Main dimensions of the rectangular pull plate (1) include:

a radian R of the curved surface being 10 mm to 120 mm, and preferably 20 mm to 50 mm;

a width W of the curved surface being 10 mm to 50 mm, and preferably 15 mm to 30 mm;

a height H of the curved surface being 10 mm to 50 mm, and preferably 20 mm to 35 mm;

a thickness T of the plate being 0.1 mm to 1 mm, and preferably 0.4 mm to 0.8 mm; and a diameter $\varphi$ of the through hole (101) being 0.1 mm to 4 mm, and preferably 0.5 mm to 2 mm.

Typical dimensions (width×height) include: 15 mm×20 mm, 18 mm×25 mm, 20 mm×30 mm, 25 mm×35 mm, 30 mm×35 mm, 35 mm×35 mm, 35 mm×40 mm, 40 mm×40 mm and the like.

The pull plate (1) is made of a material selected from a group consisting of, but not limited to: medical metal materials, medical polymer materials, medical composite materials, metal amorphous materials (also referred to as metallic glass) for medical use, and various modified coating materials. Specific materials are generally selected from a group consisting of:

medical grade pure titanium, medical grade titanium alloy, Ti—Zr—Ta alloy, Co—Cr—W alloy, titanium-nickel shape memory alloy (Nitinol alloy), Ti-based amorphous materials, Zr-based amorphous materials, Fe-based amorphous materials, medical grade stainless steel (such as 316L), various medical grade titanium and titanium alloy with an amorphous material coating and medical grade stainless steel with an amorphous material coating, and the like.

Medical grade PA, medical grade PC, medical grade PE, medical grade PU, medical grade PP, medical grade polytetrafluoroethylene and other medical polymer materials and fiber reinforced composite materials.

Figure 3:
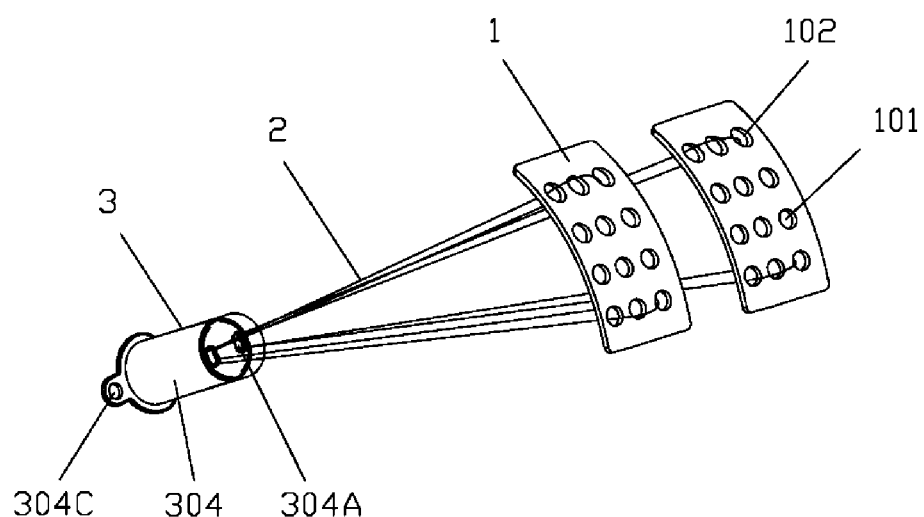
FIG. 3 is a schematic structural view of a tongue pulling device using two pull plates according to the present invention.

Embodiment 3: A Tongue Pulling Device Using Two Pull Plates of the Present Invention Referring to FIG. 3, the basic principle of this embodiment is similar to that of Embodiment 2 shown in FIG. 2. The difference lies in that: two the pull plates (1) are used, which are mounted on left and right sides of the tongue base portion and/or the tongue dorsum portion, and disposed into the muscular layer under the mucous membrane layer, where each of the pull plates (1) is fixed by using four pull lines (2), and therefore, a total of eight pull lines are used.

Figure 4:
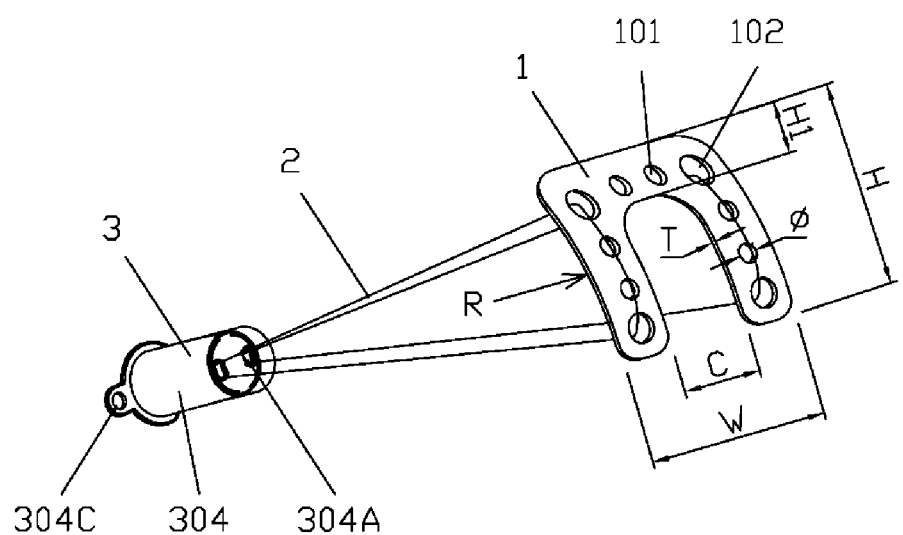
FIG. 4 is a schematic structural view of a tongue pulling device having a U-shaped pull plate according to the present invention.

Embodiment 4: A Tongue Pulling Device Having a U-Shaped Pull Plate of the Present Invention Referring to FIG. 4, the basic principle of this embodiment is similar to that of Embodiment 2 shown in FIG. 2. The difference lies in that: the pull plate (1) adopts a U-shaped structure, and the pull plate (1) of the U-shaped structure is particularly suitable for retracting the tongue dorsum portion and the junction between the tongue dorsum portion and the tongue base. The pulling of the tongue dorsum portion and the junction between the tongue dorsum portion and the tongue base is an effective means for enlarging the palatopharyngeal portion to prevent OSAHS.

Main dimensions of the U-shaped pull plate (1) include:

a radian R of the curved surface being 10 mm to 120 mm, and preferably 20 mm to 50 mm;

a width W of the curved surface being 10 mm to 50 mm, and preferably 15 mm to 30 mm;

a height H of the curved surface being 10 mm to 50 mm, and preferably 20 mm to 35 mm;

a height H1 being 5 mm to 20 mm, and preferably 5 mm to 15 mm;

a clearance C of the curved surface being 6 mm to 15 mm, and preferably 5 mm to 10 mm;

a thickness T of the plate being 0.1 mm to 1 mm, and preferably 0.4 mm to 0.8 mm; and a diameter φ of the through hole (101) being 0.1 mm to 4 mm, and preferably 0.5 mm to 3 mm.

The U-shaped pull plate (1) is generally made of a medical metal material, particularly, medical grade pure titanium, medical grade titanium alloy, Ti—Zr—Ta alloy, Co—Cr—W alloy, a Ti-based amorphous material, a Zr-based amorphous material, a Fe-based amorphous materials, medical grade stainless steel (such as 316L), medical grade stainless steel with an amorphous material coating, or the like.

Figure 5:
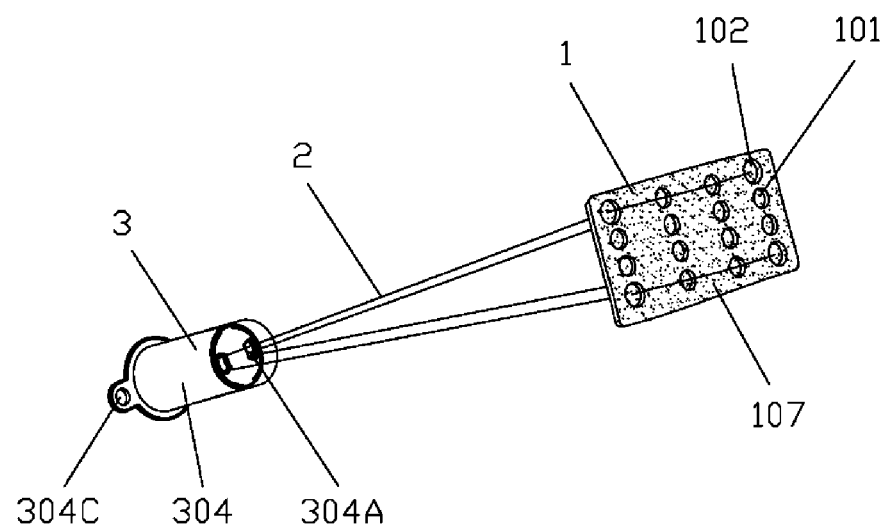
FIG. 5 is a schematic structural view of a tongue pulling device having a coating according to the present invention.

Embodiment 5: A Tongue Pulling Device Having a Coating of the Present Invention Referring to FIG. 5, the basic principle of this embodiment is similar to that of Embodiment 2 shown in FIG. 2. The difference lies in that: the pull plate (1) has a coating (107). The coating (107) has higher biocompatibility than that of the substrate material. For example, when the material of the pull plate (1) is 316L stainless steel, a pure titanium metal coating may be manufactured on the surface of a 316L stainless steel substrate by plasma spraying or magnetron sputtering. Since pure titanium metal has higher biocompatibility than that of 316L stainless steel, the growth and penetration of fibrous tissues of the human body are made easier.

Particularly, the coating (107) on the surface of the pull plate (1) may be manufactured into a Ti-based amorphous coating by magnetron sputtering. The Ti-based amorphous coating has excellent biocompatibility, and can form a firm bond with human tissues.

Figure 6:
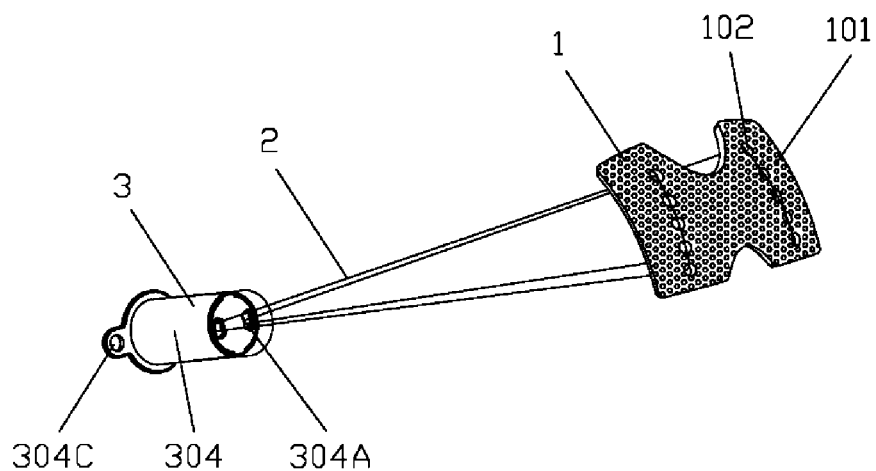
FIG. 6 is a schematic structural view of a tongue pulling device having an H-shaped pull plate according to the present invention.

Embodiment 6: A Tongue Pulling Device Having an H-Shaped Pull Plate of the Present Invention Referring to FIG. 6, the difference of this embodiment lies in that: the pull plate (1) adopts an H-shaped structure, that is, the geometrical shape of the pull plate (1) is similar to an H-shape. The pull plate (1) includes tiny through holes (101) facilitating growth of tissues, and the through holes (101) have a diameter of smaller than 1 mm. The pull plate (1) further includes pull line fixing mechanisms (102), and the pull line fixing mechanisms (102) are through holes having a diameter of 2 mm to 3 mm.

Moreover, the pull plate (1) is made of a medical polymer material.

Since the medical polymer material has a lower specific gravity than that of a medical metal material, the pull plate (1) made of the medical polymer material is lighter, and is more suitable for being implanted into the tongue dorsum portion and/or the tongue base portion.

The medical polymer material is generally selected from a group consisting of: materials such as polyamide (PA), polycarbonate (PC), polyurethane (PU), polyethylene/polythene (PE), polypropylene (PP) and medical grade polytetrafluoroethylene, and fiber reinforced composite materials such as fiber reinforced PC, fiber reinforced PE, fiber reinforced PU, fiber reinforced PP and fiber reinforced PA.

Figure 7:
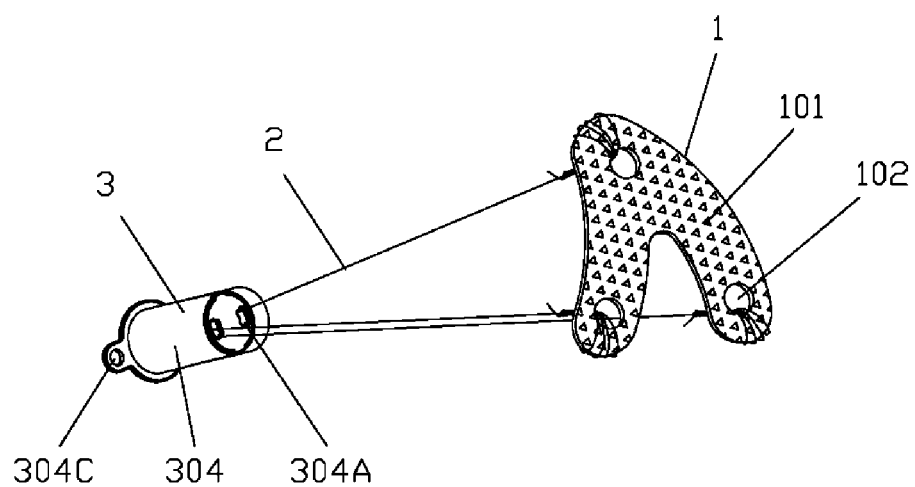
FIG. 7 is a schematic structural view of a tongue pulling device having a V-shaped pull plate according to the present invention.

Embodiment 7: A Tongue Pulling Device Having a Y-Shaped Pull Plate of the Present Invention Referring to FIG. 7, the difference of this embodiment lies in that: the pull plate (1) adopts a V-shaped structure, that is, the geometrical shape of the pull plate (1) is similar to a V-shape. The pull plate (1) includes tiny through holes (101) facilitating growth of tissues, and the through holes (101) have a diameter of smaller than 1 mm. The pull plate (1) further includes pull line fixing mechanisms (102), and the pull line fixing mechanisms (102) are through holes having a diameter of 2 mm to 3 mm. In this embodiment, there are a total of three through holes serving as the pull line fixing mechanisms (102).

Three-line positioning method. In this embodiment, the three-line positioning method is adopted, that is, three pull lines (2) are used to spatially position the pull plate (1). One of the pull lines (2) is bound to the through hole that serves as the pull line fixing mechanism (102) at the top of the V-shaped pull plate (1), and the other two pull lines (2) are respectively bound to the two through holes that serve as the pull line fixing mechanisms (102) at the bottom of the V-shaped pull plate (1); the other end of each of the three pull lines (2) is fixed to the retractor (3), so as to spatially position the pull plate (1).

The pull plate (1) may be made of a high-strength medical polymer fiber braid. The high-strength polymer fiber braid is, for example, polypropylene fiber braided fabric, which not only has high strength, but also is light in weight, and therefore is suitable for manufacturing the pull plate (1). In this embodiment, the pull plate (1) is made of the polypropylene fiber braided fabric. The fiber braided fabric has many tiny holes, which may function as the tiny through holes (101) for facilitating growth of tissues, and it only needs to form through holes as the pull line fixing mechanisms (102).

Different structural designs of the pull line fixing mechanisms (102)

Figure 7A:
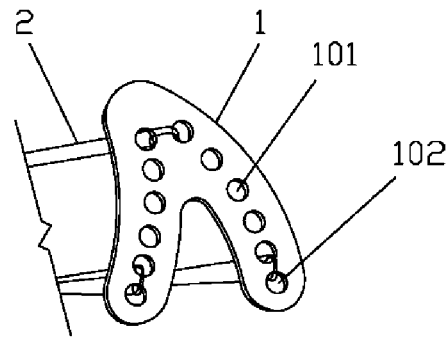
FIG. 7A is a schematic structural view of pull lines wound on pull line fixing mechanisms of a through-hole type according to the present invention.
Figure 7B:
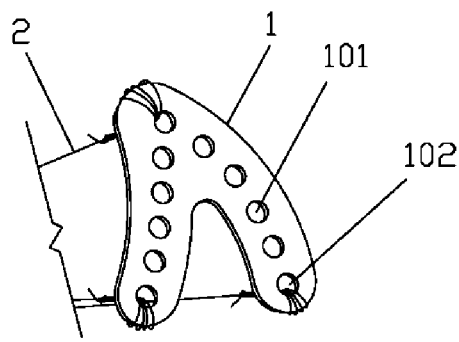
FIG. 7B is a schematic structural view of pull lines bound on pull line fixing mechanisms of a through-hole type according to the present invention.

Referring to FIG. 7A to FIG. 7B, the pull line fixing mechanisms (102) may be designed into different specific structures.

The most common structure of the pull line fixing mechanisms (102) is a through hole structure, which not only facilitates winding the pull lines, but also facilitates binding and fixing the pull lines. Referring to FIG. 7A, the pull lines (2) are wound to the through holes (102) serving as the pull line fixing mechanisms for two turns and then pulled back. Referring to FIG. 7B, the pull lines (2) are bound, tied, and fixed to the through holes (102).

Figure 7C:
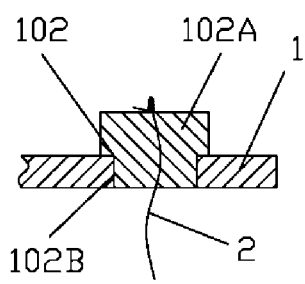
FIG. 7C is a schematic structural view of pull lines fixed to pull line fixing mechanisms having a concave-convex engagement structure according to the present invention.

Referring to FIG. 7C, one of methods for fixing the pull line (2) is using a catch-slot or concave-convex engagement mechanism, where one end of the pull line (2) to be fixed is fixed to a small bump (102A) by riveting, and the small bump (102A) and a small groove (102B) on the pull plate (1) form a catch-slot or concave-convex engagement mechanism for use as the pull line fixing mechanism (102).

Figure 7D:
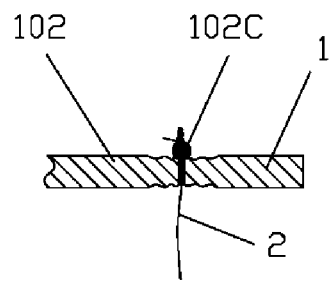
FIG. 7D is a schematic structural view of pull lines fixed to pull line fixing mechanisms of a rivet type according to the present invention.

Referring to FIG. 7D, one of methods for fixing the pull line (2) is using a rivet fastening mechanism, where a small hole is formed on the pull plate, the pull line (2) is passed through the small hole, and the metal plate is compressed and deformed using a locking pliers, so that the pull line (2) can be directly riveted to the pull plate (1). The rivet fastening mechanism (102C) is one of the pull line fixing mechanisms (102) for fixing the pull lines.

Figure 7E:
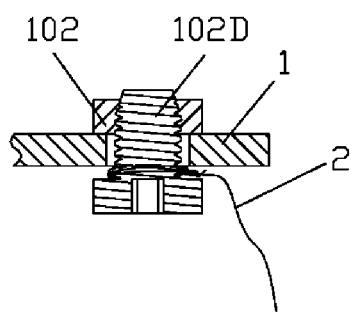
FIG. 7E is a schematic structural view of pull lines fixed to pull line fixing mechanisms of a thread type according to the present invention.

Referring to FIG. 7E, one of methods for fixing the pull line (2) is using a thread fastening mechanism (102D), where the pull line (2) is fixed to the pull plate (1) by using the thread fastening mechanism (102D).

The pull line fixing mechanisms (102) of many other different specific structures may also be designed according to the technical solution provided by the present invention.

Figure 8A:
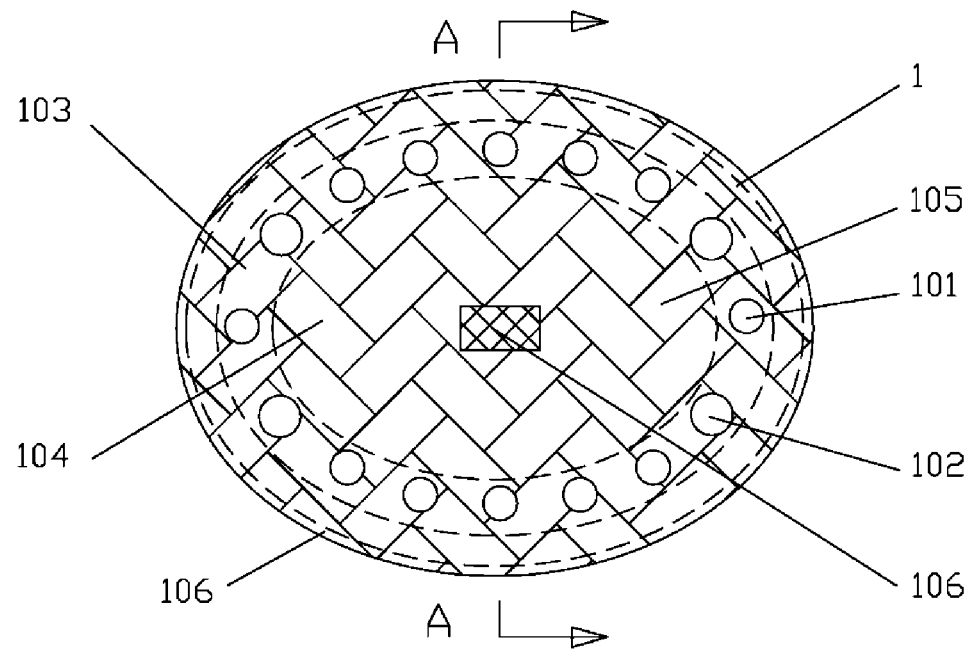
FIG. 8A is a schematic structural view of a pull plate having a composite structure according to the present invention.
Figure 8B:
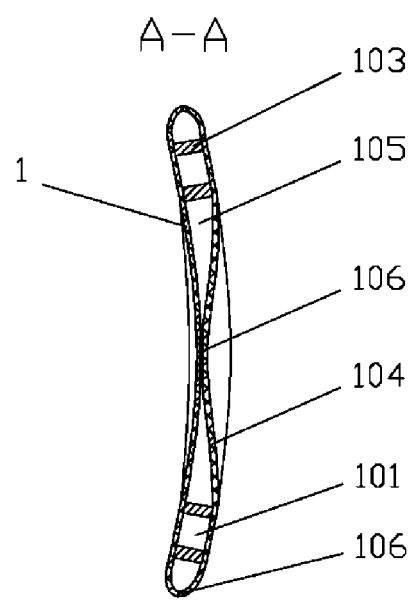
FIG. 8B is an A-A cross-sectional view of FIG. 8A.

Embodiment 8: A Pull Plate Having a Composite Structure of the Present Invention Referring to FIG. 8A and FIG. 8B, in this embodiment, the pull plate (1) adopts a composite structure having medical films (104) wrapped on a frame (103).

The pull plate (1) includes a frame (103) and medical films (104), and the medical films (104) are wrapped on the frame (103). In this embodiment, the frame (103) may be made of a plate. The material of the frame (103) includes, but is not limited to, medial metal materials such as titanium and titanium alloy and medical grade stainless steel, amorphous materials, and medical polymer materials (such as PC and PE); the frame (103) is formed by mechanical processing or wire electro-discharge machining or laser cutting, and hollowing out a plate into a skeleton-like structure.

The medical films (104) are made of a material selected from a group consisting of, but not limited to: a polypropylene fiber braided fabric, a polytetrafluoroethylene film, a polyurethane film and other materials capable of being implanted into the human body for a long term.

The formed medical films (104) are wrapped on the frame (103). The medical films (104) may be wrapped on the frame (103) by thermal bonding, sewing, or chemical adhesive bonding. After the medical films (104) are wrapped on the frame (103), through holes (101) for facilitating growth of tongue tissues and pull line fixing mechanisms (102) are formed thereon, thereby obtaining the pull plate (1) having a composite structure of the present invention.

The medical films (104) may also be directly attached to the frame (103). A special wrapping manner is to bond the medical films (104) together at the hollow part of the frame (103) by thermal bonding, sewing, or chemical adhesive bonding, where the bonded part is referred to as a bonded edge (106). A gap (105) is formed between the two layers of film. The frame (103) is capable of moving freely in the gap (105). Such a composite structure has good adaptability to movement, and can meet the requirements of different movements of the tongue.

Figure 9A:
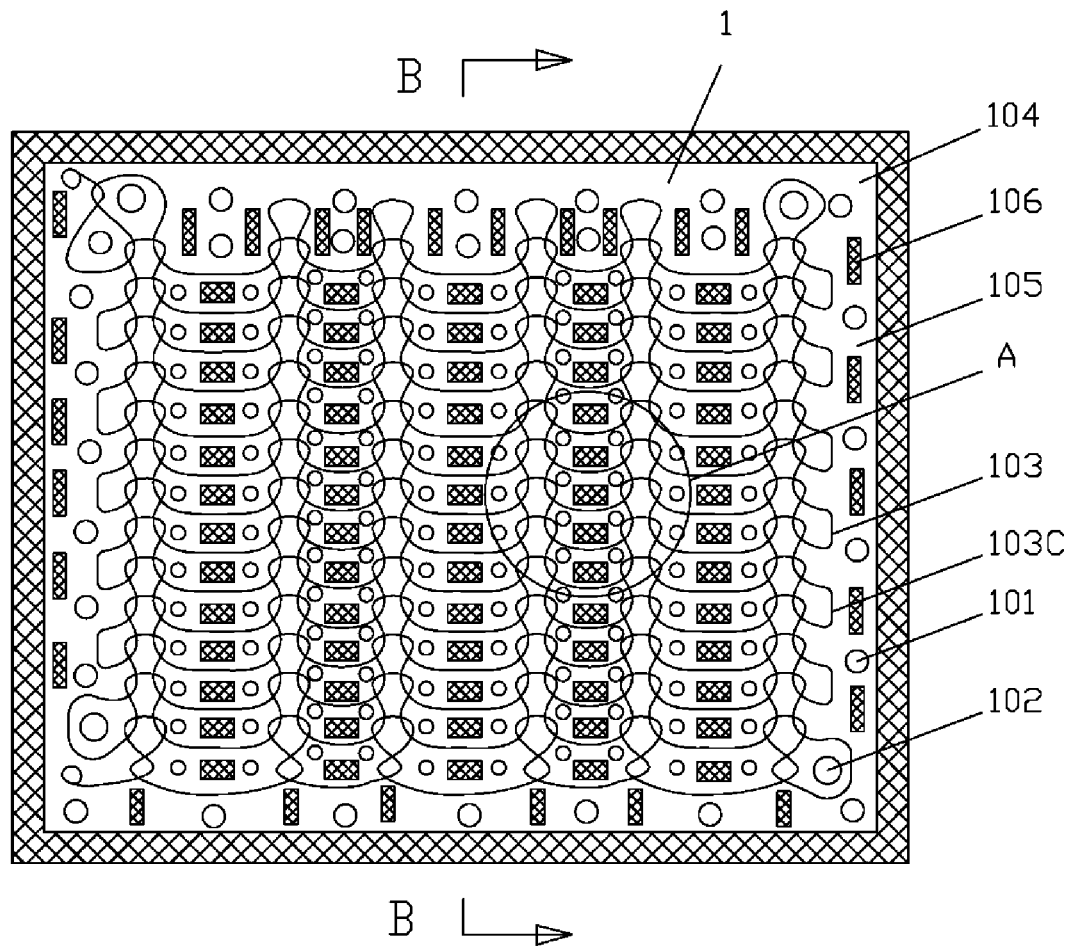
FIG. 9A is a schematic structural view of a pull plate having a wire-braided composite structure according to the present invention.
Figure 9B:
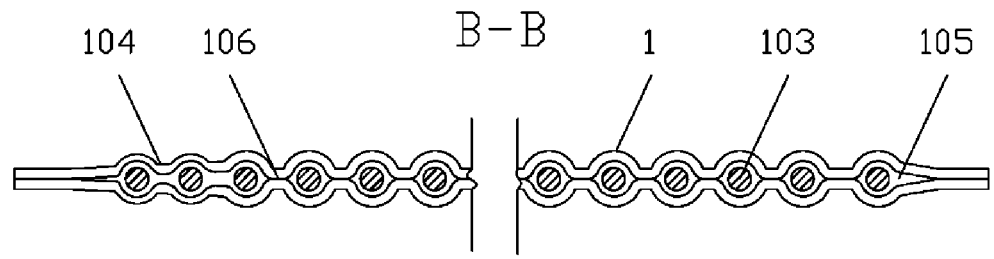
FIG. 9B is a B-B cross-sectional view of FIG. 9A.

Embodiment 9: A Pull Plate Having a Wire-Braided Composite Structure of the Present Invention Referring to FIG. 9A to FIG. 9C, this embodiment shows a pull plate (1) having an improved composite structure. The frame (103) adopts a braided mesh of elastic wires (103C), the medical films (104) are wrapped on the frame (103) which is a mesh formed by braided elastic wires, and the elastic wires (103C) are capable of moving in the gap (105) between the medical films (104).

The elastic wire is selected from a group consisting of, but not limited to: medical grade elastic stainless steel, medical grade titanium-nickel shape memory alloy (Nitinol alloy) wires, Ti—Zr—Ta elastic alloy wires, metallic glass wires and the like, which may also be replaced with elastic polymer material wires such as highly elastic nylon wires.

The braiding manner of the elastic wires is characterized in that an upper row of wires is connected to a lower row of wires through a U-shaped node (108).

Figure 9C:
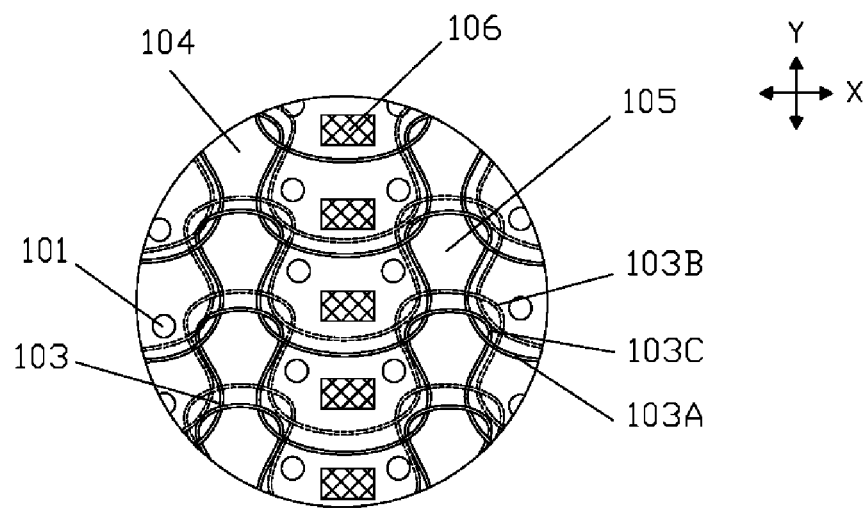
FIG. 9C is an enlarged view of part A of FIG. 9A.

Such an elastic wire mesh formed by braiding through the U-shaped node (108) has good adaptability to movement, and can slide within a certain range in the vertical and horizontal directions, that is, move in the Y direction and X direction as shown in FIG. 9C. For example, it is at position 103A before movement, and may be moved to position 103B, and may further be moved back to position 103A.

Such a braided wire mesh is used as the frame (103), which is wrapped by the medical films (104). At the hollow part of the frame (103), the medical films (104) are bonded together to form a bonded edge (106) by thermal bonding, sewing, or chemical adhesive bonding. The frame (103) formed by the elastic wires is freely placed in the gap (105) formed between the bonded edge (106) and the two layers of medical film (104). Through holes (101) for facilitating growth of tongue tissues and pull line fixing mechanisms (102) are formed at proper positions on the medical films (104), thereby obtaining the pull plate (1) having a wire-braided composite structure of the present invention.

Since human tissues can be attached to and grow on the medical films (104), or penetrate and grow along the through holes (101), but cannot penetrate into the gap (105) between the films, it is ensured that the frame (103) formed by the elastic wires (103C) can move freely in the gap (105) between the films. Therefore, such a pull plate (1) having a wire-braided composite structure has excellent adaptability to movement, and can meet the requirements of different movements of muscle groups in the tongue, thereby improving the comfort when the tongue dorsum portion and/or the tongue base portion is retracted.

Embodiment 10: A Composite Pull Line of the Present Invention

Figure 10A:
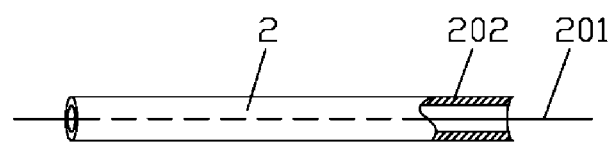
FIG. 10A is a schematic structural view of a composite pull line according to the present invention.
Figure 10B:
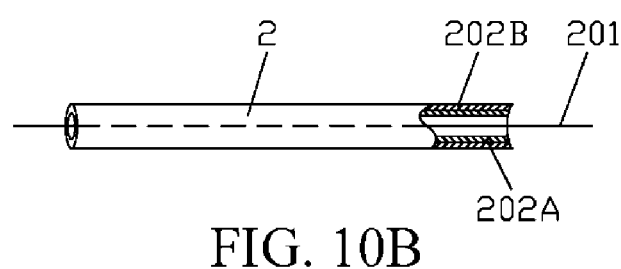
FIG. 10B is a schematic structural view of a multi-layer composite pull line according to the present invention.
Figure 10C:
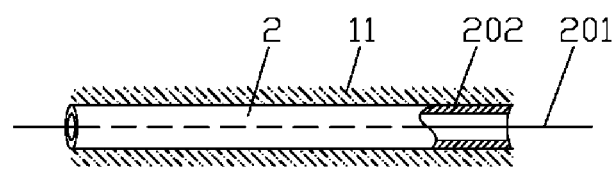
FIG. 10C depicts the working principle of the composite pull line of FIG. 10A when being implanted into a human body.

Referring to FIG. 10A to FIG. 10C, the pull line (2) is generally made of a non-absorbable medical thread. The most commonly used is a non-absorbable surgical suture, including, but not limited to, metal lines, natural fiber lines, synthetic fiber lines (such as polyester lines, polyamide lines, and polypropylene lines) and the like.

Pull Line Having a Composite Structure

Since the tongue pulling device of the present invention can be adjusted after surgery, in the non-sleep state, the control switch (301) is adjusted to an "off" state, and at this time, the tongue base portion receives a small pulling force or is completely in a loosened state, thereby ensuring free movement of the tongue during speaking, swallowing and other activities; before sleep, the control switch (301) is adjusted to an "on" state, and at this time, the tongue base portion receives a large pulling force, or the tongue base portion is in an effective retracted state, so as to maintain the palatopharyngeal portion open, thereby preventing OSAHS. In this way, the pull line (2) has a relative movement in the soft tissues of the tongue. To reduce the cutting effect caused by the relative movement of the pull line (2) in the soft tissues of the tongue, the present invention particularly provides a pull line having a composite structure.

Such a pull line (2) having a composite structure includes a draw line (201) and a protective sheath (202). The draw line (201) is a flexible line made of a high-strength medical material, and is generally made of a non-absorbable surgical suture. The protective sheath (202) is a hollow hose made of a flexible medical material. The protective sheath (202) is sleeved over the draw line (201), and the draw line (201) is capable of moving axially in the protective sheath (202), as shown in FIG. 10A.

The protective sheath (202) is an elastic medical hose, for example, a medical silica gel tube, a medical polyurethane tube, an elastic fiber tube braided by synthetic fibers such as a polypropylene fiber braided tube, or the like. Among others, a composite tube having a multi-layer structure has a good effect, for example, a composite tube having an inner layer (202A) being a polyurethane thin wall tube and an outer layer (202B) being an elastic fiber tube braided by synthetic fibers. The outer layer (202) being an elastic fiber tube braided by synthetic fibers has many tiny holes which facilitate growth and penetration of human tissues so as to enhance the bonding strength. The inner layer (202A) being a polyurethane thin wall tube is smooth and has a small friction resistance, and particularly, is ultra-smooth in the presence of water, facilitating movement of the draw line (201) in the inner layer (202A), as shown in FIG. 10B.

The draw line (201) is generally made of a non-absorbable medical thread. The most commonly used is a non-absorbable surgical suture, including, but not limited to, metal lines, natural fiber lines, synthetic fiber lines (such as polyester lines, polyamide lines, and polypropylene lines) and the like.

The diameter of the draw line (201) is 0.3 mm to 1.3 mm, and preferably 0.35 mm to 0.6 mm.

The inner diameter of the protective sheath (202) is 0.4 mm to 1.5 mm, and preferably 0.4 mm to 1.0 mm.

Since the pull line (2) adopts the composite structure of the draw line (201) and the protective sheath (202), not only movement of the pull line (2) in human tissues is ensured, but also attachment and growth of human tissues on the pull line (2) are facilitated, thereby preventing the pull line (2) from cutting the tongue tissues during reciprocating movement. The pull line (2) forms a tunnel in the tongue tissues along the protective sheath (202), and the draw line (201) is capable of moving in the protective sheath (202) at a low friction force; the tongue tissues of the human body are capable of being attached to and growing along the outer wall of the protective sheath (202), thereby maintaining good bonding strength, as shown in FIG. 10C.

Embodiment 11: A Retractor of a Bolt Adjustment Type of the Present Invention

Figure 11A:
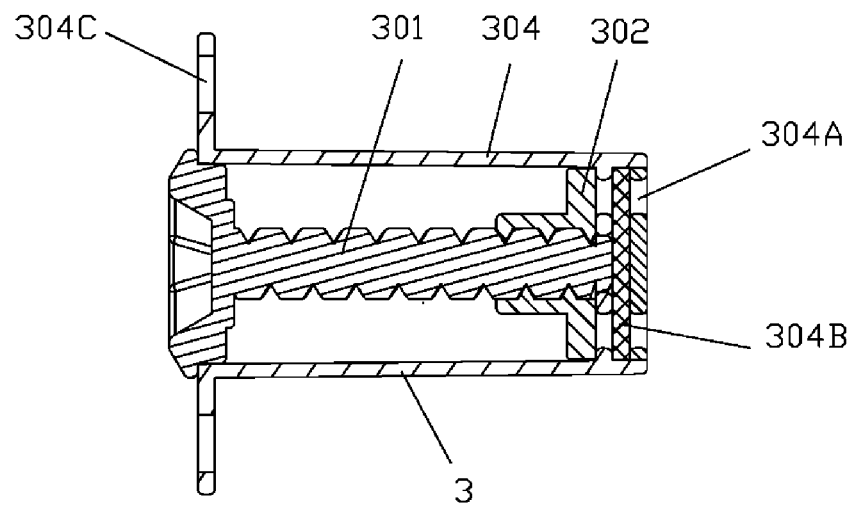
FIG. 11A is a schematic structural view of a retractor of a bolt adjustment type according to the present invention.
Figure 11B:
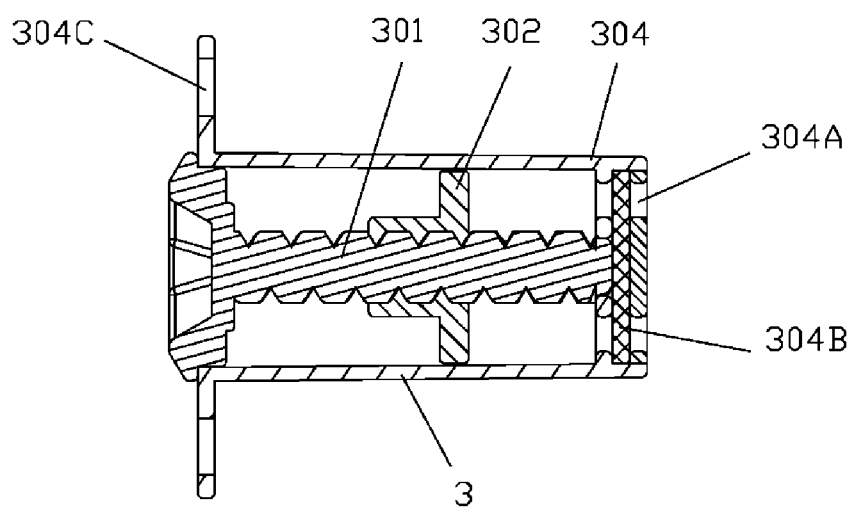
FIG. 11B is a schematic structural view of the retractor of FIG. 11A after the position of the pull line fixing device is moved.

Referring to FIG. 11A to FIG. 11E, this embodiment shows a specific implementation of the thread-type retractor. The retractor (3) at least includes a control switch (301) capable of adjusting a tension of the pull line (2), a pull line fixing mechanism (302), and a casing (304). The control switch (301) of the retractor (3) adopts a thread-bolt structure, and when the bolt-type control switch (301) is rotated, the pull line fixing mechanism (302) moves horizontally along the axial direction of the bolt. When the rotation is clockwise, the pull line fixing mechanism (302) moves leftward, that is, moves toward the top, so that the pull line (2) is tightened; when the rotation is anticlockwise, the pull line fixing mechanism (302) moves rightward, that is, moves toward the bottom, so that the pull line (2) is loosened, as shown in FIG. 11A and FIG. 11B. The moving distance of the pull line fixing mechanism (302) is generally 5 mm to 20 mm. The outer diameter of the retractor (3) is generally 1 mm to 10 mm, and preferably 2 mm to 6 mm.

The retractor (3) of this embodiment includes the control switch (301), the pull line fixing device (302), and the retractor casing (304). The control switch (301) and the pull line fixing device (302) are mounted in the retractor casing (304) to form a closed container. Positioning concave grooves (302B) on the pull line fixing device and positioning convex steps (304E) on the retractor casing form a concave-convex engagement, and the pull line fixing device (302) is capable of moving along the positioning convex steps (304E), but is incapable of rotating.

The control switch (301) is a bolt structure, and the pull line fixing device (302) is a nut structure, so that the control switch (301) and the pull line fixing device (302) form an adjustable thread-bolt structure. When the control switch (301) is rotated using a screwdriver, the bolt of the control switch (301) is rotated, and the pull line fixing device (302) is restricted by the positioning convex steps (304E) and cannot rotate, but can only move horizontally along the bolt. When the pull line (2) is fixed to the pull line fixing device (302), the objective of tightening or loosening the pull line (2) can be achieved.

The pull line fixing device (302) includes thread holes (302A), the positioning concave grooves (302B), and an internal thread (302J). The thread holes (302A) are used for tying the pull line (2) so as to fix the pull line (2). The positioning concave grooves (302B) are used for forming a concave-convex engagement with the positioning convex steps (304E) on the retractor casing, so as to prevent rotary movement of the pull line fixing device (302). The internal thread (302J) is used for being engaged with the bolt of the control switch (301), so that the pull line fixing device (302) can move horizontally when the bolt of the control switch (301) is rotated.

The retractor casing (304) includes thread holes (304A), a seal ring (304B), screw holes (304C), the positioning convex steps (304E) and a main body (304L). The thread holes (304A) are used for the pull line (2) to pass through. The seal ring (304B) is made of medical grade silica gel, and not only allows the pull line (2) to pass through, but also has a sealing function to block human tissues from growing and penetrating into the main body (304L). The screw holes (304C) are used for fixing the retractor (3) to the mandible (5). The positioning convex steps (304E) and the positioning concave grooves (302B) on the pull line fixing device form a concave-convex engagement, so as to prevent rotary movement of the pull line fixing device (302). The main body (304L) is used for mounting and fixing the control switch (301) and serves as a support for bearing the pull line fixing device (302). At the same time, a closed space may be formed to block human tissues from growing and penetrating into the main body (304L), thereby ensuring the adjustment function of the control switch (301).

The structure of the retractor (3) shown in this embodiment is reliable, can conveniently fix the pull line (2), is easily mounted onto the mandible, can be manufactured into small components, and is conveniently implanted into the human body.

Figure 12A:
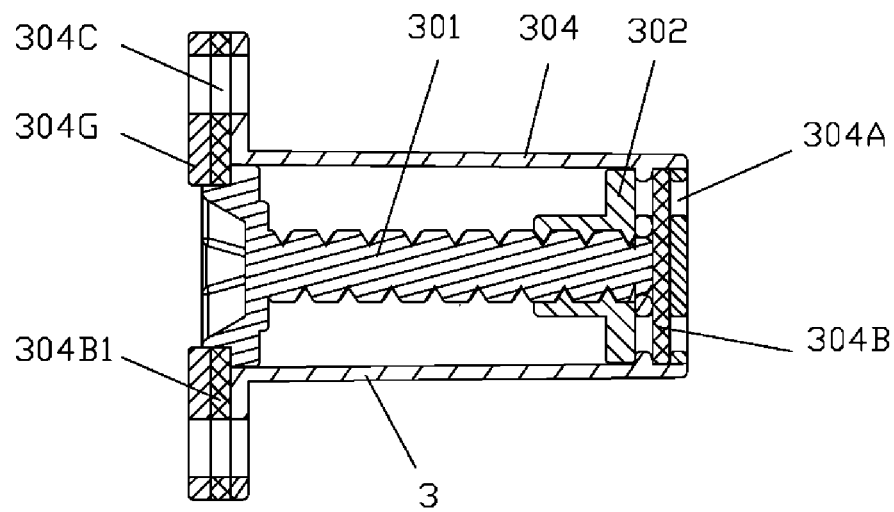
FIG. 12A is a schematic structural view of a retractor of a bolt adjustment type having a sealing top cover according to the present invention.
Figure 12B:
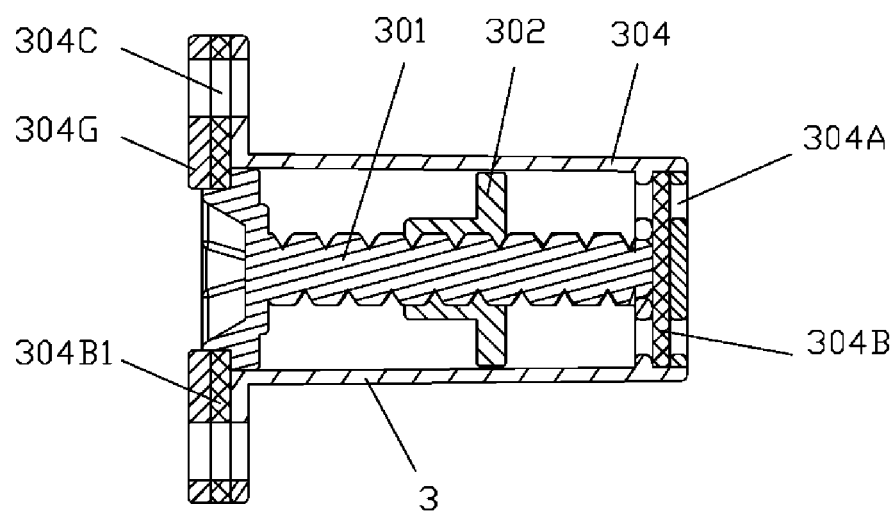
FIG. 12B is a schematic structural view of the retractor of FIG. 12A after the position of the pull line fixing device is moved.
Figure 13A:
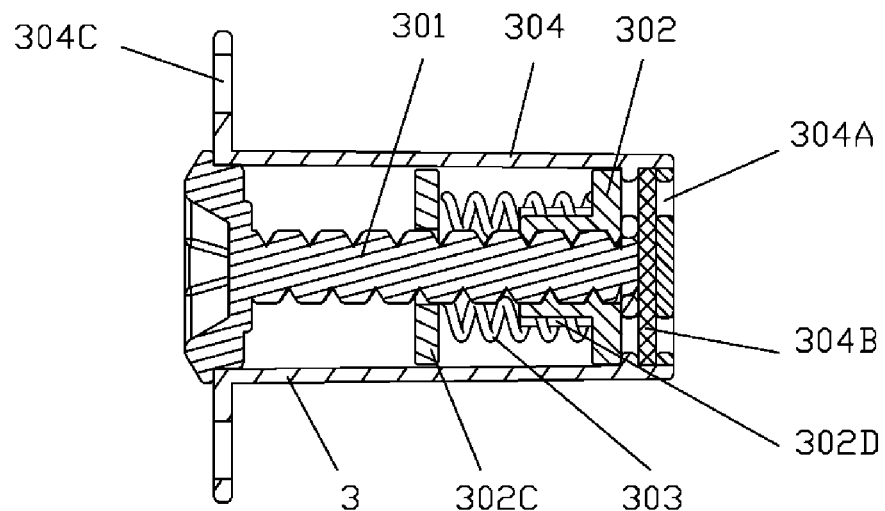
FIG. 13A is a schematic structural view of a retractor of a bolt adjustment type having an anti-cutting buffer device according to the present invention.
Figure 13B:
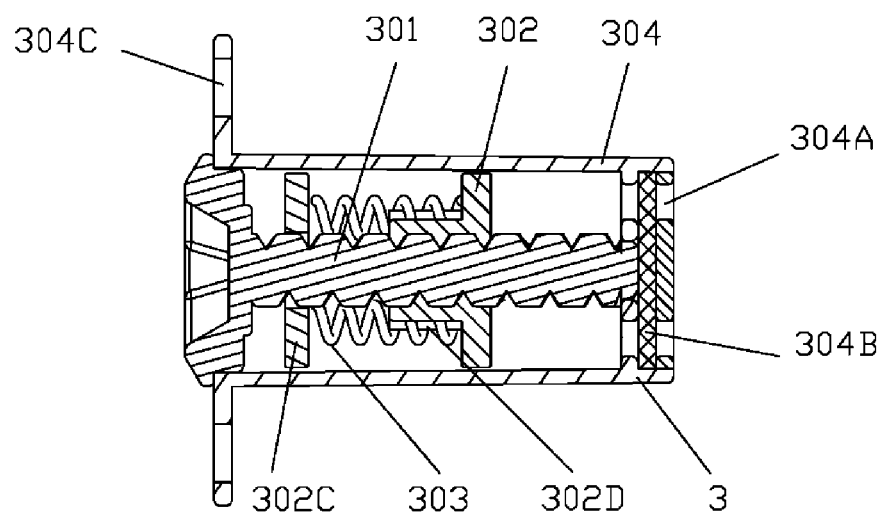
FIG. 13B is a schematic structural view of the retractor of FIG. 13A after the position of the pull line fixing device is moved.

Embodiment 12: A Retractor of a Bolt Adjustment Type Having a Sealing Top Cover of the Present Invention Referring to FIG. 12A to FIG. 12B, this embodiment is a thread-type retractor, which is an improvement to Embodiment 11. The difference lies in that: a top cover (304G) and a top cover seal ring (304B1) are added to the retractor casing (304). The purpose of adding the top cover (304G) and the top cover seal ring (304B1) is to enhance the sealing performance of the top of the retractor casing (304), so that good dynamic sealing performance can be maintained when the bolt of the control switch (301) is rotated, thereby blocking human tissues, tissue fluid or bacteria from entering the retractor casing (304).

Embodiment 13: A Retractor of a Bolt Adjustment Type Having an Anti-Cutting Buffer Device of the Present Invention Referring to FIG. 13A to FIG. 13E, this embodiment is an improvement to Embodiment 11. The difference lies in that: an anti-cutting buffer device (303) is added to the retractor (3).

The anti-cutting buffer device (303) in this embodiment is four coil springs, where top ends of the four coil springs are connected to a binding plate (302C), and bottom ends of the four coil springs are mounted on spring positioning posts (302D) of the pull line fixing device (302).

The pull line (2) is bound to the binding plate (302C), and when the pull line (2) receives an excessive tension, the coil springs of the anti-cutting buffer device (303) deform, and the springs are compressed to eliminate the excessive tension, so as to prevent the pull plate (1) from cutting the soft tissues of the tongue.

The tension for causing deformation of the coil springs of the anti-cutting buffer device (303) is generally set to 100 g to 3000 g, and preferably 500 g to 1000 g, which may be set according to the maximum tensions of the tongues of different patients and the contact area between the pull plate (1) and the tongue base portion. The setting principle is that: under the maximum tension, the maximum pressure generated by the pull plate (1) is lower than the pressure when the soft tissues are cut, and is generally required to be smaller than 7000 $g/cm^2$.

The elastic force of the spring structure of the anti-cutting buffer device (303) is generally smaller than 1000 g, or the pressure generated on the pull plate (1) by the elastic force of the spring structure of the anti-cutting buffer device (303) is smaller than 7000 $g/cm^2$, and is preferably 500 $g/cm^2$ to 1500 $g/cm^2$. At this time, not only effective pulling to the tongue base (41) and/or the tongue dorsum (42) is maintained, but also injuries caused by cutting the tongue muscles are avoided.

Embodiment 14: A Retractor of a Nut Adjustment Type of the Present Invention

Referring to FIG. 14A to FIG. 14E, this embodiment shows a thread-type retractor (3), where the control switch (301) of the thread-type retractor (3) adopts a nut adjustment manner.

Figure 14A:
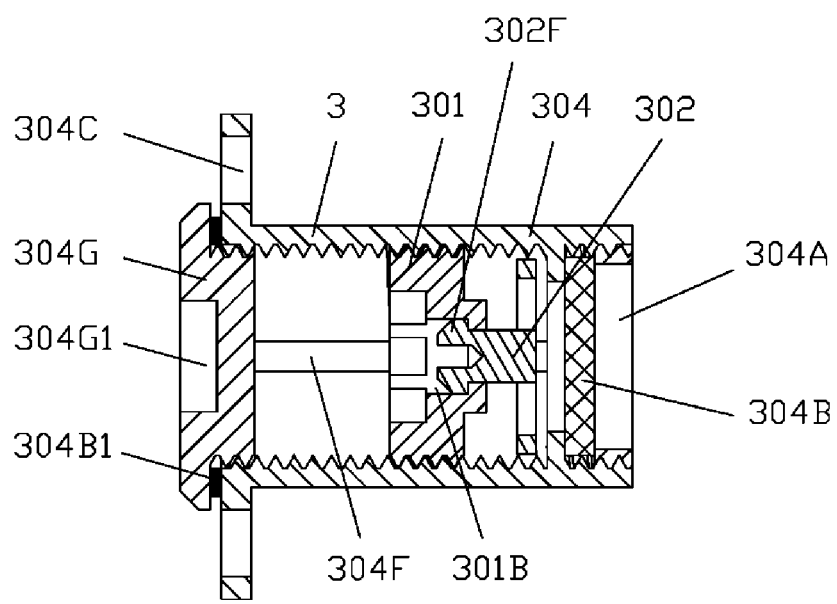
FIG. 14A is a schematic structural view of a retractor of a nut adjustment type according to the present invention.
Figure 14B:
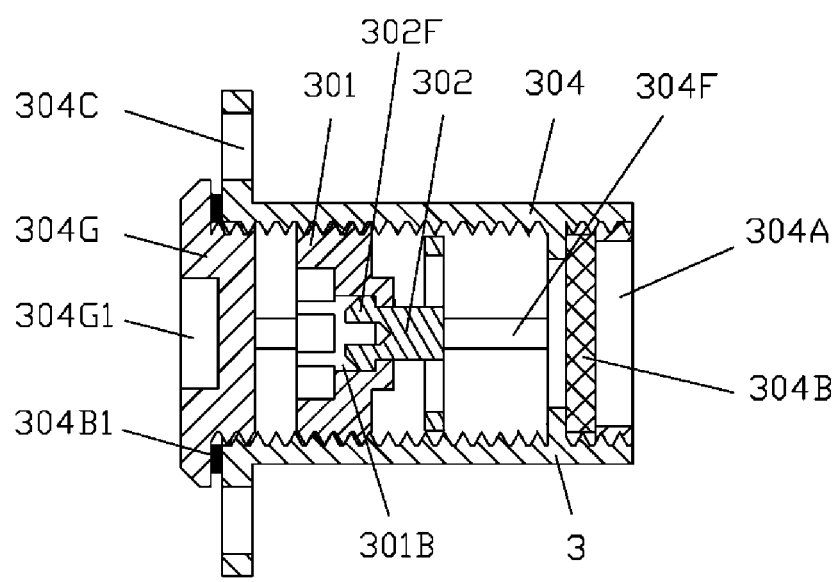
FIG. 14B is a schematic structural view of the retractor of FIG. 14A after the position of the pull line fixing device is moved.
Figure 15A:
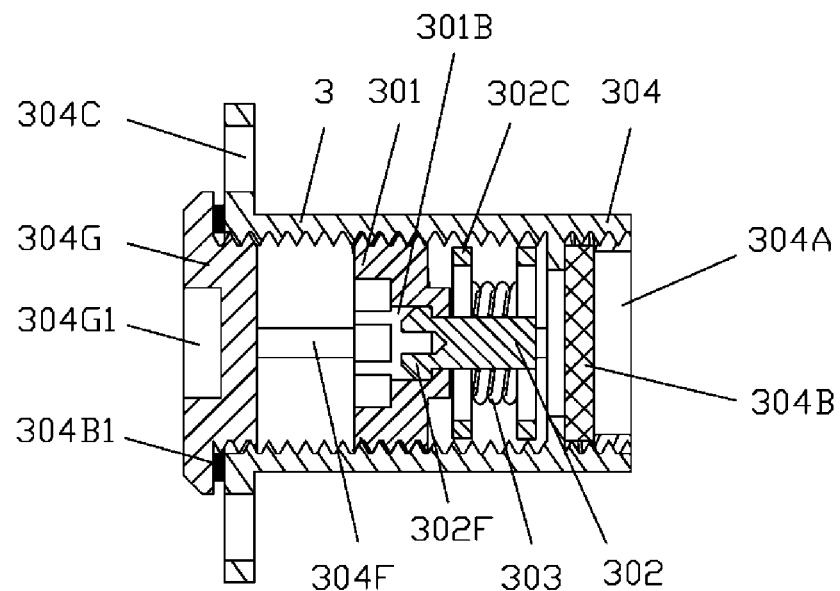
FIG. 15A is a schematic structural view of a retractor of a nut adjustment type having an anti-cutting buffer device according to the present invention.
Figure 15B:
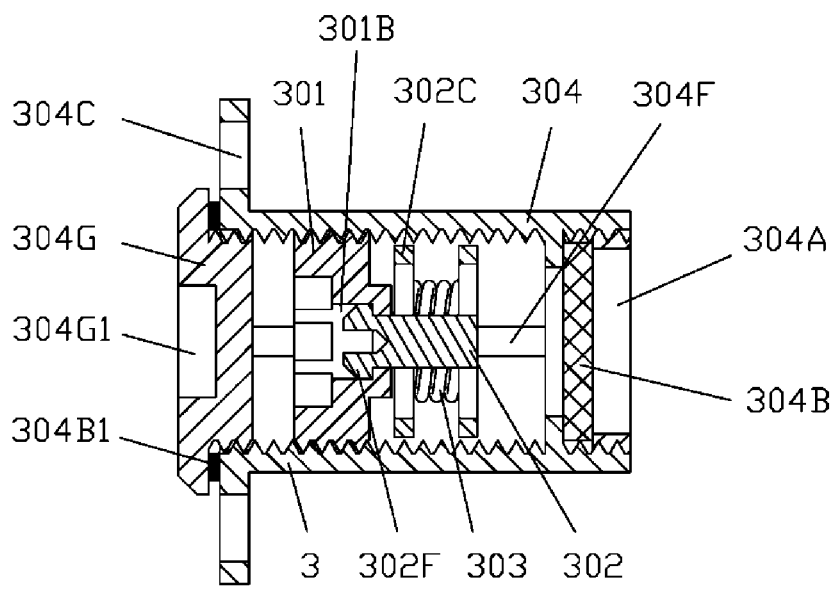
FIG. 15B is a schematic structural view of the retractor of FIG. 15A after the position of the pull line fixing device is moved.
Figure 16A:
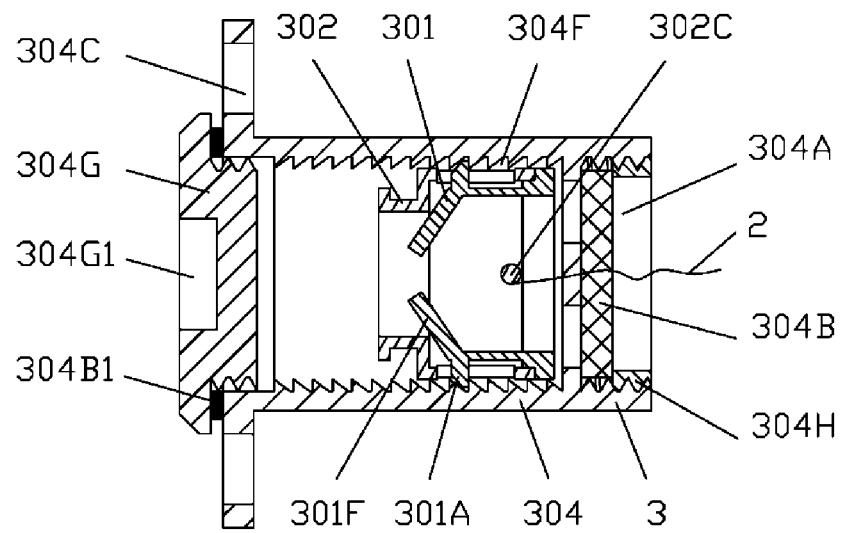
FIG. 16A is a schematic structural view of a push-pull type retractor according to the present invention.
Figure 16B:
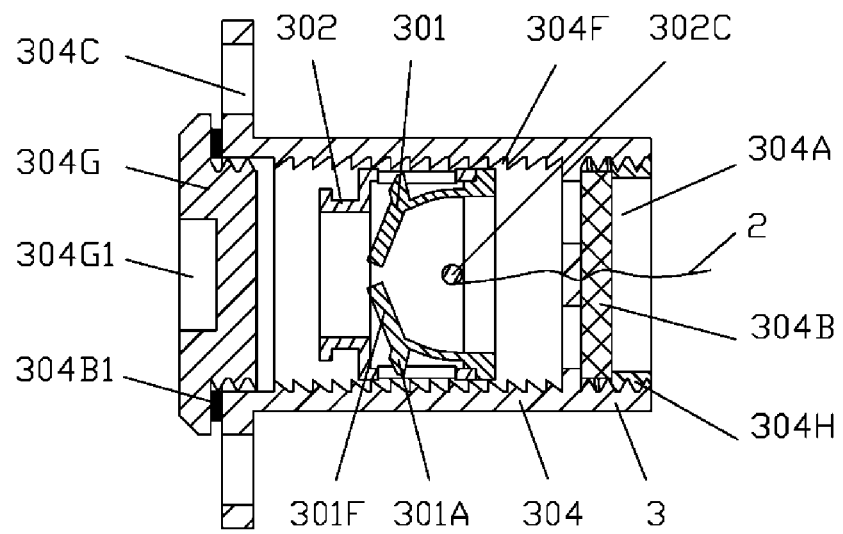
FIG. 16B is a schematic structural view of the retractor of FIG. 16A after the position of the pull line fixing device is moved.
Figures 16C, 16D, 16E:
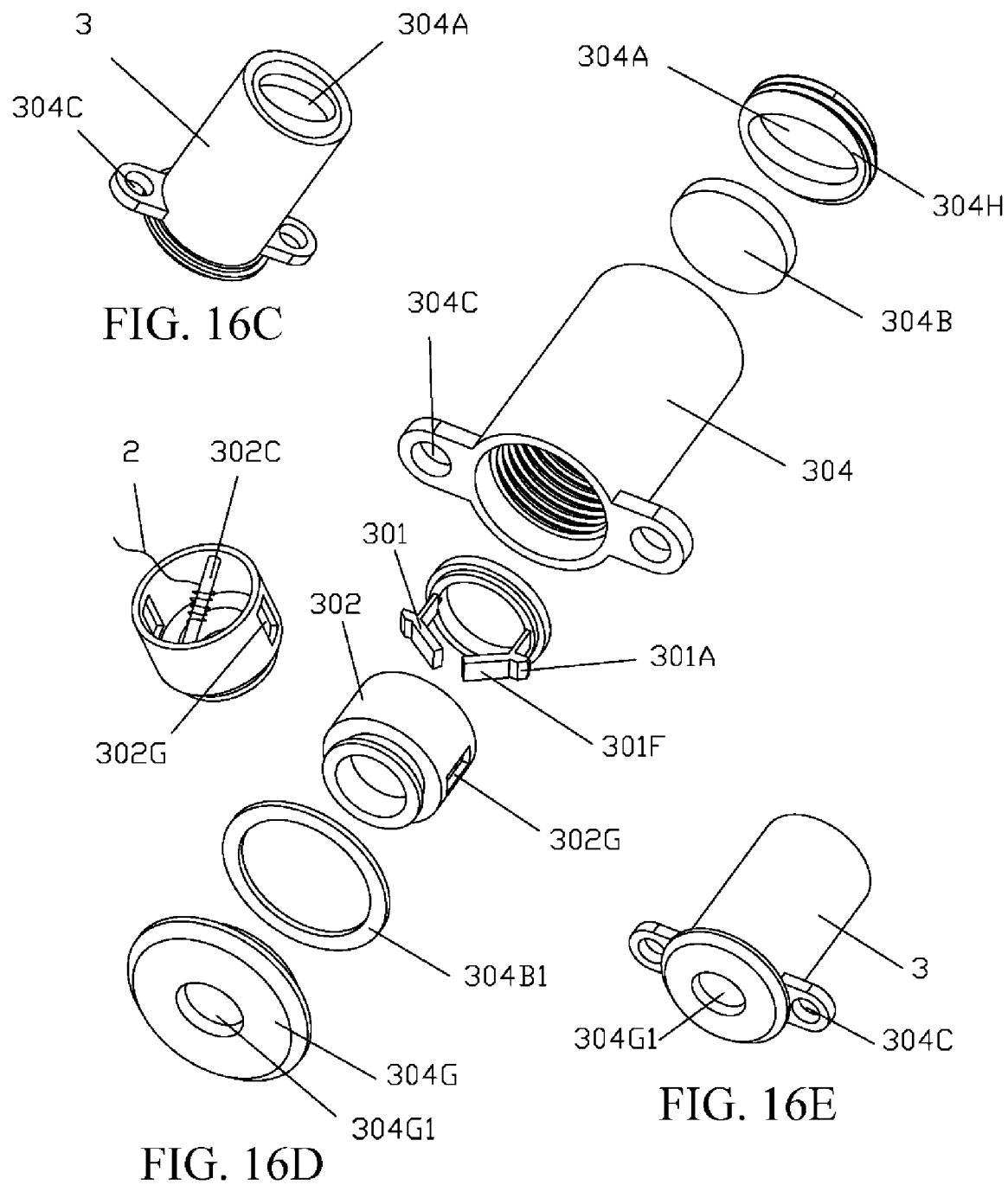
FIG. 16C is a three-dimensional view showing the bottom structure of the retractor of FIG. 16A.
FIG. 16D is an exploded view of the retractor of FIG. 16A.
FIG. 16E is a three-dimensional view showing the top structure of the retractor of FIG. 16A.
Figure 17A:
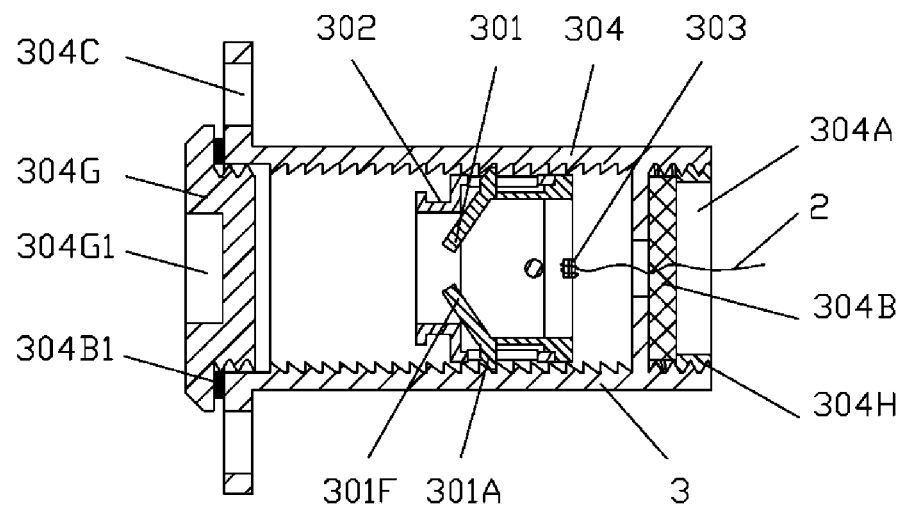
FIG. 17A is a schematic structural view of a push-pull type retractor having an anti-cutting buffer device according to the present invention.
Figure 17B:
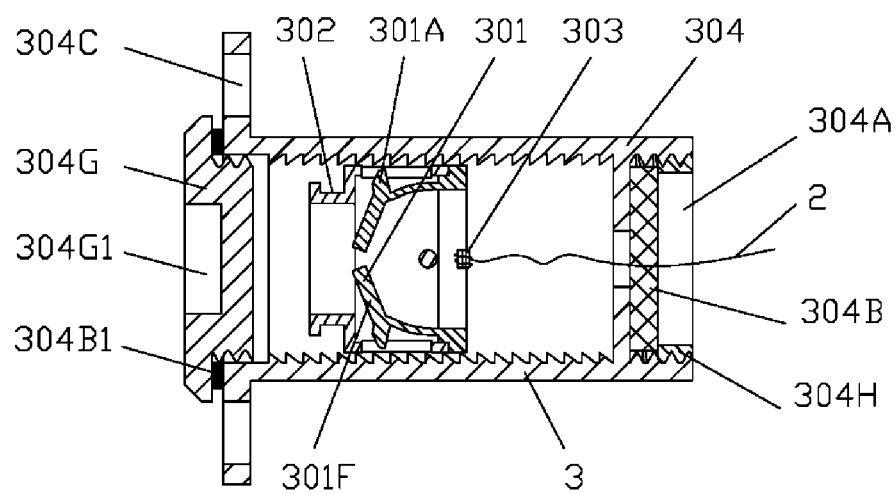
FIG. 17B is a schematic structural view of the retractor of FIG. 17A after the position of the pull line fixing device is moved.
Figures 17C, 17D, 17E:
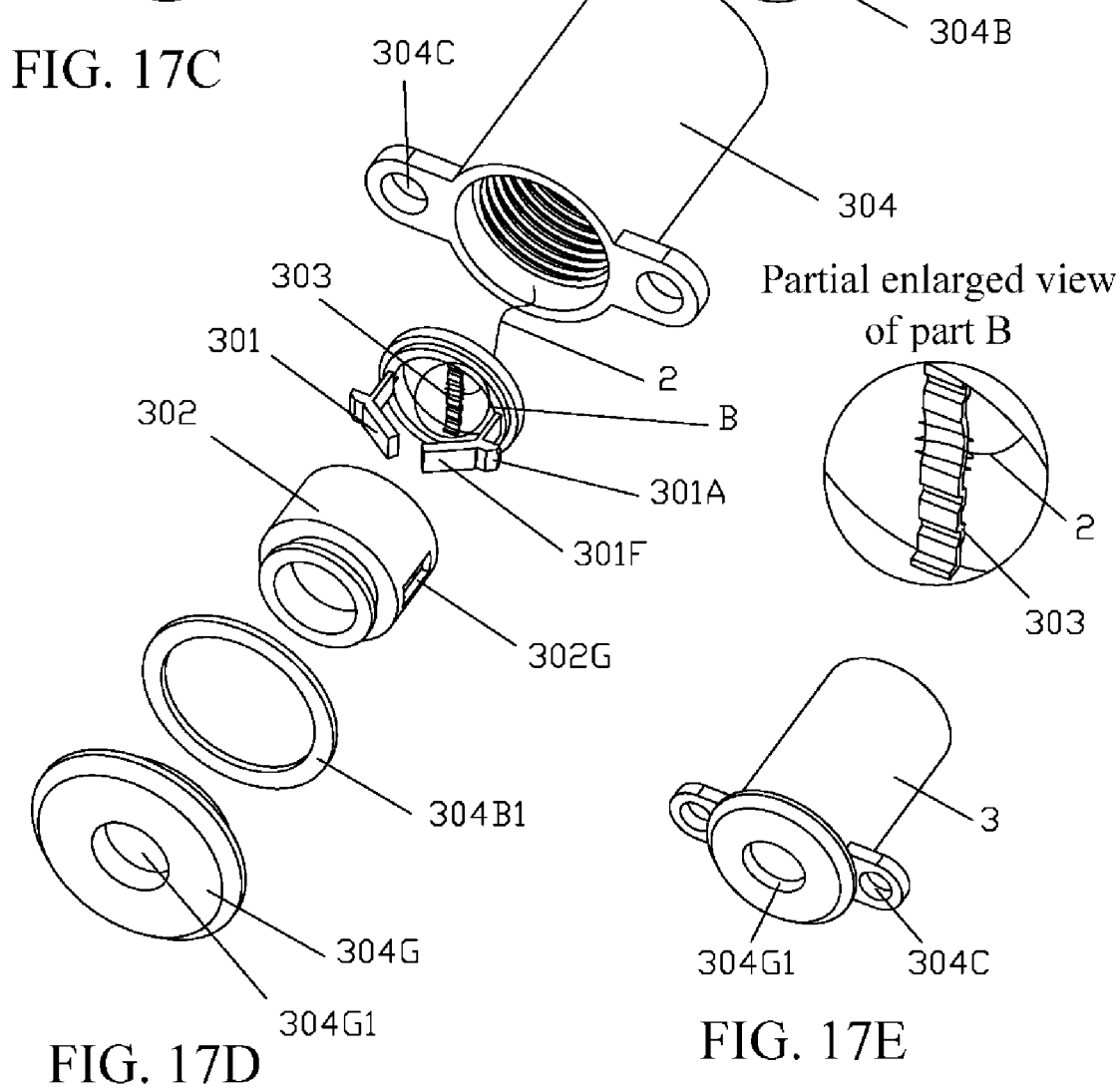
FIG. 17C is a three-dimensional view showing the bottom structure of the retractor of FIG. 17A.
FIG. 17D is an exploded view of the retractor of FIG. 17A.
FIG. 17E is a three-dimensional view showing the top structure of the retractor of FIG. 17A.
Figure 18A:
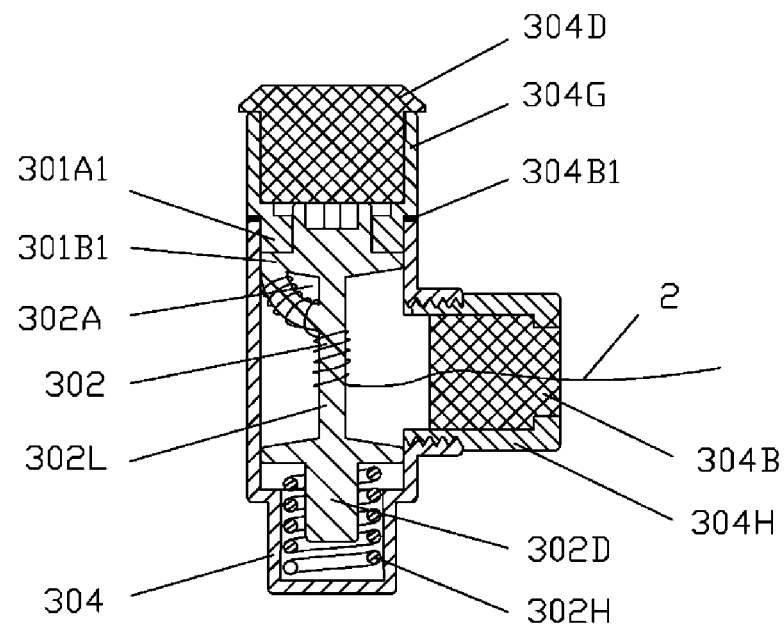
FIG. 18A is a schematic structural view of a clutch-type retractor according to the present invention.
Figure 18B:
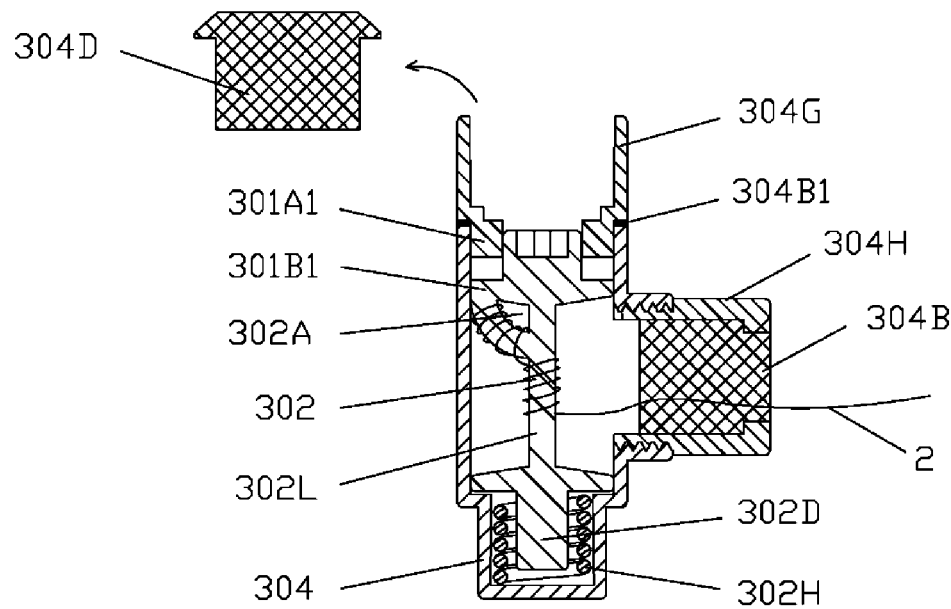
FIG. 18B is a schematic structural view of the retractor of FIG. 18A in a disassembled state.
Figure 18E:
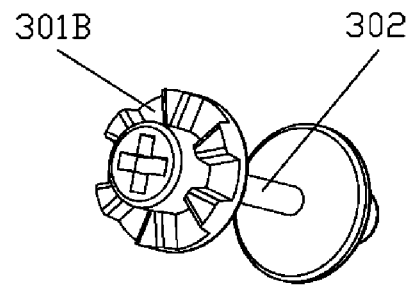
FIG. 18E is a three-dimensional view showing the structure of the control switch of the retractor of FIG. 18A.
Figure 18F:
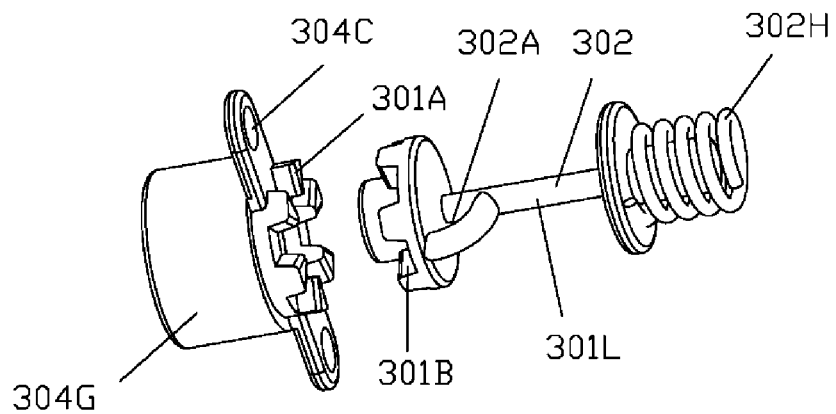
FIG. 18F is a view depicting the working principle of the retractor of FIG. 18A when the clutch-type retractor is disassembled.
Figure 18G:
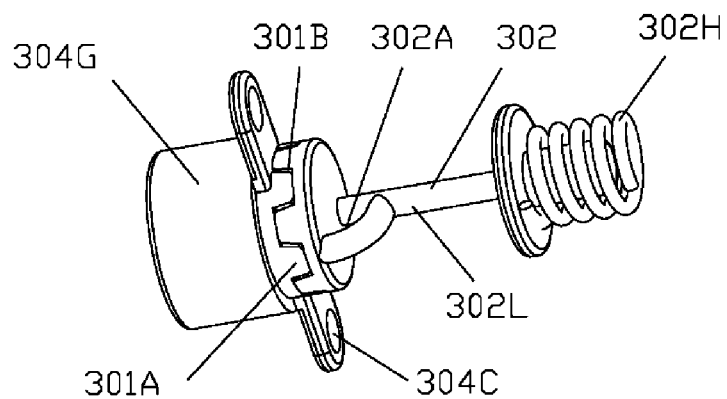
FIG. 18G is a view depicting the working principle of the retractor of FIG. 18A when the clutch-type retractor is assembled.
Figure 19A:
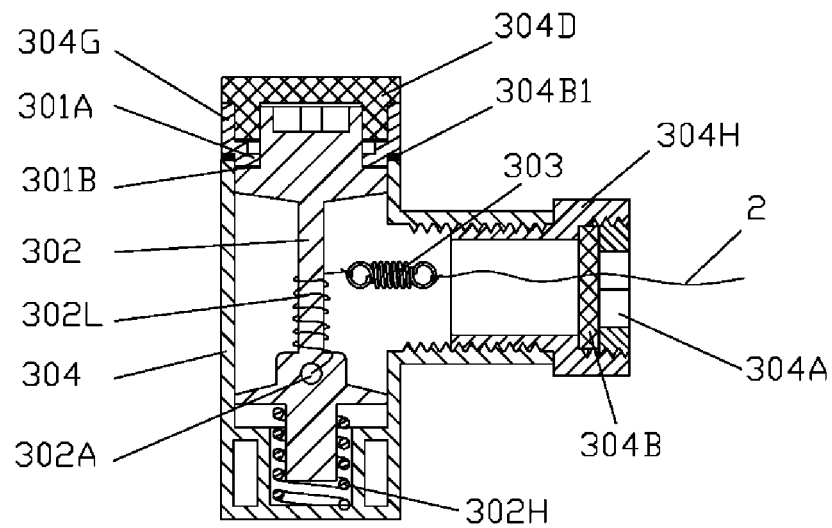
FIG. 19A is a schematic structural view of a clutch-type retractor having an anti-cutting buffer device according to the present invention.
Figure 19B:
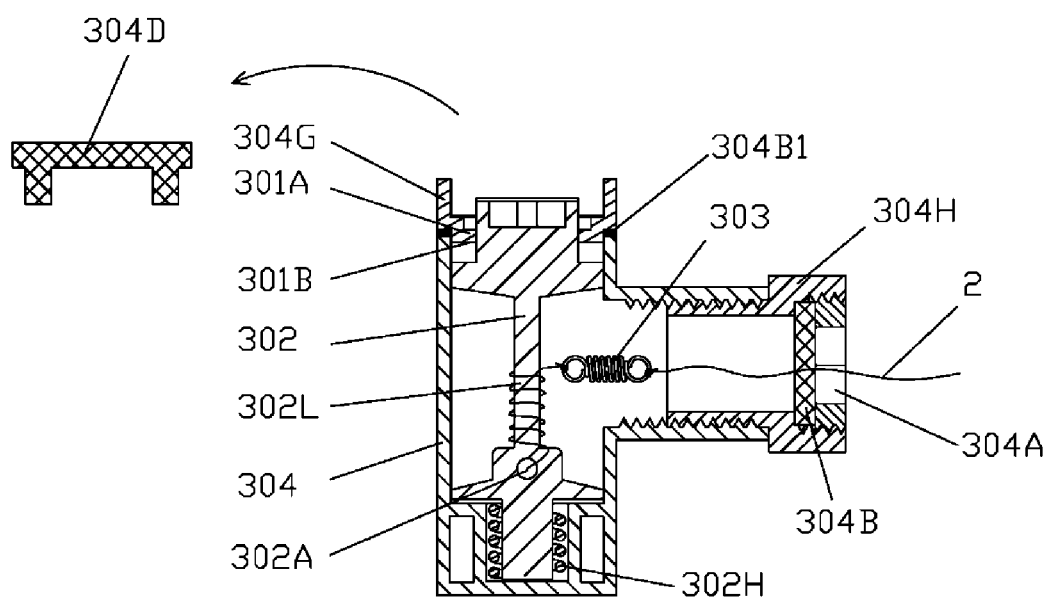
FIG. 19B is a schematic structural view of the retractor of FIG. 19A in a disassembled state.
Figures 19C, 19D:
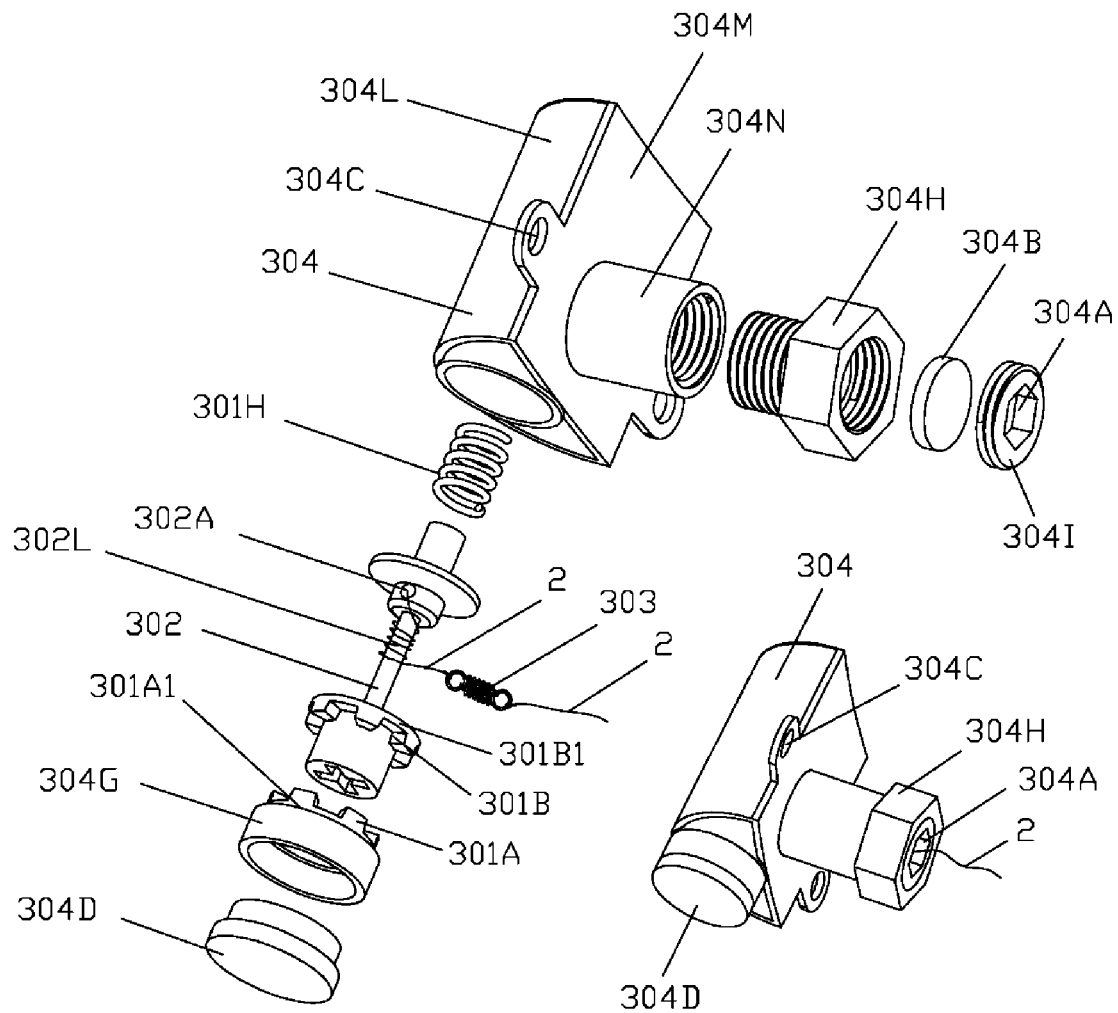
FIG. 19C is an exploded view of the retractor of FIG. 19A.
FIG. 19D is a three-dimensional view showing the side structure of the retractor of FIG. 19A.
Figure 19E:
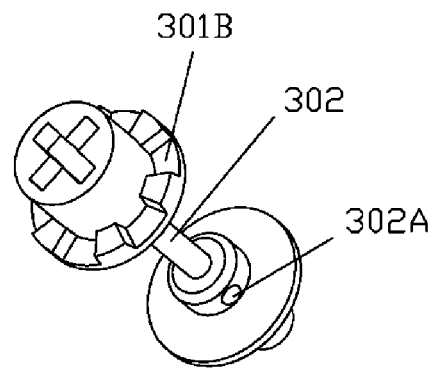
FIG. 19E is a three-dimensional view showing the structure of the control switch of the retractor of FIG. 19A.
Figure 19F:
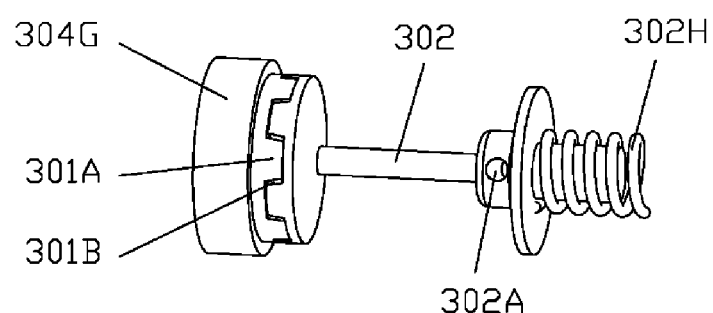
FIG. 19F is a view depicting the working principle of the retractor of FIG. 19A when the clutch-type retractor is disassembled.
Figure 19G:
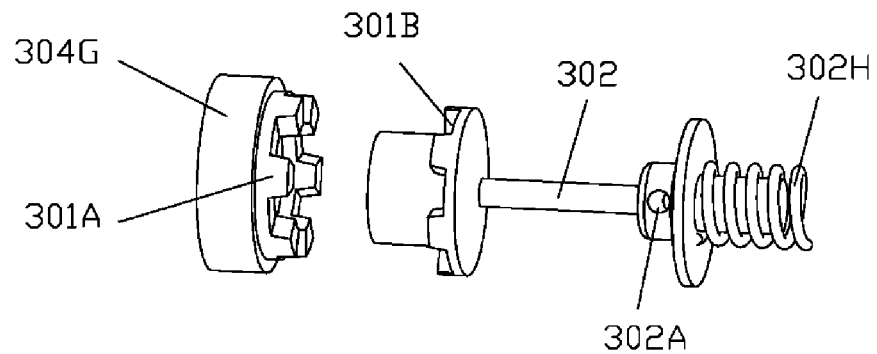
FIG. 19G is a view depicting the working principle of the retractor of FIG. 19A when the clutch-type retractor is assembled.
Figure 20A:
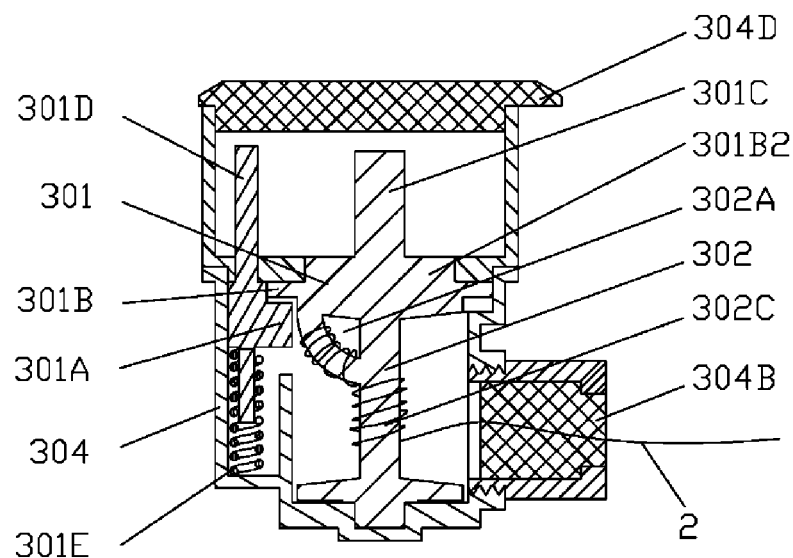
FIG. 20A is a schematic structural view of a ratchet-type retractor according to the present invention.
Figure 20B:
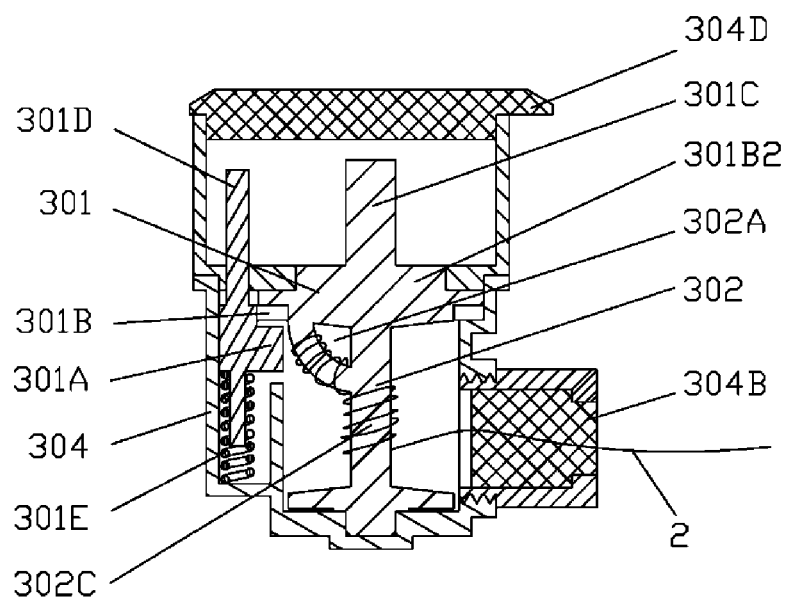
FIG. 20B is a schematic structural view of the retractor of FIG. 20A in a disassembled state.
Figures 20C, 20D:
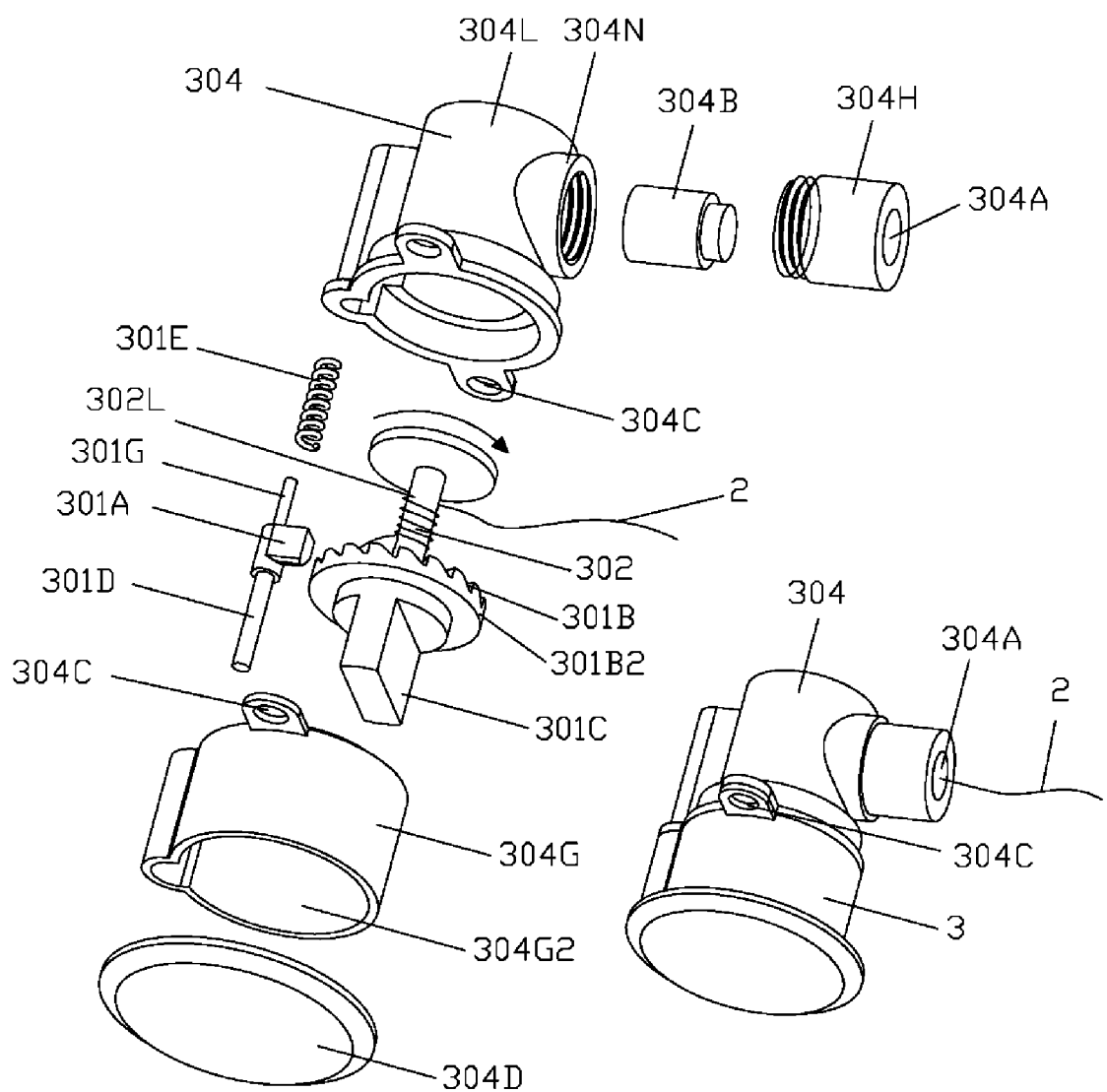
FIG. 20C is an exploded view of the retractor of FIG. 20A.
FIG. 20D is a three-dimensional view of the retractor of FIG. 20A.
Figure 21A:
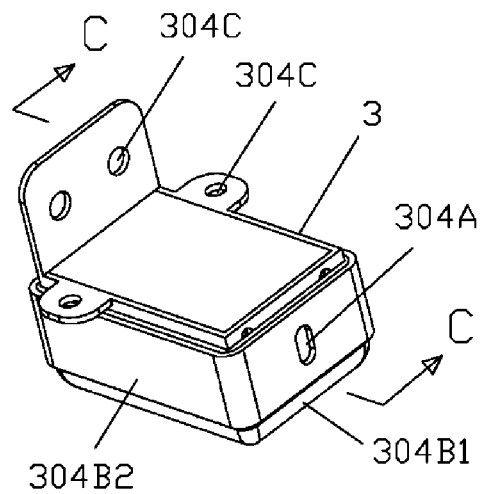
FIG. 21A is a three-dimensional view of a single-switch push-pull type retractor according to the present invention.
Figure 21B:
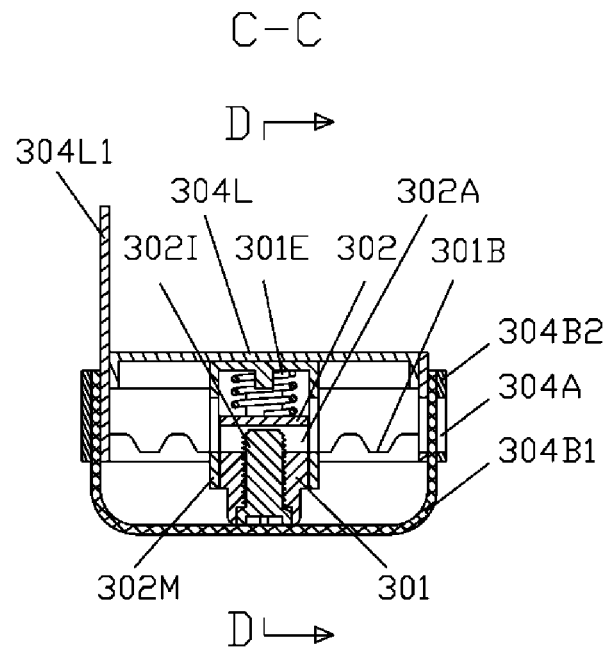
FIG. 21B is a longitudinal cross-sectional view of FIG. 21A.
Figure 21C:
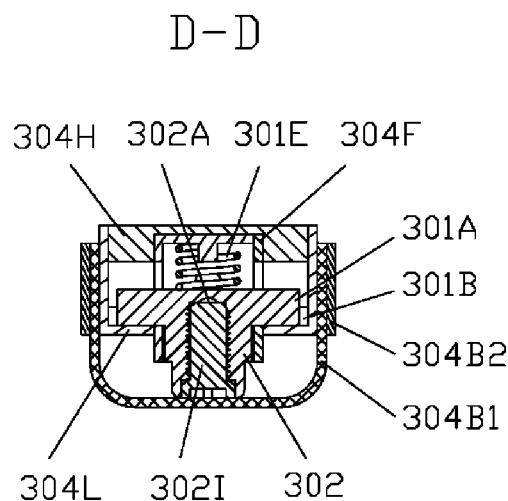
FIG. 21C is a transversal cross-sectional view of FIG. 21A.
Figure 21D:
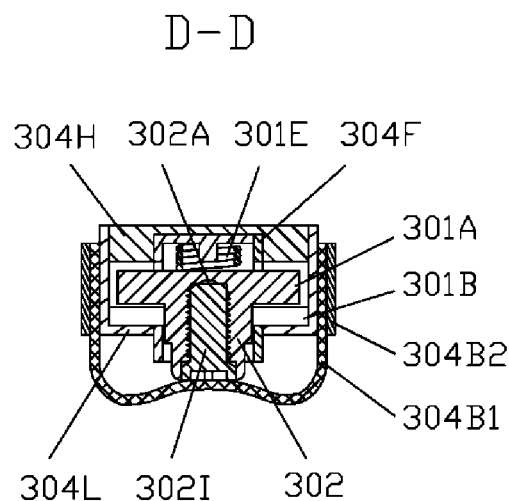
FIG. 21D is a schematic structural view of the retractor of FIG. 21C after the control switch is pressed.
Figure 21I:
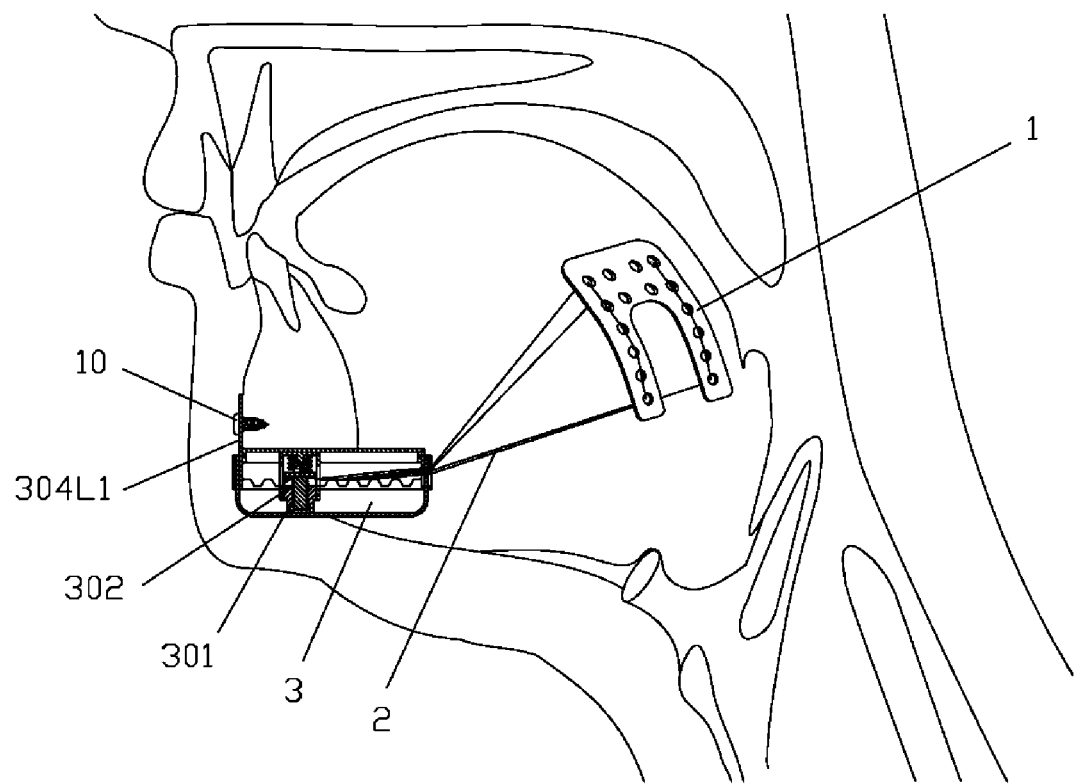
FIG. 21I a mounting view of and a view depicting the working principle of the retractor of FIG. 21A.
Figure 21K:
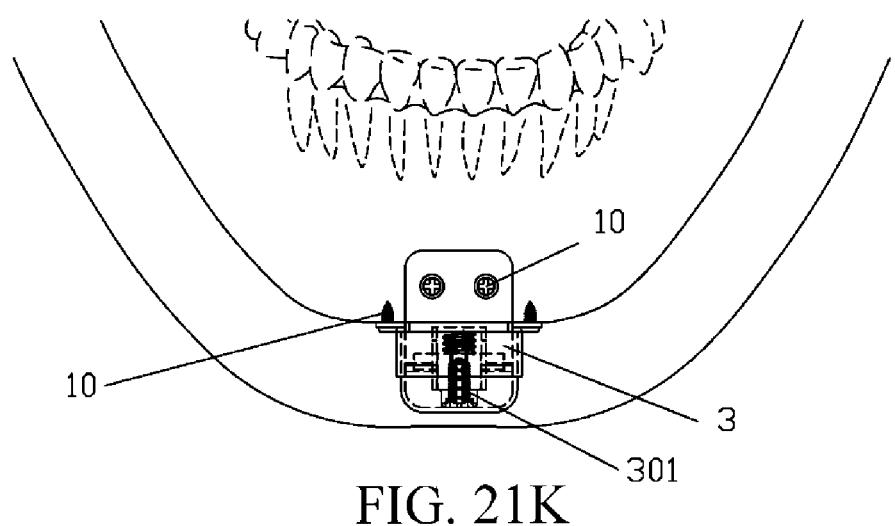
FIG. 21K is a mounting view of the retractor of FIG. 21A.

The retractor (3) at least includes a control switch (301) capable of adjusting a tension of the pull line (2), a pull line fixing mechanism (302), and a casing (304). The control switch (301) of the retractor (3) adopts a nut adjustment manner, and when the nut-type control switch (301) is rotated, the pull line fixing mechanism (302) moves horizontally along the axial direction of the num. When the rotation is clockwise, the pull line fixing mechanism (302) moves leftward, that is, moves toward the top, so that the pull line (2) is tightened; when the rotation is anticlockwise, the pull line fixing mechanism (302) moves rightward, that is, moves toward the bottom, so that the pull line (2) is loosened, as shown in FIG. 14A and FIG. 14B. The moving distance of the pull line fixing mechanism (302) is generally 5 mm to 20 mm. The outer diameter of the retractor (3) is generally 1 mm to 10 mm, and preferably 2 mm to 6 mm.

The retractor (3) of this embodiment includes the control switch (301), the pull line fixing device (302), and the retractor casing (304). The control switch (301) and the pull line fixing device (302) are mounted in the retractor casing (304) to form a closed container. Positioning convex steps (302E) on the pull line fixing device and positioning concave grooves (304F) on the retractor casing form a concave-convex engagement, and the pull line fixing device (302) is capable of moving along the positioning concave grooves (304F), but is incapable of rotating.

The control switch (301) is a nut structure, and the pull line fixing device (302) is connected to the control switch (301) through a concave-convex engagement structure, that is, positioning convex steps (302F) on the pull line fixing device (302) and a positioning concave groove (301B) on the control switch (301) form a concave-convex engagement structure. When the nut-type control switch (301) is rotated using a screwdriver, the control switch (301) rotates, and at the same time moves linearly along the horizontal direction; and the pull line fixing device (302) is restricted by the positioning concave grooves (304F) on the casing (304) and cannot rotate, but can only move correspondingly along the horizontal direction under the pulling of the control switch (301). When the pull line (2) is fixed to the pull line fixing device (302), the objective of tightening or loosening the pull line (2) can be achieved.

The pull line fixing device (302) includes thread holes (302A), the positioning convex steps (302E), and the positioning convex steps (302F). The thread holes (302A) are used for the pull line (2) to pass through so as to tie and fix the pull line (2). The positioning convex steps (302E) are used for forming a concave-convex engagement with the positioning concave grooves (304F) on the retractor casing, so as to prevent rotary movement of the pull line fixing device (302). The positioning convex steps (302F) are used for being engaged with the positioning concave groove (301B) of the control switch (301), so that the pull line fixing device (302) can move horizontally when the nut-type control switch (301) is rotated.

The retractor casing (304) includes thread holes (304A), a seal ring (304B), screw holes (304C), the positioning concave grooves (304F), a top cover seal ring (304B1), a top cover (304G), a bottom cover (304H) and a main body (304L). The thread holes (304A) are used for the pull line (2) to pass through. The seal ring (304B) is made of medical grade silica gel, and not only allows the pull line (2) to pass through, but also has a sealing function to block human tissues from growing and penetrating into the main body (304L). The screw holes (304C) are used for fixing the retractor (3) to the mandible (5). The positioning concave grooves (304F) and the positioning convex steps (302E) of the pull line fixing device form a concave-convex engagement, so as to prevent rotary movement of the pull line fixing device (302). The top cover (304G) includes a rotary positioning slot (304G1). The rotary positioning slot (304G1) may be elliptical or polygonal, into which a corresponding tool may be inserted in order to rotate the top cover (304G). The top cover seal ring (304B1) is used for sealing purpose to block human tissues from growing and penetrating into the main body (304L). The bottom cover (304H) includes an external thread for being engaged with the internal thread of the main body (304L) to tightly press the seal ring (304B), so as to achieve sealing. The bottom cover (304H) includes elliptical through holes, which may serve as the thread holes (304A) for the pull line (2) to pass through, and into which a corresponding tool may be inserted in order to rotate the bottom cover (304H), thereby facilitating assembly. The main body (304L) is used for mounting and fixing the control switch (301) and serves as a support for bearing the pull line fixing device (302). At the same time, a closed space may be formed to block human tissues from growing and penetrating into the main body (304L), thereby ensuring the adjustment function of the control switch (301).

The retractor (3) of a nut adjustment type shown in this embodiment has a reliable structure, has good sealing performance, can conveniently fix the pull line (2), is easily mounted onto the mandible, can be manufactured into small components, and is conveniently implanted into the human body.

Embodiment 15: A Retractor of a Nut Adjustment Type Having an Anti-Cutting Buffer Device of the Present Invention FIG. 15A to FIG. 15E, this embodiment is an improvement to Embodiment 14, where an anti-cutting buffer device (303) is added.

The anti-cutting buffer device (303) in this embodiment is four coil springs, where top ends of the four coil springs are connected to a binding plate (302C), and bottom ends of the four coil springs are mounted on spring positioning posts (302D) of the pull line fixing device (302).

The pull line (2) is bound to the binding plate (302C), and when the pull line (2) receives an excessive tension, the coil springs of the anti-cutting buffer device (303) deform, and the springs are compressed to eliminate the excessive tension, so as to prevent the pull plate (1) from cutting the soft tissues of the tongue.

The tension for causing deformation of the coil springs of the anti-cutting buffer device (303) is generally set to 100 g to 3000 g, and preferably 500 g to 1000 g, which may be set according to the maximum tensions of the tongues of different patients and the contact area between the pull plate (1) and the tongue base portion. The setting principle is that: under the maximum tension, the maximum pressure generated by the pull plate (1) is lower than the pressure when the soft tissues are cut, and is generally required to be smaller than 7000 g/cm$^2$.

The elastic force of the spring structure of the anti-cutting buffer device (303) is generally smaller than 1000 g, or the pressure generated on the pull plate (1) by the elastic force of the spring structure of the anti-cutting buffer device (303) is smaller than 7000 g/cm$^2$, and is preferably 500 g/cm$^2$ to 1500 g/cm$^2$. At this time, not only effective pulling to the tongue base (41) and/or the tongue dorsum (42) is maintained, but also injuries caused by cutting the tongue muscles are avoided.

Embodiment 16: A Push-Pull Type Retractor of the Present Invention

Referring to FIG. 16A to FIG. 16E, this embodiment shows a retractor (3) of a concave-convex engagement type. The control switch (301) of the retractor (3) adopts a concave-convex engagement structure, that is, positioning convex steps (301A) on the control switch (301) and positioning concave grooves (304F) on the inner side of the casing form a concave-convex engagement structure. A special tool is used to press an adjustment handle (301F) of the control switch (301) centripetally, so that the positioning convex steps (301A) detach from the positioning concave grooves (304F) on the inner side of the casing. The control switch (301) is pushed/pulled to drive the pull line fixing module (302) to move. After the stretching distance is adjusted, the adjustment handle (301F) is released, so that under the action of the elastic force, the positioning convex steps (301A) on the control switch (301) are engaged into the positioning concave grooves (304F) on the inner side of the casing, so as to form the concave-convex engagement structure, thereby achieving positioning. Specifically:

The retractor (3) includes a control switch (301) capable of adjusting a tension of the pull line (2), a pull line fixing module (302), and a casing (304). The control switch (301) of the retractor (3) adopts a push-pull adjustment manner, and when the adjustment handle (301F) of the control switch (301) is pressed, the positioning convex steps (301A) on the control switch detach from the positioning concave grooves (304F) on the inner side of the casing, and the control switch (301) can move leftward or rightward, so as to drive the pull line fixing module (302) to move leftward or rightward to achieve the objective of adjusting the pulling distance. When the adjustment handle (301F) is released, under the action of the elastic force, the positioning convex steps (301A) on the control switch (301) are engaged into the positioning concave grooves (304F) on the inner side of the casing, so as to form the concave-convex engagement structure, thereby achieving positioning.

The moving distance of the pull line fixing module (302) is generally 5 mm to 20 mm. The outer diameter of the retractor (3) is generally 1 mm to 10 mm, and preferably 2 mm to 6 mm.

The control switch (301) and the pull line fixing device (302) of the retractor of this embodiment are mounted in the retractor casing (304), so as to form a closed container.

The control switch (301) includes the positioning convex steps (301A) and the adjustment handle (301F) of the control switch. The adjustment handle (301F) is bent centripetally, so that the positioning convex steps (301A) detach from the positioning concave grooves (304F) on the inner side of the casing. Through pushing or pulling, the position of the control switch (301) can be adjusted. In addition, the control switch (301) is mounted in the pull line fixing device (302), and the positioning convex steps (301A) are engaged in positioning concave grooves (302G) of the pull line fixing device, so that the control switch (301) can drive the pull line fixing device (302) to move. The pull line fixing device (302) includes a binding plate (302C) for binding and fixing the pull line (2).

The retractor casing (304) includes thread holes (304A), a seal ring (304B), screw holes (304C), the positioning concave grooves (304F), a top cover seal ring (304B1), a top cover (304G), a bottom cover (304H) and a main body (304L). The thread holes (304A) are used for the pull line (2) to pass through. The seal ring (304B) is made of medical grade silica gel, and not only allows the pull line (2) to pass through, but also has a sealing function to block human tissues from growing and penetrating into the main body (304L). The screw holes (304C) are used for fixing the retractor (3) to the mandible (5). The positioning concave grooves (304F) on the inner side of the casing and the positioning convex steps (301A) on the control switch (301) form the concave-convex engagement structure, so as to achieve positioning during adjustment. The top cover (304G) includes a rotary positioning slot (304G1). The rotary positioning slot (304G1) may be elliptical or polygonal, into which a corresponding tool may be inserted in order to rotate the top cover (304G). The top cover seal ring (304B1) is used for sealing purpose to block human tissues from growing and penetrating into the main body (304L). The bottom cover (304H) includes an external thread for being engaged with the internal thread of the main body (304L) to tightly press the seal ring (304B), so as to achieve sealing. The bottom cover (304H) includes elliptical through holes, which may serve as the thread holes (304A) for the pull line (2) to pass through, and into which a corresponding tool may be inserted in order to rotate the bottom cover (304H), thereby facilitating assembly. The main body (304L) is used for mounting and fixing the control switch (301) and serves as a support for bearing the pull line fixing device (302). The positioning concave grooves (304F) on the inner side of the casing and the positioning convex steps (301A) on the control switch (301) form the concave-convex engagement structure, so as to achieve positioning during adjustment. At the same time, the casing (304) may form a closed space to block human tissues from growing and penetrating into the main body (304L), thereby ensuring the adjustment function of the control switch (301).

Embodiment 17: A Push-Pull Type Retractor Having an Anti-Cutting Buffer Device of the Present Invention Referring to FIG. 17A to FIG. 17E, this embodiment is an improvement to Embodiment 16. The difference lies in that: an anti-cutting buffer device (303) is added to the retractor (3).

The anti-cutting buffer device (303) in this embodiment is a corrugated spring plate, and the pull line (2) is bound and fixed to the corrugated spring plate. When the pull line (2) receives an excessive tension, the corrugated spring plate of the anti-cutting buffer device (303) deforms, and the spring plate is stretched straight to eliminate the excessive tension, so as to prevent the pull plate (1) from cutting the soft tissues of the tongue.

The tension for causing deformation of the corrugated spring plate of the anti-cutting buffer device (303) is generally set to 100 g to 3000 g, and preferably 500 g to 1000 g, which may be set according to the maximum tensions of the tongues of different patients and the contact area between the pull plate (1) and the tongue base portion. The setting principle is that: under the maximum tension, the maximum pressure generated by the pull plate (1) is lower than the pressure when the soft tissues are cut, and is generally required to be smaller than 7000 g/cm$^2$.

The elastic force of the spring structure of the anti-cutting buffer device (303) is generally smaller than 1000 g, or the pressure generated on the pull plate (1) by the elastic force of the spring structure of the anti-cutting buffer device (303) is smaller than 7000 g/cm$^2$, and is preferably 500 g/cm$^2$ to 1500 g/cm$^2$. At this time, not only effective pulling to the tongue base (41) and/or the tongue dorsum (42) is maintained, but also injuries caused by cutting the tongue muscles are avoided.

Embodiment 18: A Clutch-Type Retractor of the Present Invention

Referring to FIG. 18A to FIG. 18G, in this embodiment, the working principle of the control switch (301) of the retractor (3) adopts the principle of a clutch, and the pull line (2) is tightened or loosened by winding, which is specifically as follows:

The retractor (3) of this embodiment includes a control switch (301), a pull line fixing device (302), and a retractor casing (304). The casing (304) is a closed container, in which the control switch (301) and the pull line fixing device (302) are mounted.

The control switch (301) is a pair of concave and convex gears engaged with each other, and is formed by positioning convex steps (301A) on a convex gear (301A1) fixed to a top cover (304G) of the casing and positioning concave grooves (301B) on a concave gear (301B1) fixed to the top of the pull line fixing device (302). When the concave gear (301B1) is pressed, the positioning concave grooves (301B) and the positioning convex steps (301A) detach from one another, that is, a detached state is entered. The concave gear (301B1) is rotated to drive the shaft of the pull line fixing device (302) to rotate, so as to achieve the objective of tightening the pull line (2) or loosening the pull line (2). When the concave gear (301B1) is released, under the action of a spring (302H), the positioning concave grooves (301B) and the positioning convex steps (301A) are combined together, so that the shaft of the pull line fixing device (302) cannot rotate, thereby achieving positioning.

The pull line fixing device (302) is a rotary shaft structure. The concave gear (301B1) is disposed at the top of the pull line fixing device (302) to serve as a part of the control switch (301). A bobbin (302L) and a thread hole (302A) are provided in the middle of the pull line fixing device (302), where the bobbin (302L) is used for winding the pull line (2), and the thread hole (302A) is used for fixing the pull line (2). A spring positioning post (302D) is disposed at the bottom of the pull line fixing device (302), and is used for positioning the spring (302H).

The casing (304) is a cylindrical casing, having a side hole at the right side thereof. The casing (304) includes the top cover (304G) at the upper part thereof, where a silica gel plug (304D) may be mounted in a through hole (304G2) of the top cover (304G). After the silica gel plug (304D) is removed, a screwdriver may be used to press and rotate the concave gear (301B1); and after the silica gel plug (304D) is mounted, human tissues are blocked from growing and penetrating into the casing (304). The top cover (304G) includes the convex gear (301A1) at the lower part thereof, where the convex gear (301A1) and the concave gear (301B1) form a pair of concave and convex gears engaged with each other, and the positioning convex steps (301A) on the convex gear (301A1) and the positioning concave grooves (301B) on the concave gear (301B1) form the control switch (301). The top cover (304G) includes a pair of fixing lugs on a side surface thereof, and screw holes (304C) are formed on the fixing lugs. The main body (304L) of the casing (304) includes a pair of fixing lugs at the upper part thereof, and screw holes (304C) are formed on the fixing lugs, where the screw holes (304C) are used for connecting the top cover (304G) and the main body (304L), which may be fixed to the mandible by using screws. The main body (304L) includes a positioning slot for mounting the spring (302H) at the lower part thereof, where the spring (302H) is mounted in the positioning slot, with one end connected to the spring positioning post (302D) at the bottom part of the pull line fixing device (302). The main body (304L) has a side hole (304N) on a side surface thereof. The bottom cover (304H) is thread-connected to the main body (304L). The bottom cover (304H) has an elliptical thread hole (304A), and a seal ring (304B) can be fixed by tightening the bottom cover (304H). The pull line (2) is sequentially passed through the thread hole (304A) and the seal ring (304B), and after entering the side hole (304N) of the main body (304L), is wound onto the bobbin (302L), and the ends of the pull line (2) are fixed to the thread hole (304A). When the bobbin (302L) is rotated anticlockwise, the pull line (2) is tightened, and when the bobbin (302L) is rotated clockwise, the pull line (2) is loosened.

This embodiment shows a retractor (3) that is adjusted by winding, and has advantages such as reliable structure and convenient adjustment.

Embodiment 19: A Clutch-Type Retractor Having an Anti-Cutting Buffer Device of the Present Invention Referring to FIG. 19A to FIG. 19G, the difference between this embodiment and Embodiment 18 lies in the following aspects:

Firstly, an anti-cutting buffer device (303) is included. The anti-cutting buffer device (303) adopts a densely wrapped coil spring structure, is disposed in the casing (304), and mounted at a part of the pull line (2) that is located in the casing (304). Two ends of the densely wrapped coil spring of the anti-cutting buffer device (303) are respectively connected to the pull line (2), where the pull line (2) at one end is fixed to the thread hole (302A), and wound onto the bobbin (302L), and the other end is connected to the pull line (2), which is passed through the seal ring (304B) and the thread hole (304A), and then fixed to the pull plate (1).

Secondly, the side surface (304M) of the casing (304) has a flat plate shape, and the side hole (304N) is long, to which the bottom cover (304H) of the casing, the seal ring (304B), and a fixing nut (304I) are mounted sequentially.

Thirdly, the screw holes (304C) for fixing the casing (304) to the mandible are provided on the side surface (304M) of the casing, which facilitates mounting onto the mandible.

Embodiment 20: A Ratchet-Type Retractor of the Present Invention

Referring to FIG. 20A to FIG. 20D, the control switch (301) of this embodiment is a concave-convex engagement structure, where the control switch (301) is positioned through concave-convex engagement between a positioning convex step (301A) on a loosening switch (301D) and positioning concave grooves (301B) on a tightening switch (301C). Specifically:

The retractor (3) of this embodiment includes a control switch (301), a pull line fixing device (302), and a retractor casing (304). The casing (304) is a closed container, in which the control switch (301) and the pull line fixing device (302) are mounted. The control switch (301) is divided into a tightening switch (301C) and a loosening switch (301D).

The tightening switch (301C) adopts a ratchet structure. The tightening switch (301C) includes ratchet (301B2) at the bottom thereof, and the ratchet (301B2) includes positioning concave grooves (301B).

The loosening switch (301D) includes a positioning convex step (301A), and the positioning convex step (301A) and the positioning concave grooves (301B) on the ratchet form a concave-convex engagement. The positioning convex step (301A) includes a spring positioning post (301G) at the bottom thereof, and the spring positioning post (301G) is mounted with a spring (301E).

When the tightening switch (301C) is rotated clockwise, the pull line (2) is wound onto the bobbin (302L), and the positioning convex step (301A) on the loosening switch (301D) stops the bobbin (302L) from rotating back, so that the pull line (2) is tightened. When the loosening switch (301D) is pressed, the positioning convex step (301A) detaches from the engaged position, and the bobbin (302L) can rotate back, so as to loosen the pull line (2).

The pull line fixing device (302) is a shaft winding structure, where the bobbin (302L) includes a thread hole (302A). The thread hole (302A) is used for fixing the pull line (2), and the bobbin (302L) is used for winding the pull line (2). The bobbin (302L) is connected to the tightening switch (301C). When the tightening switch (301C) is rotated, the bobbin (302L) rotates along therewith.

The casing (304) is a cylindrical casing, having a side hole (304N) at the right side thereof, where the side hole (304N) has an internal thread, which can be engaged with an external thread of a bottom cover (304H). A seal ring (304B) and the bottom cover (304H) may be sequentially mounted to the side hole (304N). The pull line (2) is sequentially passed through a thread hole (304A) and, the seal ring (304B), and after entering the side hole (304N) of the main body (304L), is wound onto the bobbin (302L), and the ends of the pull line (2) are fixed to the thread hole (304A). When the bobbin (302L) is rotated clockwise, the pull line (2) is tightened, and when the bobbin (302L) is rotated anticlockwise, the pull line (2) is loosened.

The casing (304) includes a top cover (304G) at the upper part thereof, where a silica gel plug (304D) may be mounted in a through hole (304G2) of the top cover (304G). After the silica gel plug (304D) is removed, the tightening switch (301C) may be rotated to tighten the pull line (2); or the loosening switch (301D) may be pressed so that the tightening switch (301C) is in a loosened state, thereby loosening the pull line (2).

The top cover (304G) and the main body (304L) of the casing (304) may be fixed to each other by using screws or by welding. The casing (304) may be fixed to the mandible by using screws.

It should be particularly noted that, the silica gel plug (304D) may be manufactured into a color similar to that of the skin at the mandible of the human body, so that since titanium alloys have high biocompatibility, the top cover (304G) made of medical grade titanium metal of the casing can be exposed out of the skin at the mandible of the human body, and the silica gel plug (304D) that is manufactured into a color similar to that of the skin at the mandible of the human body has a beautifying function, and also facilitates adjusting the tension of the pull line (2) after surgery. For example, when adjustment is needed, the silica gel plug (304D) removed first, and after adjustment, the silica gel plug (304D) is mounted. The adjustment of the tension of the pull line (2) after surgery is based on the following principle:

In a non-sleep state, the loosening switch (301D) is pressed so as to adjust the control switch (301) to an "off" state, and at this time, the pull lines (2) apply a small pulling force to the tongue base portion or are completely in a loosened state, and the tongue is capable of moving freely during speaking, swallowing and other activities.

Before sleep, the tightening switch (301C) is tightened so as to adjust the control switch (301) to an "on" state, and at this time, a large pulling force is applied to the tongue base portion, so that the tongue base portion is in an effective retracted state, and the tongue base portion is pulled forward, so as to maintain the palatopharyngeal portion open, thereby preventing OSAHS.

Embodiment 21: A Single-Switch Push-Pull Type Retractor of the Present Invention Referring to FIG. 21A to FIG. 21K, this embodiment shows a button-type single-switch push-pull retractor, which is particularly suitable for being mounted at the bottom portion of the mandible to retract the tongue dorsum (42) and/or the tongue base (41) so as to treat OSAHS, and allows the patient to adjust the pulling degree of the tongue from a position outside the skin at the bottom portion of the mandible after surgery, so as to achieve good comfort.

This embodiment shows a retractor (3), in which after the control switch (301) is pressed, the position of the pull line fixing device (302) can be conveniently adjusted by pushing or pulling, so as to tighten or loosen the pull line (2); and once the control switch (301) is released, the control switch (301) can be automatically locked and positioned.

The retractor (3) of this embodiment includes a control switch (301), a pull line fixing device (302), and a retractor casing (304). The casing (304) is a closed container, in which the control switch (301) and the pull line fixing device (302) are mounted.

The control switch (301) is a concave-convex engagement structure formed by a beam-type positioning convex step (301A) and a tooth rack-type positioning concave groove (301B), specifically:

The control switch (301) includes a beam-type positioning convex step (301A), and the beam-type positioning convex step (301A) is provided on the pull line fixing device (302) and connected to an adjustment handle (301F). The pull line fixing device (302) includes a thread hole (302A) and a bolt (302I) for fixing the pull line (2). The pull line fixing device (302), the pull line fixing bolt (302I), the beam-type positioning convex step (301A), the adjustment handle (301F), a spring (301E) and a positioning slide-block cover (302M1) are sequentially mounted in a positioning slide block (302M), and can slide in a positioning slot opening (304P) and a positioning concave groove (304F) of the casing as a whole.

The tooth rack-type positioning concave groove (301B) of the control switch (301) is provided on the casing (304), and two tooth racks (301B3) are symmetrically distributed in parallel at the upper part of the main body (304L). The positioning slide block (302M) of the pull line fixing device can slide in the positioning slot opening (304P) between the two tooth racks (301B3).

The pull line fixing device (302) includes a thread hole (302A) and a fixing bolt (302I) for fixing the pull line. The pull line (2) is passed through the thread hole (302A), and the fixing bolt (302I) is tightened, so as to fix the pull line (2). The pull line fixing device (302) further includes a positioning slide block (302M), where the positioning slide block (302M) is a rectangular casing. The positioning slide block (302M) includes a positioning slide-block cover (302M1) and a positioning slide-block slot opening (302M2). The adjustment handle (301F), the spring (301E), the thread hole (302A) and the fixing bolt (302I) are sequentially mounted in the positioning slide block (302M). The beam-type positioning convex step (301A) of the control switch (301) is passed through the positioning slide-block slot opening (302M2), and is capable moving vertically in a direction perpendicular to the positioning slide-block slot opening (302M2).

The retractor casing (304) includes a main body (304L), and the main body (304L) includes a vertical fixing plate (304L1) and a horizontal fixing plate (304L2). The vertical fixing plate (304L1) and the horizontal fixing plate (304L2) each includes screw holes (304C), and the screw holes (304C) are used for fixing the retractor casing (304) to the mandible (5) by using screws (10). The main body (304L) further includes two symmetrical tooth racks (301B3), and a positioning slot opening (304P) is formed between the two tooth racks (301B3). The positioning slot opening (304P) is engaged with the positioning slide block (302M) of the pull line fixing device, so that the positioning slide block (302M) is capable of sliding back and forth along the length direction of the positioning slot opening (304P).

The retractor casing (304) includes a top cover (304G), and the top cover (304G) includes a positioning concave groove (304F). The positioning concave groove (304F) cooperates with the positioning slot opening (304P) in the vertical direction so as to achieve spatial positioning. The positioning slide block (302M) is disposed on the positioning concave groove (304F), and is capable of moving back and forth along the length direction of the positioning slot opening (304P) and the length direction of the positioning concave groove (304F).

The retractor casing (304) further includes a top cover seal ring (304B1) and a fixing plate (304B2) for fixing the top cover seal ring. The top cover seal ring (304B1) is made of a medical film material, and therefore is soft and durable. The fixing plate (304B2) is used for fixing the top cover seal ring (304B1), and the fixing plate (304B2) is fixed to the main body (304L) by means of close fit or using a screw. The fixing plate (304B2) includes a thread hole (304A) for the pull line (2) to pass through.

The retractor (3) of the present invention can be fixed to the mandible by using screws.

It is particularly important that when the retractor (3) of the present invention is used to retract the tongue dorsum portion and/or the tongue base portion, the patient can adjust the pulling degree of the pull line (2) to the tongue dorsum portion and/or the tongue base portion after surgery by pressing the control switch (301) from a position outside the bottom portion of the mandible of the patient and at the same time pushing or pulling the control switch (301). The adjustment is based on the following principle:

In a non-sleep state, the control switch (301) is pressed and pushed toward the tongue base portion so that the pull lines (2) apply a small pulling force to the tongue base portion or are completely in a loosened state, and then the control switch (301) is released so that the control switch (301) is automatically positioned and locked, that is, the control switch (301) is adjusted to an "off" state, and at this time, the tongue base portion is almost unconstrained, and the tongue is capable of moving freely during speaking, swallowing and other activities.

Before sleep, the control switch (301) is pressed and pulled toward the mandible so that the control switch (301) is adjusted to an "on" state, and at this time, the pull lines (2) apply a large pulling force to the tongue base portion, so that the tongue base portion is in an effective retracted state, and the tongue base portion is pulled forward, so as to maintain the palatopharyngeal portion open, thereby preventing OSAHS.

A degree of comfort is set. To avoid daily adjustment, the control switch (301) may be pressed and pulled toward the mandible, and then released at a proper position, so that the pull line (2) applies a proper pulling force to the tongue base portion, so as to move the tongue base portion forward while ensuring comfort during movement of the tongue, and maintain the palatopharyngeal portion open, thereby preventing OSAHS.

Embodiment 22: A Double-Button Ratchet-Type Retractor of the Present Invention

Referring to FIG. 22A to FIG. 22Q, this embodiment shows a double-button ratchet-type retractor, which is particularly suitable for being mounted at the front portion of the mandible to retract the tongue dorsum (42) and/or the tongue base (41) so as to treat OSAHS, and allows the patient to adjust the pulling degree of the tongue by pressing a switch from a position outside the skin at the bottom portion of the mandible after surgery, so as to achieve good comfort.

This embodiment shows a double-button ratchet-type retractor (3), which has the following characteristics:

The control switch (301) is divided into a tightening switch (301C) and a loosening switch (301D), and adopts a ratchet (301B2) as an adjustment structure. Each time when the tightening switch (301C) is pressed, a positioning convex step (301A) on the tightening switch (301C) pushes the ratchet (301B2) to rotate by one step, so as to drive the pull line fixing device (302) to move to tighten the pull lines (2). A positioning convex step (301A) on the loosening switch (301D) is used for stopping reverse rotation of the ratchet (301B2), so as to prevent loosening of the tightened pull lines (2). When the loosening switch (301D) is pressed, the ratchet (301B2) is released, so that the ratchet (301B2) is in a free state, which drives the pull line fixing device (302) to enter a loosened state, thereby loosening the pull line (2).

Specifically, this embodiment the retractor (3) includes a control switch (301), a pull line fixing device (302), and a retractor casing (304).

The control switch (301) is divided into a tightening switch (301C) and a loosening switch (301D). Both the tightening switch (301C) and the loosening switch (301D) adopt a pushrod structure, and a spring (301E) is used for restoring the pushrod. The tightening switch (301C) and the loosening switch (301D) each include a positioning convex step (301A), where the positioning convex step (301A) adopts a reed structure. The positioning convex step (301A) on the tightening switch (301C) includes a wedge-shaped slide block (301A1) and a spring (301E1), where the spring (301E1) is mounted on the wedge-shaped slide block (301A1). The positioning convex step (301A) on the loosening switch (301D) includes a wedge-shaped slide block (301A2) and a spring (301E2), where the spring (301E2) is mounted on the wedge-shaped slide block (301A2).

Tighten the Pull Line:

Each time when the tightening switch (301C) is pressed, the positioning convex step (301A) on the tightening switch (301C), that is, the wedge-shaped slide block (301A1), pushes the ratchet (301B2) to rotate by one step, so as to drive the pull line fixing device (302) to move to tighten the pull lines (2). The positioning convex step (301A) on the loosening switch (301D), that is, the wedge-shaped slide block (301A2), is used for stopping reverse rotation of the ratchet (301B2), so as to prevent loosening of the tightened pull lines (2).

Loosen the Pull Line:

When the loosening switch (301D) is pressed, the positioning convex step (301A) on the loosening switch (301D) detaches from the ratchet (301B2), that is, the wedge-shaped slide block (301A2) detaches from the ratchet (301B2), and the ratchet (301B2) is released from the wedge-shaped slide block (301A2), so that the ratchet (301B2) is in a free state, which drives the pull line fixing device (302) to enter a loosened state, thereby loosening the pull line (2).

The pull line fixing device (302) includes a thread hole (302A), a pull line fixing bolt (302I), and a bobbin (302L). The pull line (2) is passed through the thread hole (302A) and fixed by the pull line fixing bolt (302I), and may be wound onto the bobbin (302L). The pull line fixing device (302) is connected to the ratchet (301B2) of the control switch (301), and the ratchet (301B2) of the control switch (301) is rotated to drive the bobbin (302L), thereby winding or loosening the pull line (2).

The retractor casing (304) is used for fixing and mounting the control switch (301) and the pull line fixing device (302), and includes a main body (304L), a top cover (304G), screws (304J), a thread hole (304A), a silica gel film (304K), a seal ring (304B), a casing side plate (304L1), and screw holes (304C). The control switch (301) and the pull line fixing device (302) are mounted in the retractor casing (304). The top cover (304G) is fixed to the main body (304L) by using the screws (304J). The pull line (2) is passed through the thread hole (304A) and the seal ring (304B), and then fixed into the thread hole (302A) of the pull line fixing device (302) by the pull line fixing bolt (302I). Buttons of the tightening switch (301C) and the loosening switch (301D) are wrapped by the silica gel film (304K), and the silica gel film (304K) and the seal ring (304B) are fixed to the main body (304L) by the casing side plate (304L1). The screw holes (304C) are used for fixing the retractor casing (304) to the mandible (5).

Fast Loosening of the Pull Line:

To achieve fast loosening of the ratchet (301B2), a restoring spring (305) may further be mounted. The restoring spring (305) is a coil spring, which may provide a force for driving reverse rotation of the ratchet (301B2), so that the ratchet (301B2) reversely rotates rapidly, and drives the pull line fixing device (302) to enter a loosened state, thereby achieving fast loosening of the pull line (2). The restoring spring (305) has one end fixed to the bobbin (302L) and the other end fixed to the main body (304L). Each time when the tightening switch (301C) is pressed, the ratchet (301B2) is pushed to rotate by one step, so as to gradually compress the restoring spring (305), and the restoring spring (305) gradually stores elastic deformation energy. When the loosening switch (301D) is pressed, the positioning convex step (301A) on the loosening switch (301D) detaches from the ratchet (301B2) to release the ratchet (301B2), so that the force restricting the compressed restoring spring (305) is removed, and the elastic energy stored by the restoring spring (305) is released, so as to drive reverse rotation of the pull line fixing device (302), thereby achieving fast loosening of the pull line (2). Refer to FIG. 22E, FIG. 22F and FIG. 22H.

Fast Mounting of the Pull Line:

To enable the doctor to conveniently mount this product, the retractor (3) may further be provided with a protective sheath (306). The protective sheath (306) is a thin wall tube made of a medical flexible material, and is mounted in the retractor casing (304), and sequentially passed through the thread hole (304A) and the seal ring (304B) on the casing, the thread hole (302A) on the pull line fixing device, the top cover seal ring (304B1) of the casing, and a through hole (304A1) on a nut for fixing the top cover seal ring of the casing. The pull line (2) may be passed along the protective sheath (306), which not only provides a routing function, but also protects the pull line (2). Refer to FIG. 22J to FIG. 22P.

During mounting, first, the retractor (3) is fixed to the lower part of the mandible (5), and tightened by using screws. Then, one end of each of four pull lines (2) is fixed to a corresponding one of four corners of the pull plate (1). Next, a surgical knife is used to incise the mucous membrane of the tongue base portion, and the pull plate (1) is implanted into the muscular layer under the mucous membrane layer of the tongue base portion and/or the tongue dorsum portion of the human body. A special surgical retractor is penetrated into the tongue body from a position close to the mandible (5), and the four pull lines (2) are respectively drawn to the vicinity of the mandible (5) by using the surgical retractor. The pull lines (2) are guided into the protective sheath (306) from the bottom end of the protective sheath (306), and then drawn out from the top end of the protective sheath (306). The pull lines (2) are properly tightened so as to maintain effective pulling to the tongue base portion. The pull lines (2) drawn out from the top end of the protective sheath (306) is tied, and then the protective sheath (306) and the pull lines (2) are properly pulled downward, so that the protective sheath (306) and the pull lines (2) enter the casing (304) of the retractor. Finally, the pull line fixing bolt (302I) is tightened to fix the pull lines (2) to the thread hole (302A) of the pull line fixing device, thus completing the whole mounting process. The surgical incisions are sutured, thus completing the surgical operation. Refer to FIG. 22J to FIG. 22P.

Embodiment 23: A Double-Button Ratchet Thread-Type Retractor of the Present Invention Referring to FIG. 23A to FIG. 23D, this embodiment is basically the same as the technical solution of Embodiment 22. In Embodiment 22, the pull line fixing device (302) connected to the ratchet (301B2) being the core component of the control switch (301) of the retractor is the bobbin (302L), the pull line (2) is wound onto the bobbin (302L), and the rotation of the bobbin (302L) is controlled by controlling the rotation of the ratchet (301B2), so as to control the tightening and loosening degrees of the pull line (2). In this embodiment, the difference lies in that: the pull line fixing device (302) connected to the ratchet (301B2) being the core component of the control switch (301) of the retractor is a thread-bolt structure, and the position of the binding plate (302C) on the thread-bolt structure is controlled through rotation of the ratchet (301B2), so as to adjust the tightening degree or loosening degree of the pull line (2).

Figure 24A:
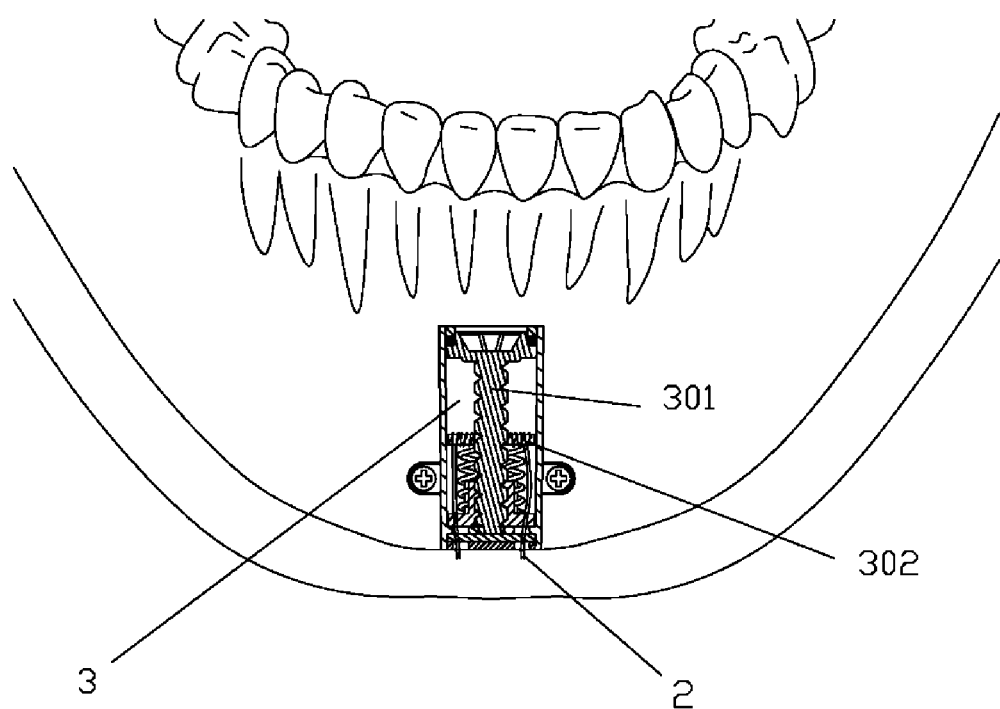
FIG. 24A is a schematic structural view of a tongue pulling device in which a retractor of a bolt adjustment type is mounted to the anterior part of the mandible according to the present invention.
Figure 24B:
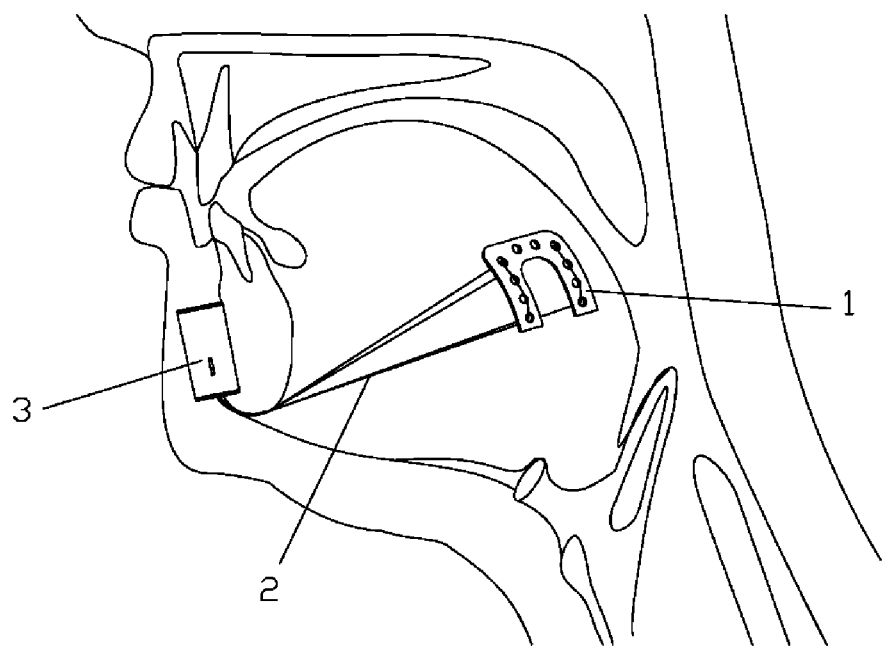
FIG. 24B is a schematic mounting view of the tongue pulling device of FIG. 24A.
Figure 24C:
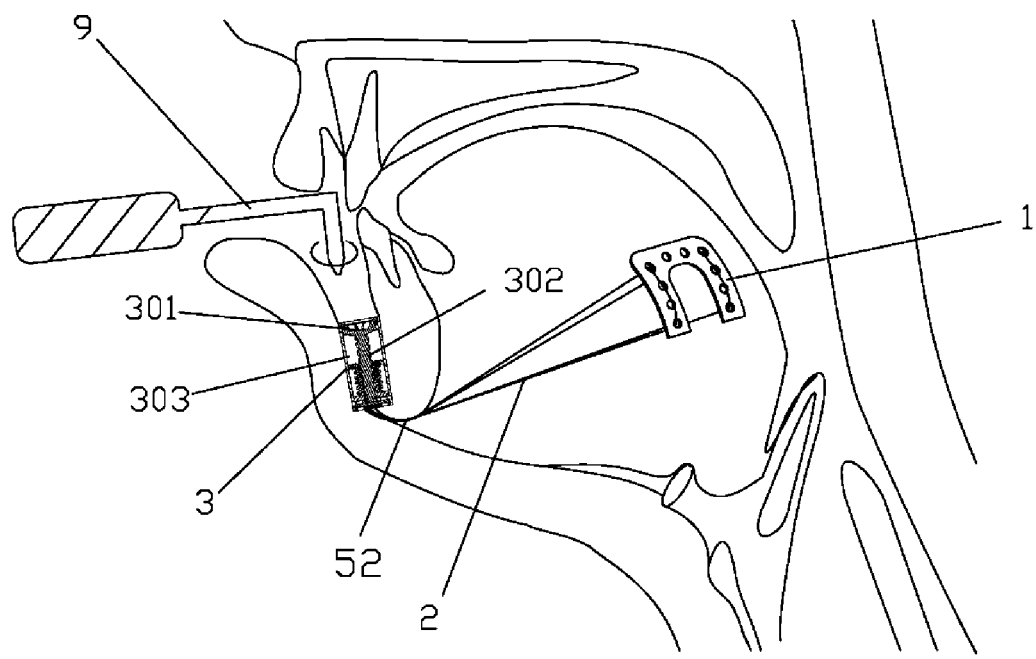
FIG. 24C is a view depicting the working principle of adjusting the tongue pulling device of FIG. 24A by using a screwdriver.

Embodiment 24: A Tongue Pulling Device of the Present Invention that is Adjusted by the Patient from a Position Between the Lower Lip and the Lower Teeth after Surgery Referring to FIG. 24A to FIG. 24C, a tongue pulling device of the present invention that is adjusted by the patient from a position between the lower lip and the lower teeth after surgery is shown.

The tongue pulling device of the present invention is mounted on the front surface of the mandible and close to the bottom portion of the mandible, so that the control switch (301) of the adjusted retractor faces upward. In this way, after surgery, the lower lip is pulled apart, and a screwdriver (9) is inserted into a cross slot of the control switch (301) to rotate the bolt that serves as the control switch (301), so as to tighten or loosen the pull line (2).

Adjustment can be carried out from a position between the lower lip and the lower teeth, a small surgical wound is created, the appearance of the patient is not affected, and adjustment by the patient is facilitated.

Figure 25A:
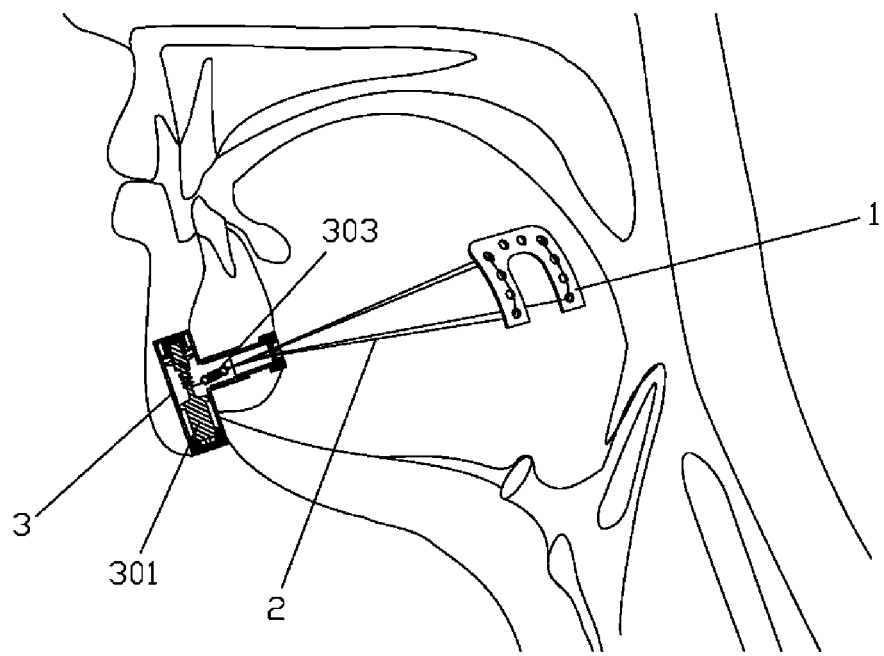
FIG. 25A is a schematic mounting view of a winding clutch-type tongue pulling device according to the present invention.
Figure 25B:
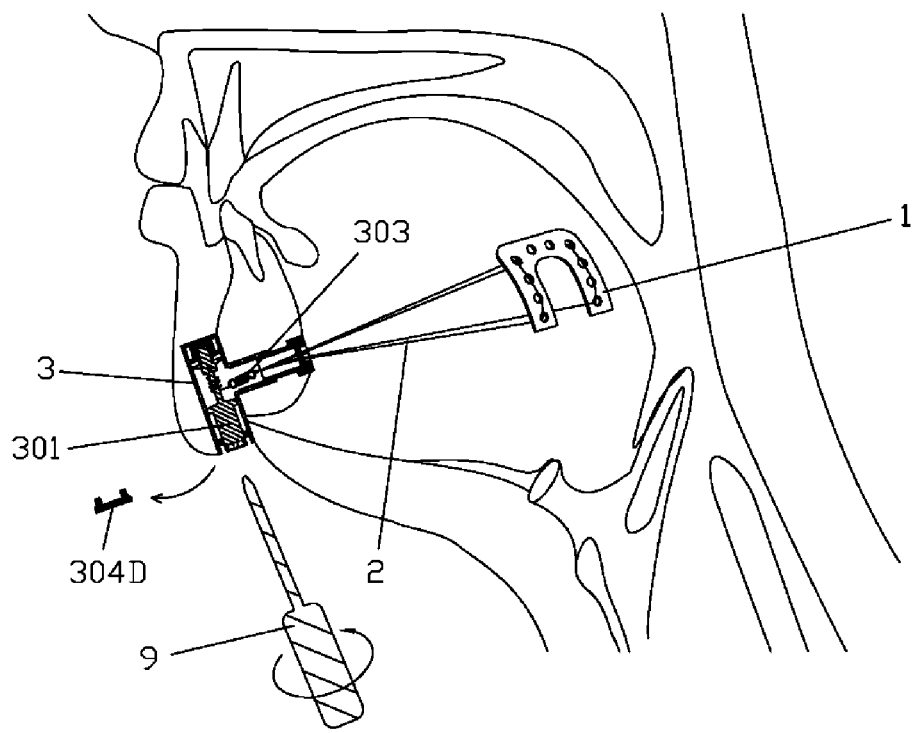
FIG. 25B is a view depicting the working principle of adjusting the tongue pulling device of FIG. 25A.

Embodiment 25: A Tongue Pulling Device of the Present Invention that is Adjusted by the Patient from the Bottom Portion of the Mandible after Surgery Referring to FIG. 25A and FIG. 25B, a tongue pulling device of the present invention that is adjusted by the patient from the bottom portion of the mandible after surgery is shown.

The tongue pulling device of the present invention is mounted on the front surface of the mandible and close to the bottom portion of the mandible. The silica gel plug (304D) of the casing of the tongue pulling device of the present invention is outside the skin at the bottom portion of the mandible, and has the same color as that of the skin at the bottom portion of the mandible. The silica gel plug (304D) is removed, and the screwdriver (9) is used to press the control switch (301) upward and at the same time rotate the control switch (301), so as to tighten or loosen the pull line (2) to adjust the tension of the pull line (2), thereby controlling the pulling degree of the tongue base portion and/or the tongue dorsum portion.

Figure 26A:
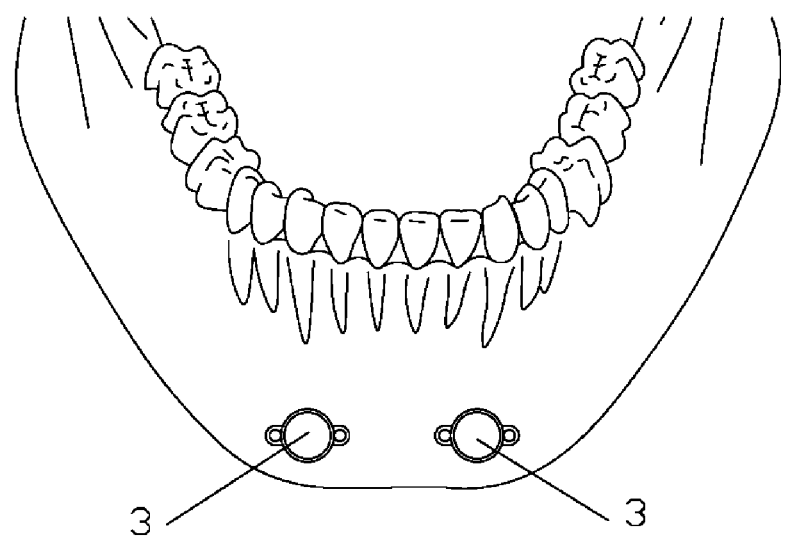
FIG. 26A is a schematic mounting view of a double-retractor tongue pulling device according to the present invention.
Figure 26B:
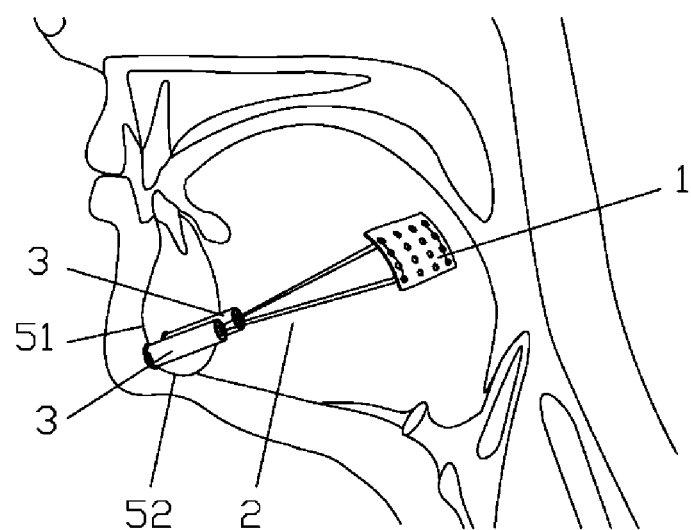
FIG. 26B is a schematic structural view of a double-retractor tongue pulling device according to the present invention.

Embodiment 26: A Double-Retractor Tongue Pulling Device of the Present Invention Referring to FIG. 26A and FIG. 26B, a double-retractor tongue pulling device of the present invention is shown.

In this embodiment, the difference lies in that: two retractors (3) are mounted on the front portion of the mandible and close to the bottom portion of the mandible, and the distance between the two retractors (3) is about 10 mm to 25 mm. At this time, retractors (3) having a small diameter and having an anti-cutting buffer device (303) are generally used, so as to achieve the objective of minimal invasive treatment.

Embodiment 27: A Tongue Pulling Device Having a Combined-Type Pull Plate of the Present Invention Refer to FIG. 27A to FIG. 27I. The difference between this embodiment and Embodiment 1 lies in that: the pull plate (1) of Embodiment 1 is formed by a titanium metal plate subjected to a metal stamping manufacturing process, and is one component; while in this embodiment, the pull plate (1) is formed by two components, that is, the pull plate (1) of the present invention is divided into a left-side pull plate (109A) and a right-side pull plate (109B), where the left-side pull plate (109A) is assembled to the right-side pull plate (109B) through a mechanical connection mechanism (109E). After the left-side pull plate (109A) is assembled to the right-side pull plate (109B), a gap (109C) and junctions (109D) are formed between the left-side pull plate (109A) and the right-side pull plate (109B).

The gap (109C) is required to provide such a space that can maintain normal survival and tension of the tongue tissues in the gap, particularly, continuity of musculus genioglossus and other fibrous tissues to the fibrous tissues under the mucous membrane of the tongue dorsum or the tongue base, which on one hand reduces the wound, and on the other hand increases the pulling force to the tongue dorsum (42) and/or the tongue base (41). The maximum width (H109) of the gap (109C) is 1 mm to 10 mm, and preferably 2 mm to 5 mm. The length (L109) of the gap (109C) is 5 mm to 20 mm, and preferably 5 mm to 15 mm.

The mechanical connection mechanism (109E) is a mechanical fixing mechanism capable of fixing two metal plates, and is for example a rivet structure, a concave-convex engagement structure, a thread fixing structure or other mechanical fixing mechanisms. In this embodiment, the rivet structure is adopted. Titanium metal rivets (109E1) are used at the junctions (109D) between the left-side pull plate (109A) and the right-side pull plate (109B) to rivet the left-side pull plate (109A) to the right-side pull plate (109B).

The pull line (2) has one end fixed to the pull line fixing structure (102) so as to be connected to the pull plate (1), and the other end fixed to the retractor (3) so as to be connected to the retractor (3). The four pull lines (2) spatially position the pull plate (1). Meanwhile, the left-side pull plate (109A) and the right-side pull plate (109B) are combined through the rivets (109E1), and fibrous tissues of the tongue muscles are sandwiched in the gap (109C) between the left-side pull plate (109A) and the right-side pull plate (109B). Through the gap (109C), the continuity of musculus genioglossus and other fibrous tissues to the fibrous tissues under the mucous membrane of the tongue dorsum or the tongue base is maintained. On one hand, the wound is reduced. On the other hand, since the rivets (109E1) are inserted for fixing, and fibrous tissues of musculus genioglossus are sandwiched between the left-side pull plate (109A) and the right-side pull plate (109B), the capability of spatially positioning the pull plate (1) is further improved, thereby effectively preventing shifting of the pull plate (1); and the pulling force to the tongue dorsum (42) and/or the tongue base (41) is increased.

Surgical Method for Treating OSAHS in this Embodiment:

A surgical method for implanting the tongue pulling device of the present invention mainly includes the following steps:

Firstly, surgical sites such as the tongue and the oral cavity are disinfected under anesthesia according to general requirements of oral cavity, head and neck surgeries.

Secondly, fixing one end of each of two pull lines to a left-side pull plate (109A), and fixing one end of each of another two pull lines to a right-side pull plate (109B); then, using a surgical knife to make incisions of about 3 mm to 6 mm at a position about 10 mm to 15 mm from circumvallate papillae of the tongue and beside two sides of the midline of the tongue, and of about 8 mm transversely cutting the mucous membrane of the tongue, and using a moderately curved hemostatic forceps to separate the mucous membrane toward the tongue base, so as to form an about 40 mm deep surgical cavity on left and right sides of the midline of the tongue respectively; using a special surgical forceps (13) to simultaneously insert the left-side pull plate (109A) and the right-side pull plate (109B) into the surgical cavities below the mucous membrane of the tongue dorsum (42) and/or the tongue base (41) to be retracted; during insertion, a distance between the left-side pull plate (109A) and the right-side pull plate (109B) is maintained at 1 mm to 10 mm; at the same time, the left-side pull plate (109A) and the right-side pull plate (109B) are maintained symmetrical; and thirdly, closing the special surgical forceps (13), and assembling and fixing the left-side pull plate (109A) to the right-side pull plate (109B) through a mechanical connection mechanism (109E); fibrous tissues of the tongue muscles are sandwiched in a gap (109C) between the left-side pull plate (109A) and the right-side pull plate (109B), and through the gap (109C), continuity of musculus genioglossus and other fibrous tissues to the fibrous tissues under the mucous membrane of the tongue dorsum or the tongue base is maintained.

Thirdly, the pull lines (2) are drawn to the vicinity of the mandible (5) by using a guide needle.

Fourthly, an incision is made along the lower lip to expose the mandible (5), the retractor (3) is fixed to the mandible (5), and at the same time, the pulling lengths of the four pull lines (2) are adjusted respectively, and all the four pull lines (2) are fixed to the retractor (3).

Fifthly, the incisions are sutured, thus completing the surgery.

The Tongue Pulling Device Having the Combined-Type Pull Plate of the Present Invention has the Following Advantages:

With the use of the flat pull plate (1), the contact area between the pull plate (1) and the retracted portion of the tongue body is increased, so that the pressure generated during pulling is greatly reduced, which not only improves the pulling effect, but also avoids cutting the tongue tissues when the tongue body is retracted, thereby reducing injuries. Particularly, with the use of the combined-type pull plate (1) formed by the left-side pull plate (109A) and the right-side pull plate (109B), continuity of musculus genioglossus and other fibrous tissues to the fibrous tissues under the mucous membrane of the tongue dorsum or the tongue base is maintained to the maximum extent, thereby further enhancing the capability of spatially positioning the pull plate (1) and improving the effect of retracting the tongue dorsum (42) and/or the tongue base (41).

Secondly, with the use of the spatial pulling mode with four pull lines (2), shifting of the pull plate (1) after implantation is effectively prevented. Particularly, after the combined-type pull plate (1) formed by the left-side pull plate (109A) and the right-side pull plate (109B) is used, rivets (109E1) for fixing the left-side pull plate (109A) and the right-side pull plate (109B) are inserted into musculus genioglossus, which further improves the stability of the pull plate (1) so that the pull plate (1) does not easily displace.

Thirdly, the retractor (3) is conveniently fixed to the mandible (5), and the pull lines (2) are fixed to the retractor (3), so that the pulling degree of the pull lines (2) can be conveniently adjusted to accurately control the pulling distance and the pulling force, thereby achieving an optimal therapeutic effect. Particularly, when the double-button type retractor (3) that can be adjusted after surgery is used, not only the doctor can conveniently adjust and fix the pull lines (2) during surgery, but also woundless adjustment can be achieved after surgery.

Embodiment 28: A Tongue Pulling Device Having a U-Shaped Combined-Type Pull Plate of the Present Invention Refer to FIG. 28A to FIG. 28K. The difference between this embodiment and Embodiment 27 lies in the following aspects.

Figure 27B:
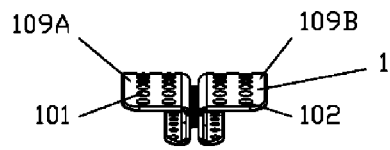
FIG. 27B is a side view of FIG. 27A.
Figure 27C:
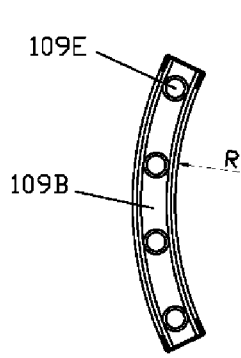
FIG. 27C is a left view of FIG. 27A.
Figure 27A:
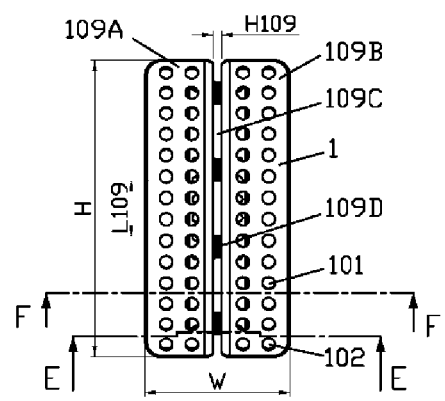
FIG. 27A is a schematic structural view of a combined-type pull plate according to the present invention.
Figure 27D:
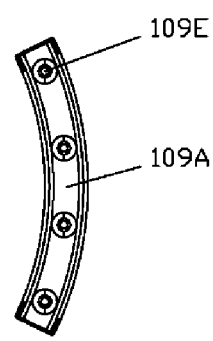
FIG. 27D is a right view of FIG. 27A.
Figure 27E:
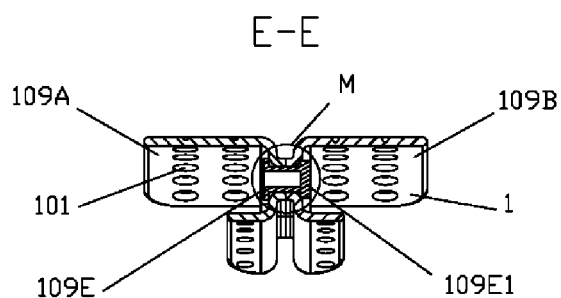
FIG. 27E is an E-E cross-sectional view of FIG. 27A.
Figure 27F:
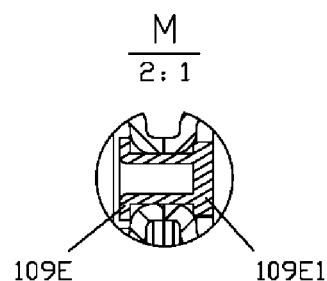
FIG. 27F is an F-F cross-sectional view of FIG. 27A.
Figure 27F:
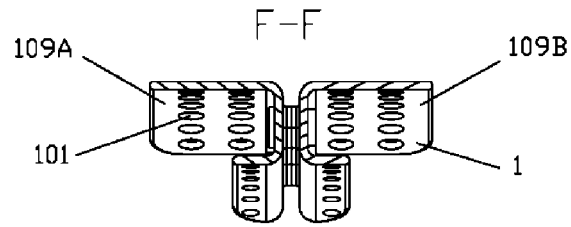
Figure 27G:
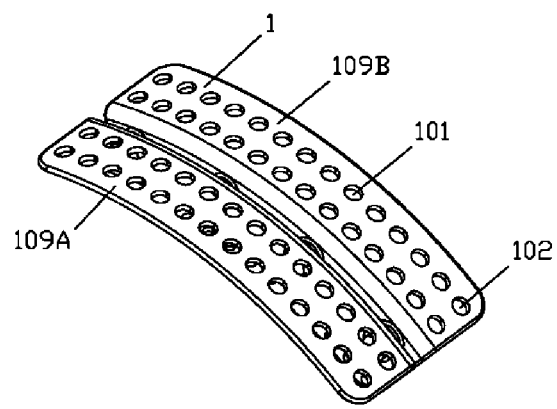
FIG. 27G is a three-dimensional schematic structural view of FIG. 27A.
Figure 27H:
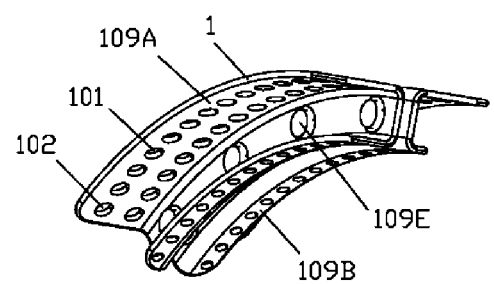
FIG. 27H is a three-dimensional schematic structural view of the back side of FIG. 27G.

The left-side pull plate (109A) and the right-side pull plate (109B) of this embodiment have a U-shaped cross section, as shown in FIG. 28E and FIG. 28F; while the left-side pull plate (109A) and the right-side pull plate (109B) of Embodiment 27 have an L-shaped cross section, as shown in FIG. 27E and FIG. 27F.

Figure 27I:
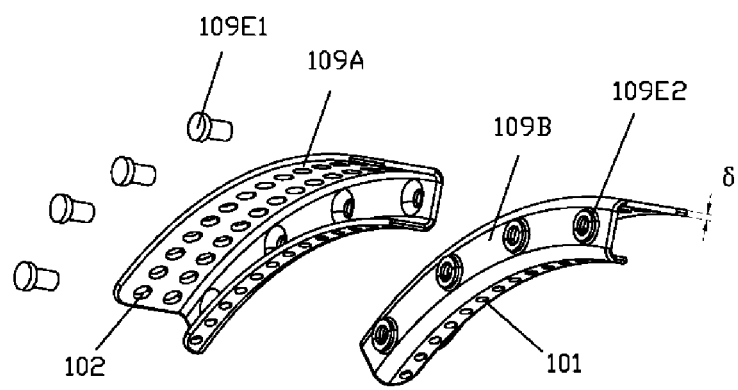
FIG. 27I is an exploded view of FIG. 27H.
Figure 27J:
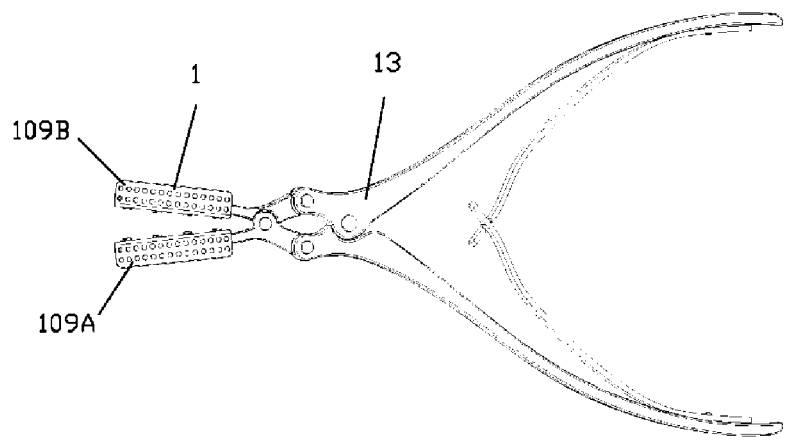
FIG. 27J is a schematic structural view depicting that the left-side pull plate and right-side pull plate of FIG. 27A are respectively mounted at jaws of a surgical forceps.
Figure 27K:
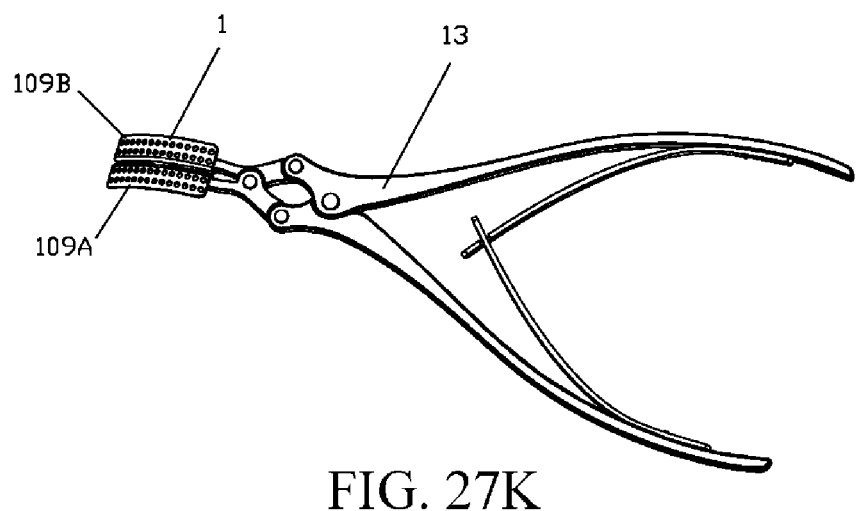
FIG. 27K is a schematic structural view of combining the left-side pull plate and right-side pull plate by using the special surgical forceps of FIG. 27J.
Figure 27L:
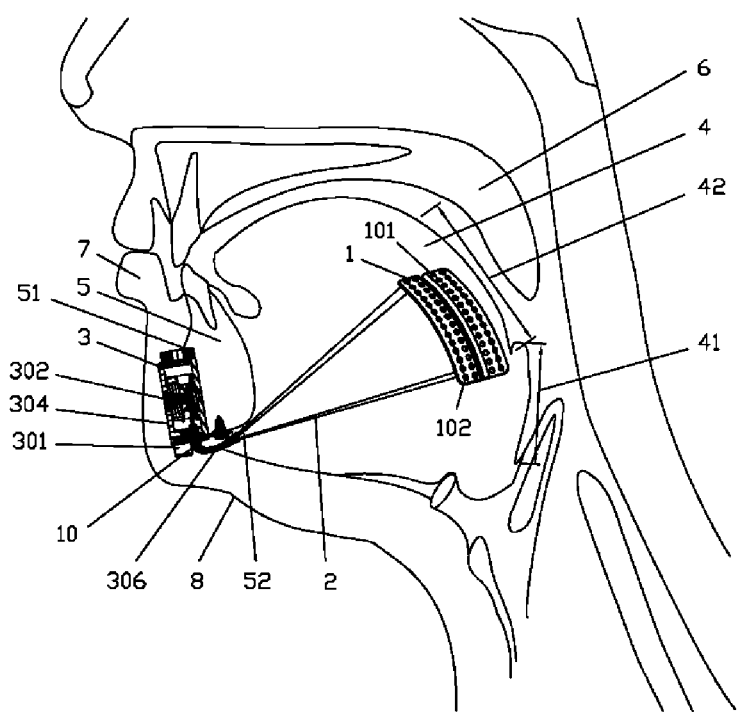

Secondly, in this embodiment, the mechanical connection mechanism (109E) between the left-side pull plate (109A) and the right-side pull plate (109B) adopts a concave-convex engagement structure, where convex steps on the lock screw (109E4) and a concave groove on a lock nut (109E3) form the concave-convex engagement structure, as shown in FIG. 28E, FIG. 28E1 and FIG. 28J; while the rivet structure is adopted in Embodiment 27, as shown in FIG. 27E, FIG. 27E1 and FIG. 27I.

In addition, the gap (109C) formed between the left-side pull plate (109A) and the right-side pull plate (109B) in this embodiment is accomplished through corresponding curvatures of assembled edges of the left-side pull plate (109A) and the right-side pull plate (109B), as shown in FIG. 28A, FIG. 28G and FIG. 28H; while in Embodiment 27, it is adjusted through the height of rivet posts (109E2) of the rivet structure, as shown in FIG. 27I.

Embodiment 29: A Pull Line Formed by Spirally Braided Wires of the Present Invention This embodiment shows a pull line (2) of the present invention, which, as shown in FIG. 29, is different from Embodiment 10 in that: the pull line (2) is formed by spirally braiding a plurality of metal wires having a diameter of 0.1 mm to 0.5 mm. In this embodiment, it is specifically formed by spirally braiding five titanium-nickel shape memory alloy (Nitinol alloy) wires having a diameter of 0.2 mm. The metal wires of such a small cable structure of braided Nitinol alloy wires not only have high biocompatibility, but also have a large tensile strength and high fatigue resistance, and therefore are suitable for manufacturing the pull line (2) of the present invention.

Embodiment 30: A Composite Pull Line of a Corrugated Tube Type of the Present Invention Referring to FIG. 30A, this embodiment shows a composite pull line (2) of a corrugated tube type of the present invention, and is different from Embodiment 29 and Embodiment 10 in that: a spiral line formed by spirally braiding a plurality of metal wires is used as the draw line (201), and a corrugated tube is used as the sleeve (202), so as to form a composite pull line (2). The corrugated tube used as the sleeve (202) may be continuous; or may be discontinuous, and sleeved on the draw line (201) in segments, as shown in FIG. 30B.

The corrugated tube in this embodiment may be made of a medical metal material or a medical polymer material. Metal corrugated tubes include titanium and titanium alloy corrugated tubes, medical grade stainless steel corrugated tubes and the like. The corrugated tubes of medical polymer materials include medical grade polytetrafluoroethylene corrugated tubes, medical grade terylene corrugated tubes, medical grade polythene corrugated tubes, medical grade polyurethane corrugated tubes and the like.

Embodiment 31: A Composite Pull Line of a Coil Spring Tube Type of the Present Invention Referring to FIG. 31A, this embodiment shows a composite pull line (2) of a coil spring tube type of the present invention, which is different from Embodiment 30 and Embodiment 10 in that: the sleeve (202) is a coil spring tube. The coil spring tube used as the sleeve (202) may be continuous, and sleeved on the draw line (201), as shown in FIG. 31A; or may be discontinuous, and sleeved on the draw line (201) in segments, as shown in FIG. 31B.

Embodiment 32: A Pull Line of a Pearl Necklace Type of the Present Invention Referring to FIG. 32, this embodiment shows a pull line (2) of a pearl necklace type of the present invention, which is different from Embodiment 29 and Embodiment 10 in that: the draw line (201) is provided with beads (203), and the beads (203) may be riveted to the draw line (201), or may be strung on the draw line (201) in the form a pearl necklace, so that the string of beads (203) constitutes the sleeve (202). The beads (203) constituting the sleeve (202) are made of a medical metal material or a medical polymer material, which is selected from a group consisting of: metal materials, including titanium and titanium alloy and medical grade stainless steel; and polymer materials, including medical grade polytetrafluoroethylene, medical grade polycarbonate (PC), medical grade polythene (PE), medical grade polyurethane (PU) and medical grade polypropylene (PP). The beads made of a medical polymer material are less easily detected by X-ray than metal beads. In this embodiment, the beads are specifically made of titanium metal, and are each provided with a through hole matching with the draw line (201), for the draw line (201) to pass through. The titanium metal beads are strung on the draw line (201) to form the sleeve (202), so as to increase the contact area between the tongue tissues and the pull line (2), and facilitate growth and attachment of the tongue tissues.

The present invention provides a method for treating OSAHS, including:

providing an implanted tongue pulling device, where the tongue pulling device is implanted into the mandible (5) and the tongue body (4) of a human body to tighten the tongue dorsum (42) and/or the tongue base (41), is suitable for treating OSAHS, and includes:

a pull plate (1), being a flat implant capable of being implanted under the mucous membrane layer of the tongue body, and including through holes (101) allowing growth and penetration of fibrous tissues and pull line fixing mechanisms (102);

a pull line (2), being a thread made of a material capable of being implanted into the human body for a long term; and a retractor (3), including a control switch (301) capable of adjusting a tension of the pull line (2), a pull line fixing device (302) capable of fixing the pull line, and a casing (304), the control switch (301) and the pull line fixing device (302) being mounted in the casing (304), where the pull line (2) has one end connected to the pull plate (1) and the other end fixed to the retractor (3);

The Present Invention has the Following Prominent Advantages:

The patient after surgery can adjust the tightening degree of the implanted tongue pulling device of the present invention to the tongue dorsum (42) and/or the tongue base (41). In a non-sleeping state, the pulling force of the tongue pulling device of the present invention to the tongue dorsum (42) and/or the tongue base (41) is small so as to facilitate the movement of the tongue. Before sleep, by pressing the control switch (301) outside the skin of the mandible, the pulling force of the tongue pulling device of the present invention to the tongue dorsum (42) and/or the tongue base (41) may be increased to adjust the forward pulling distance of the tongue dorsum (42) and/or the tongue base (41), so as to keep the palatopharyngeal portion open, thereby preventing OSAHS.

Through animal experiments and clinical studies of more than five years, the tongue pulling device of the present invention has overcome numerous technical barriers, particularly, problems such as how to avoid cutting the tongue muscles and how to create a conduit for minimally invasive surgery. Current clinical studies indicate that after surgery, the patients feel good, and have normal speech and swallowing functions. Therefore, the present invention surely has good efficacy, and is an effective method for treating OSAHS.

It should be noted that, the structures disclosed and described in the present invention may be replaced by other structure with the same effect, and the embodiments described in the present invention are not intended to limit the present invention. Though the preferred embodiments of the present invention have been introduced and described in the specification, persons skilled in the art should know that these embodiments are merely described by way of example, and persons skilled in the art may make various changes, improvements, and replacements without departing from the present invention. Therefore, the protection scope of the present invention should be defined in accordance with the spirit and scope of the appended claims of the present invention.

The invention claimed is:

1. A pull plate that is implanted into a tongue body of a patient to retract a tongue dorsum and/or a junction between the tongue dorsum and a tongue base, the pull plate comprising:
   a flat-shaped implant made of a medical metal material;
   medical films wrapped around the pull plate; and
   a plurality of through holes on the pull plate, each of the through holes having a respective diameter between 0.1 mm to 4 mm;
   wherein the pull plate is connected to a first end of a pull line that attaches to the pull plate by going through two or more of the through holes, the pull line having an adjustable length that is adjusted using a control switch that is connected to a second end of the pull line and according to a sleep state or a non-sleep state of the patient.

2. The pull plate according to claim 1, wherein the pull plate further comprises a left-side pull plate and a right-side pull plate; the left-side pull plate and the right-side pull plate are assembled together through a mechanical connection mechanism; and a gap and junction are formed between the left-side pull plate and the right-side pull plate.

3. The pull plate according to claim 2, wherein the gap has a width between 2 mm and 5 mm and a length between 5 mm and 15 mm.

4. The pull plate according to claim 2, wherein the mechanical connection mechanism is a mechanical fixing mechanism capable of fixing two metal plates, and the mechanical connection mechanism is selected from a group consisting of a rivet structure, a concave-convex engagement structure, and a thread fixing structure.

5. The pull plate according to claim 1, further comprising a frame of the pull plate that is a mesh formed by braided elastic wires, and the elastic wires are capable of moving in a gap between the medical films.

6. The pull plate according to claim 1, wherein the pull plate has a curved surface matching with a shape of the tongue dorsum and/or the tongue base, and the curved surface has a shape selected from the group consisting of a rectangle, a square, a trapezoid, a circle, an ellipse, a V-shape, a U-shape and an H-shape.

* * * * *